(12) United States Patent
Matusaitis et al.

(10) Patent No.: US 10,912,483 B2
(45) Date of Patent: Feb. 9, 2021

(54) HANDHELD DEVICES FOR USE IN MEDICAL PROCEDURES

(71) Applicant: EDGE SURGICAL, INC., Chicago, IL (US)

(72) Inventors: Tomas Matusaitis, Chicago, IL (US); Kenneth Hoos, Chicago, IL (US); Christopher Wilson, Chicago, IL (US); Robert F. Rioux, Ashland, MA (US); Nitin Khanna, Chicago, IL (US); Frank Phillips, Chicago, IL (US); Jim A. Youssef, Durango, CO (US); Aniruddha Raina, Troy, MI (US); Antonio Belton, Chicago, IL (US)

(73) Assignee: EDGE SURGICAL, INC., Chicago, IL (US)

( * ) Notice: Subject to any disclaimer, the term of this patent is extended or adjusted under 35 U.S.C. 154(b) by 154 days.

(21) Appl. No.: 16/292,955

(22) Filed: Mar. 5, 2019

(65) Prior Publication Data

US 2019/0269420 A1 Sep. 5, 2019

Related U.S. Application Data

(60) Provisional application No. 62/638,605, filed on Mar. 5, 2018.

(51) Int. Cl.
*A61B 17/16* (2006.01)
*A61B 5/00* (2006.01)
(Continued)

(52) U.S. Cl.
CPC ............ *A61B 5/053* (2013.01); *A61B 5/0492* (2013.01); *A61B 5/05* (2013.01); *A61B 5/4504* (2013.01);
(Continued)

(58) Field of Classification Search
CPC .................................. A61B 5/053; A61B 5/05
See application file for complete search history.

(56) References Cited

U.S. PATENT DOCUMENTS

| 1,987,504 | A | * | 1/1935 | Denz | ....................... B23B 47/34 |
| | | | | | 279/49 |
| 2,689,408 | A | * | 9/1954 | Cornell | .................... G01B 3/28 |
| | | | | | 33/544 |

(Continued)

FOREIGN PATENT DOCUMENTS

| EP | 1850762 A1 | 11/2007 |
| EP | 3040039 A1 | 7/2016 |

(Continued)

OTHER PUBLICATIONS

SpineGuard Press Release, "SpineGuard will launch PediGuard Threaded DSG (TM) device at " SpineWeek 2016 world conference in Singapore, May 9, 2016 (2 pages).

(Continued)

*Primary Examiner* — Christian A Sevilla
(74) *Attorney, Agent, or Firm* — Brown Rudnick LLP

(57) ABSTRACT

The invention is a system and a handheld device for use in open or minimally invasive surgical procedures, such as a bone implant fixation procedure. The handheld device is configured to perform various functions during a bone implant fixation procedure, including performing at least one of: penetration of a bone to form a hole or opening for receipt of a screw; neuromonitoring, in cooperation with a neuromonitoring device, of the hole during, or post-, formation of the hole so as to sense any nearby nerves adjacent to the hole that may be in the path of a screw, or otherwise affected, when a screw is placed within the hole; neurostimulation, in cooperation with a neuromonitoring device, of nerves adjacent to the hole during, or post-, formation of the hole; and measuring of a depth of the hole and providing (Continued)

a digital measurement of the depth to assist the surgeon in selecting the appropriate length of screw.

20 Claims, 41 Drawing Sheets

(51) Int. Cl.
| | | |
|---|---|---|
| *A61B 5/053* | (2021.01) | |
| *A61B 5/0492* | (2006.01) | |
| *A61B 5/05* | (2021.01) | |
| *A61B 90/00* | (2016.01) | |
| *A61B 17/00* | (2006.01) | |

(52) U.S. Cl.
CPC .......... *A61B 5/4893* (2013.01); *A61B 5/6878* (2013.01); *A61B 17/1615* (2013.01); *A61B 17/1626* (2013.01); *A61B 17/1633* (2013.01); *A61B 5/6851* (2013.01); *A61B 2017/00022* (2013.01); *A61B 2017/00115* (2013.01); *A61B 2017/00407* (2013.01); *A61B 2017/00464* (2013.01); *A61B 2090/062* (2016.02)

(56) References Cited

U.S. PATENT DOCUMENTS

| | | |
|---|---|---|
| 3,058,225 A | 10/1962 | Ward |
| 5,013,318 A | 5/1991 | Spranza, III |
| 5,062,748 A * | 11/1991 | Kishida ............... B23B 51/0453 408/206 |
| 5,772,661 A | 6/1998 | Michelson |
| 5,860,973 A | 1/1999 | Michelson |
| 5,928,243 A | 7/1999 | Guyer |
| 6,235,028 B1 | 5/2001 | Brumfield et al. |
| 6,428,542 B1 | 8/2002 | Michelson |
| 6,466,817 B1 | 10/2002 | Kaula et al. |
| 6,500,128 B2 | 12/2002 | Marino |
| 6,530,929 B1 | 3/2003 | Justis et al. |
| 6,592,586 B1 | 7/2003 | Michelson |
| 6,796,985 B2 | 9/2004 | Bolger et al. |
| 6,916,320 B2 | 7/2005 | Michelson |
| 6,936,050 B2 | 8/2005 | Michelson |
| 6,936,051 B2 | 8/2005 | Michelson |
| 6,945,933 B2 | 9/2005 | Branch et al. |
| 6,969,390 B2 | 11/2005 | Michelson |
| 7,008,422 B2 | 3/2006 | Foley et al. |
| 7,165,336 B2 | 1/2007 | Kim |
| 7,177,677 B2 | 2/2007 | Kaula et al. |
| 7,444,756 B2 | 11/2008 | Kim |
| 7,493,703 B2 | 2/2009 | Kim et al. |
| 7,522,953 B2 | 4/2009 | Kaula et al. |
| 7,607,238 B2 | 10/2009 | Kim et al. |
| 7,657,308 B2 | 2/2010 | Miles et al. |
| 7,664,544 B2 | 2/2010 | Miles et al. |
| 7,676,943 B2 | 3/2010 | Kim et al. |
| 7,685,735 B2 | 3/2010 | Kim |
| 7,730,629 B2 | 6/2010 | Kim |
| 7,878,981 B2 | 2/2011 | Strother et al. |
| 7,895,762 B2 | 3/2011 | Kim et al. |
| 7,895,767 B2 | 3/2011 | Harshbarger et al. |
| 7,896,815 B2 | 3/2011 | Thrope et al. |
| 7,942,826 B1 | 5/2011 | Scholl et al. |
| 7,963,927 B2 | 6/2011 | Kelleher et al. |
| 7,991,463 B2 | 8/2011 | Kelleher et al. |
| 8,050,769 B2 | 11/2011 | Gharib et al. |
| 8,068,912 B2 | 11/2011 | Kaula et al. |
| D652,921 S | 1/2012 | Miles et al. |
| 8,147,421 B2 | 4/2012 | Farquhar et al. |
| 8,172,768 B2 | 5/2012 | Strother et al. |
| 8,221,427 B2 | 7/2012 | Roh |
| D666,294 S | 8/2012 | Miles et al. |
| 8,255,044 B2 | 8/2012 | Miles et al. |
| 8,255,045 B2 | 8/2012 | Gharib et al. |
| 8,442,621 B2 | 5/2013 | Gorek et al. |
| 8,500,652 B2 | 8/2013 | Strother et al. |
| 8,562,539 B2 | 10/2013 | Marino |
| 8,591,431 B2 | 11/2013 | Calancie et al. |
| 8,641,638 B2 | 2/2014 | Kelleher et al. |
| 8,958,869 B2 | 2/2015 | Kelleher et al. |
| 8,989,866 B2 | 3/2015 | Gharib et al. |
| 9,131,947 B2 | 9/2015 | Ferree |
| 9,232,906 B2 * | 1/2016 | Wolf, II ............... A61B 5/4836 |
| 9,295,396 B2 | 3/2016 | Gharib et al. |
| 9,392,953 B1 | 7/2016 | Gharib |
| 9,700,228 B2 | 7/2017 | Gharib et al. |
| 9,743,853 B2 | 8/2017 | Kelleher et al. |
| 9,750,508 B1 | 9/2017 | Barnes et al. |
| 9,757,072 B1 | 9/2017 | Urbalejo |
| 9,801,668 B1 | 10/2017 | Ferree |
| 9,848,861 B2 | 12/2017 | Miles et al. |
| 9,931,077 B2 | 4/2018 | Kaula et al. |
| 2002/0104230 A1 | 8/2002 | White |
| 2003/0139662 A1 * | 7/2003 | Seidman ............... A61B 5/0507 600/407 |
| 2005/0066535 A1 | 3/2005 | Rupp et al. |
| 2005/0119660 A1 * | 6/2005 | Bourlion ............... A61B 5/417 606/80 |
| 2005/0261585 A1 * | 11/2005 | Makin ............... A61B 5/053 600/439 |
| 2006/0224161 A1 | 10/2006 | Bhattacharyya |
| 2007/0088366 A1 | 4/2007 | Fernandez |
| 2008/0104855 A1 | 5/2008 | Kim et al. |
| 2008/0125637 A1 | 5/2008 | Geist et al. |
| 2008/0262526 A1 * | 10/2008 | Neubardt ............ A61B 17/1615 606/180 |
| 2008/0269631 A1 * | 10/2008 | Denison ............... A61B 5/7275 600/544 |
| 2009/0005786 A1 | 1/2009 | Prien et al. |
| 2009/0157088 A1 | 6/2009 | Mengato |
| 2009/0163901 A1 | 6/2009 | Fisher et al. |
| 2009/0221922 A1 * | 9/2009 | Lee ............... A61B 5/0084 600/478 |
| 2010/0198227 A1 | 8/2010 | Kim et al. |
| 2010/0256517 A1 | 10/2010 | Neubardt et al. |
| 2011/0054346 A1 | 3/2011 | Hausman et al. |
| 2011/0060238 A1 | 3/2011 | Hausman et al. |
| 2011/0060243 A1 | 3/2011 | Hausman et al. |
| 2011/0238083 A1 * | 9/2011 | Moll ............... A61B 34/76 606/130 |
| 2012/0296442 A1 | 11/2012 | Hausman |
| 2013/0096565 A1 | 4/2013 | Fritzinger |
| 2013/0172897 A1 | 7/2013 | Dell'Oca et al. |
| 2013/0245490 A1 | 9/2013 | Strother et al. |
| 2013/0296733 A1 | 11/2013 | Strother et al. |
| 2014/0073985 A1 | 3/2014 | Sakai et al. |
| 2014/0222003 A1 | 8/2014 | Herndon et al. |
| 2014/0296861 A1 | 10/2014 | McCarthy et al. |
| 2014/0336473 A1 * | 11/2014 | Greco ............... A61B 5/02055 600/301 |
| 2014/0371622 A1 | 12/2014 | Hausman et al. |
| 2015/0133944 A1 | 5/2015 | Kortenbach |
| 2018/0195848 A1 | 7/2018 | Rioux et al. |
| 2018/0252666 A1 * | 9/2018 | Fotopoulou .......... G01N 27/403 |
| 2018/0256277 A1 | 9/2018 | Garvey et al. |
| 2018/0360448 A1 * | 12/2018 | Harris ............... A61B 17/068 |
| 2020/0289173 A1 * | 9/2020 | Ferree ............... A61B 5/04001 |

FOREIGN PATENT DOCUMENTS

| | | | |
|---|---|---|---|
| WO | 2005027745 A1 | 3/2005 | |
| WO | WO-2005027745 A1 * | 3/2005 | ............. A61B 90/06 |

OTHER PUBLICATIONS

SpineGuard, "PediGuard" brochure, May 13, 2012 (2 pages).
SpineGuard, "Clinical Evidence for the Use of PediGuard in Spine Surgery" brochure, May 21, 2012 (5 pages).
NuVasive, 510(k) Premarket Notification, NuVasive NVMS System, May 16, 2014 (12 pages).
NuVasive, "An Introduction to NVM5 Nerve Monitoring System" brochure, Jan. 6, 2017 (8 pages).

(56) References Cited

OTHER PUBLICATIONS

NuVasive, "XLIF Designed: NVM5" brochure, Jan. 4, 2017 (3 pages).
Medtronic, "Nim-Spine System", Medtronic Sofamor Danek, 2005 (4 Pages).
Checkpoint Surgical, "Nerve Repair: Manual", Checkpoint Surgical Inc., 2016 (44 Pages).
Checkpoint Surgical, "A Signifcant Advance in Neuroprotective Surgery", Checkpoint Surgical Inc., 2014 (6 Pages).
Checkpoint Surgical, "The Next Generation in Neuroprotective Surgical Technology", Checkpoint Surgical Inc., 2014 (6 Pages).
International Search Report and Written Opinion dated May 24, 2018 for International Application No. PCT/US2017/059709 (13 Pages).
International Search Report and Written Opinion dated May 24, 2018 for International Application No. PCT/US2017/059714 (13 Pages).
Surgionix, "Surgical Technique Guide", Surgionix Ltd., 2013 (12 Pages).
Medartis "Surgical Technique—Step by Step, APTUS Hand", Medartis AG, 2012 (20 Pages).
Medartis "Ordering Catalog", Medartis AG, 2017 (100 Pages).
International Search Report and Written Opinion dated Jun. 13, 2009 for International Application No. PCT/US2019/020709 (10 pages).

\* cited by examiner

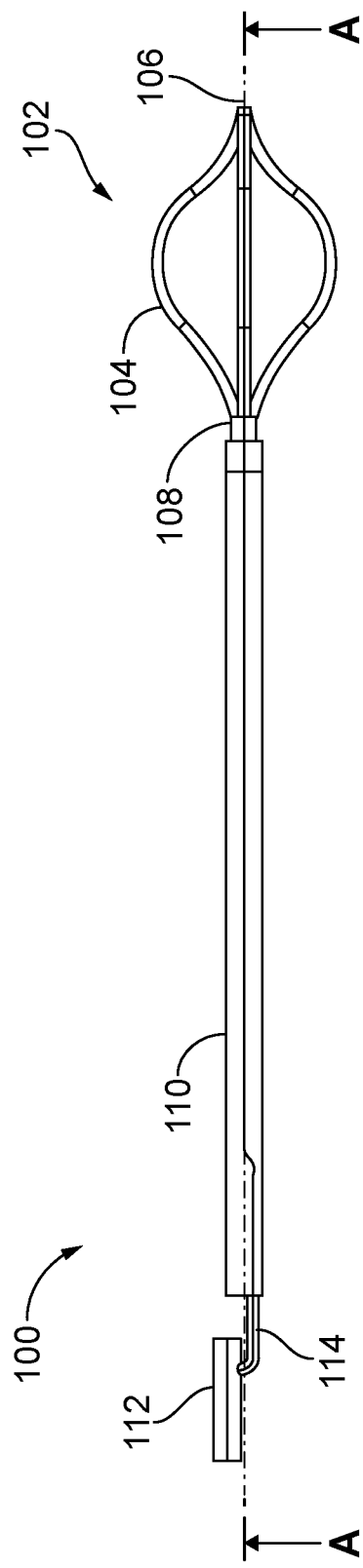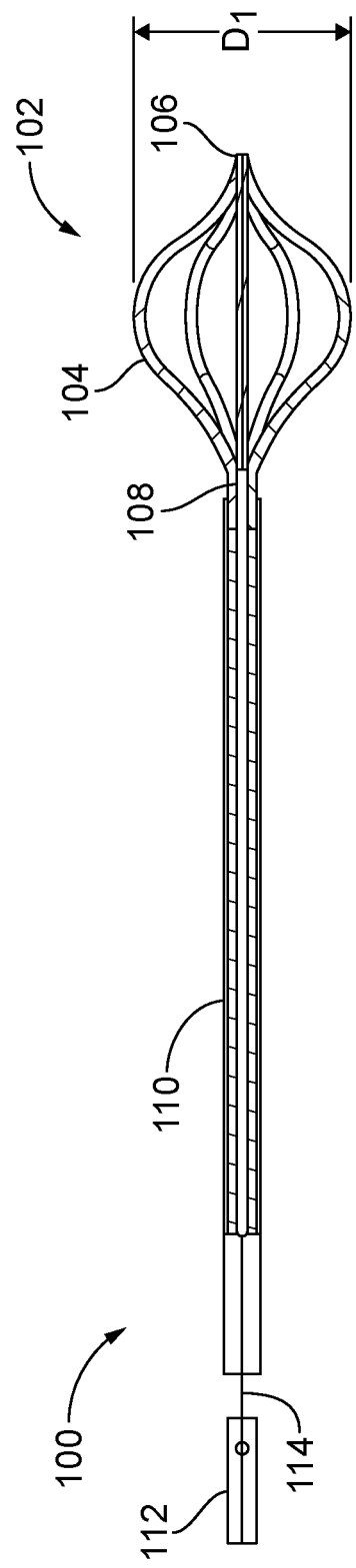
FIG. 2
FIG. 3

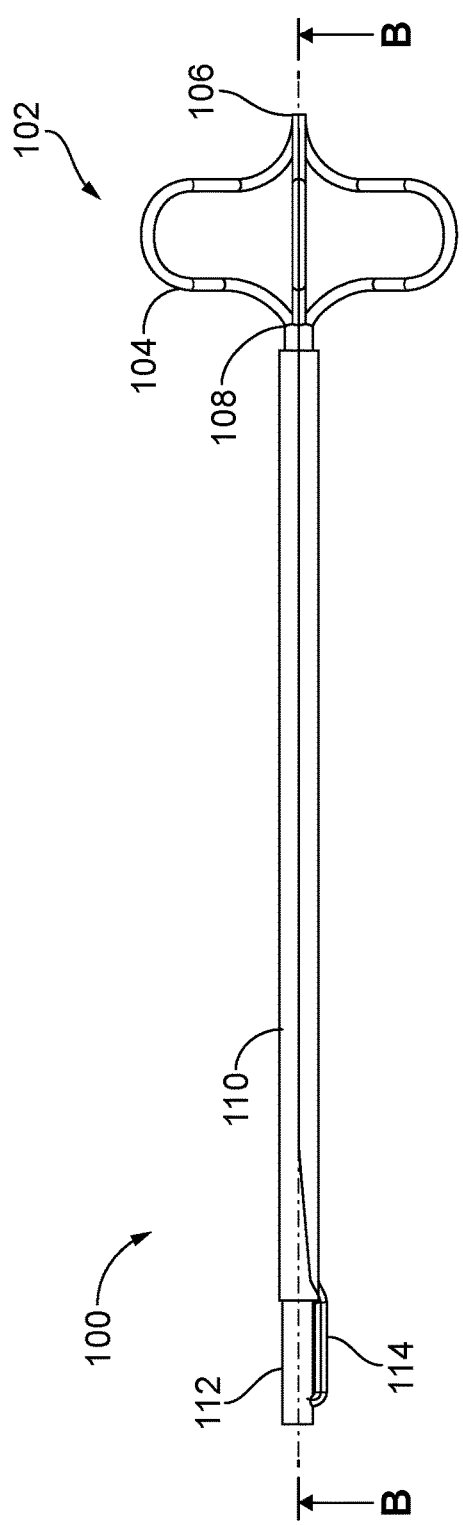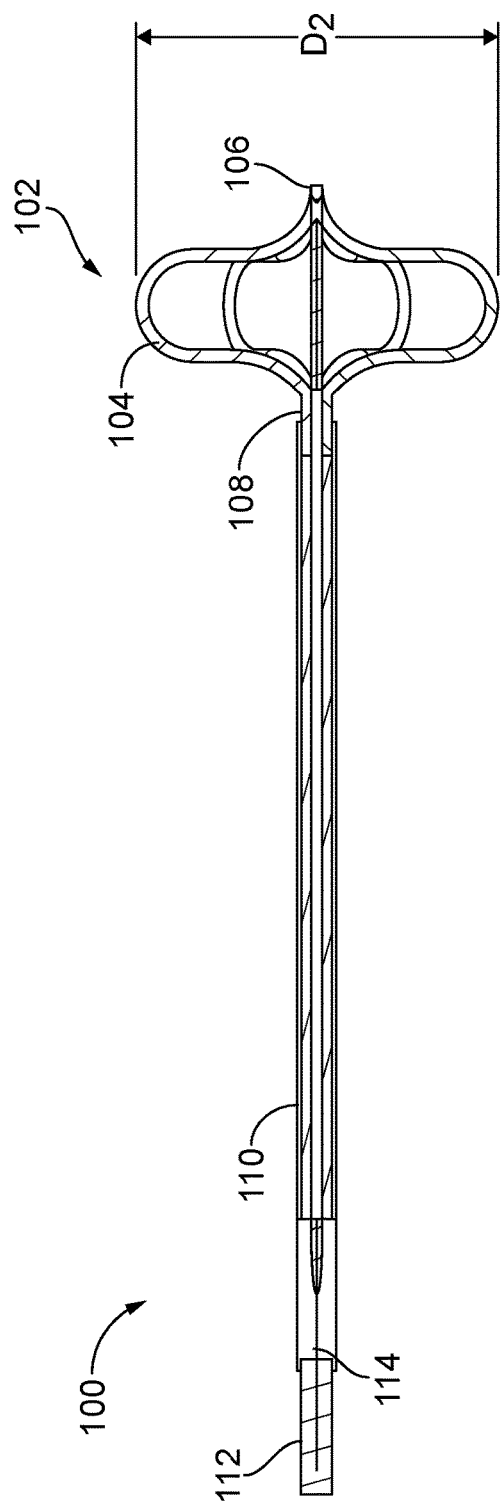

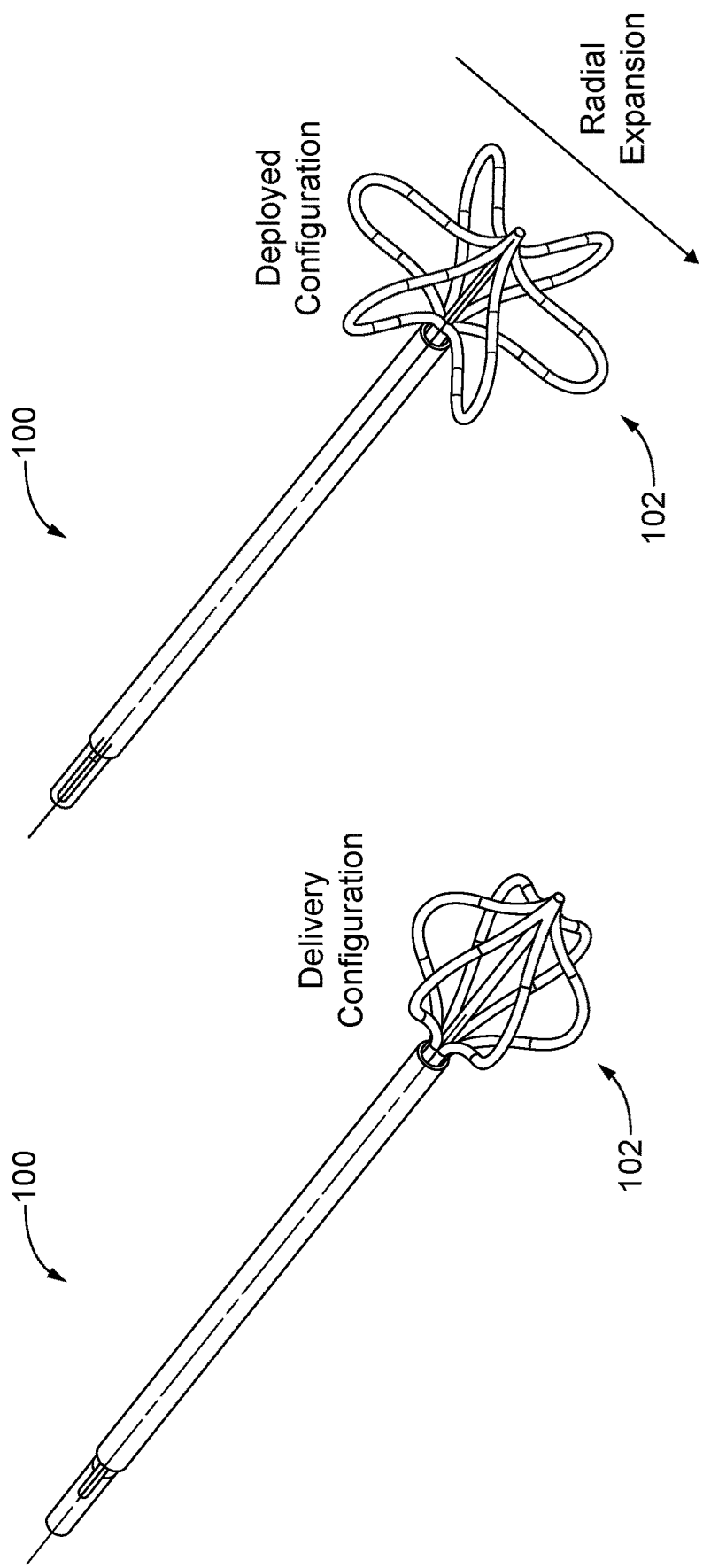

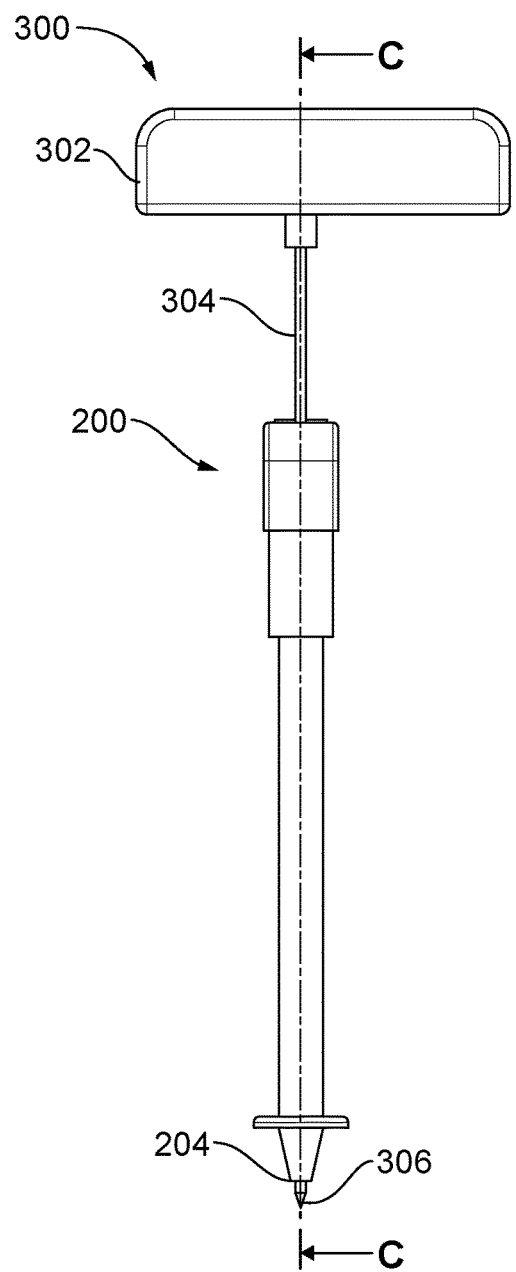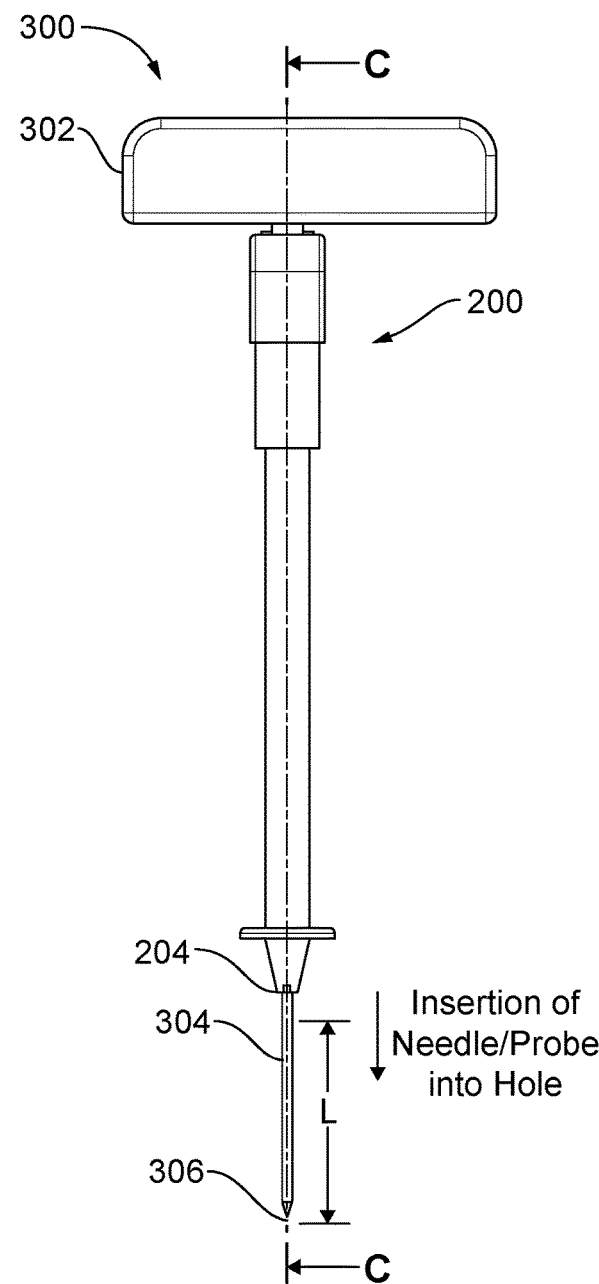
*FIG. 10A*   *FIG. 10B*

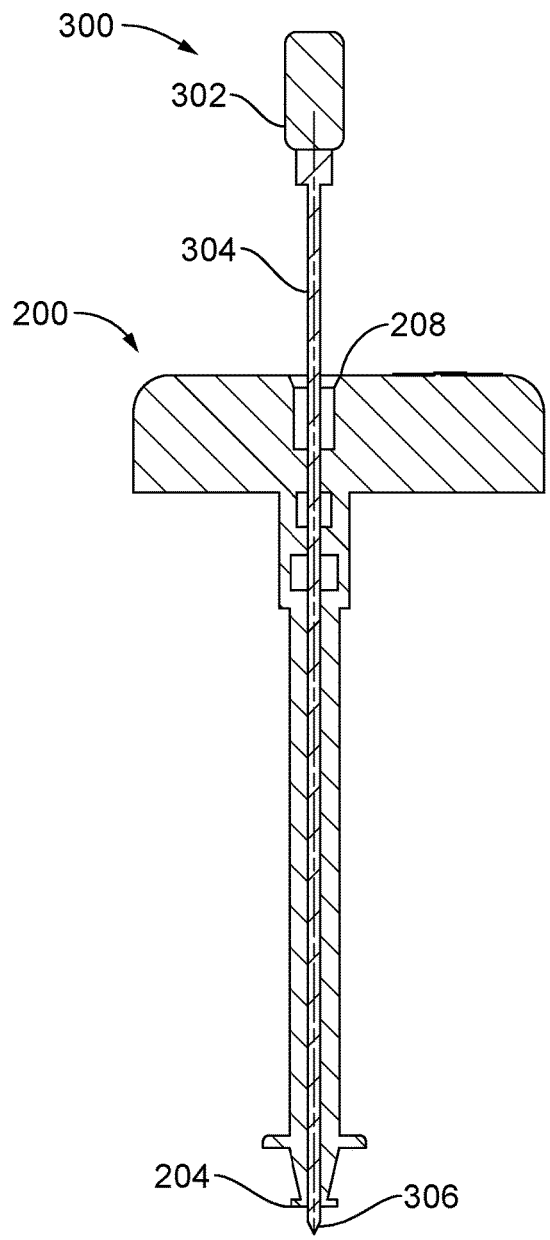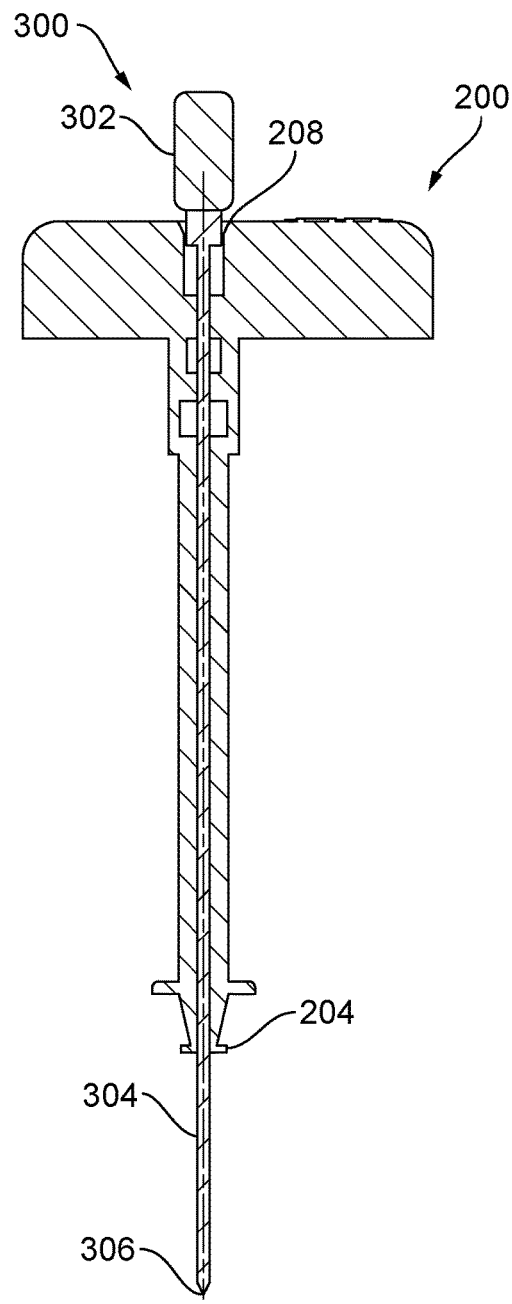
FIG. 11A  FIG. 11B

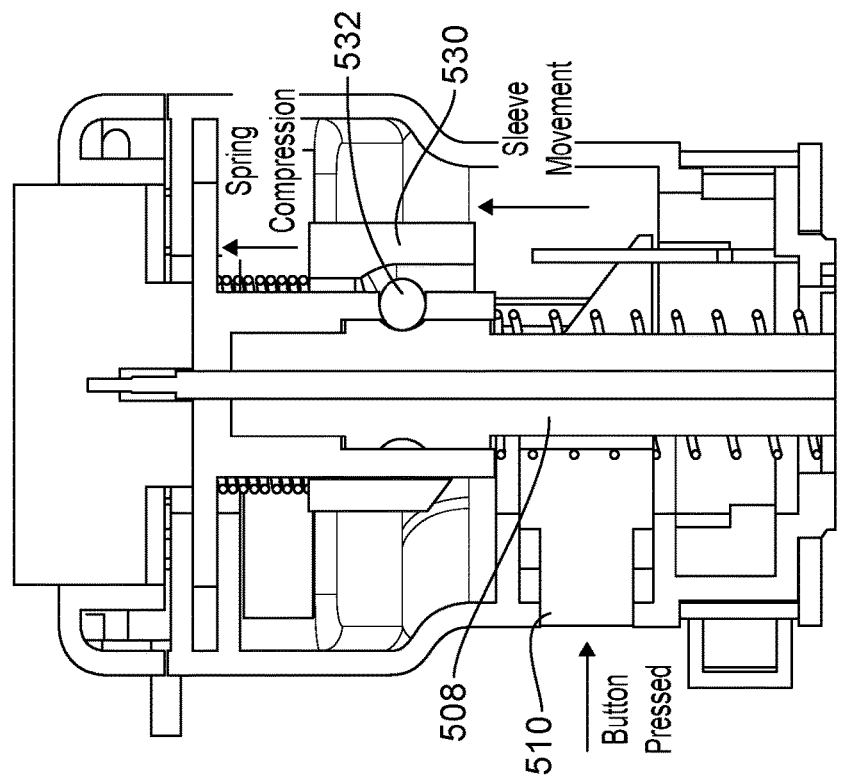
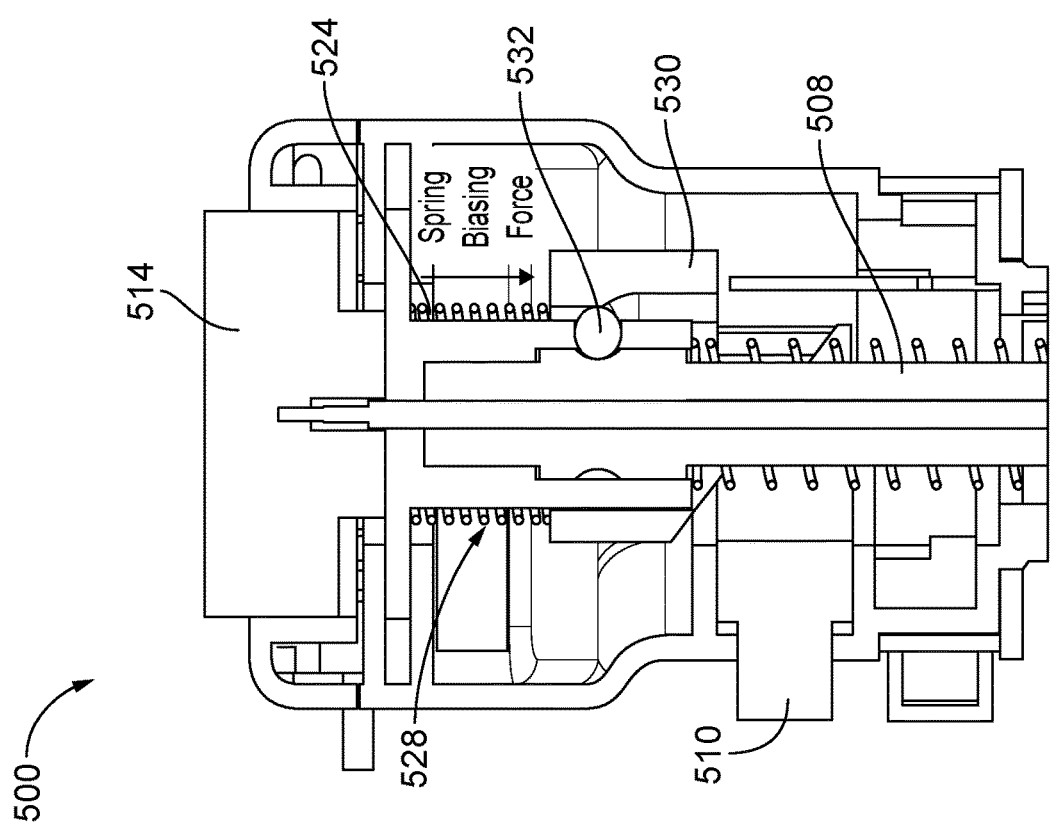
FIG. 20B
FIG. 20A

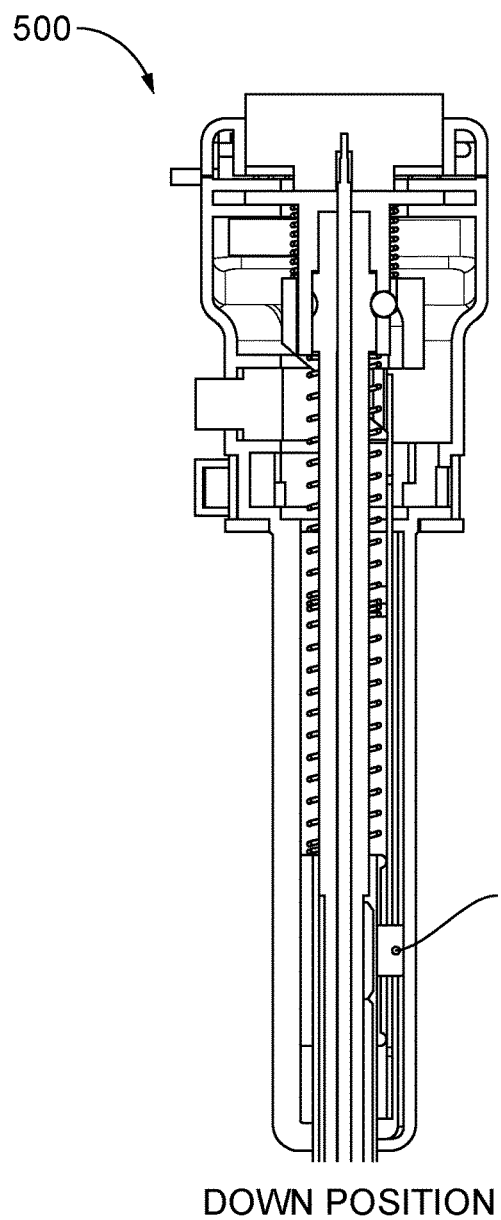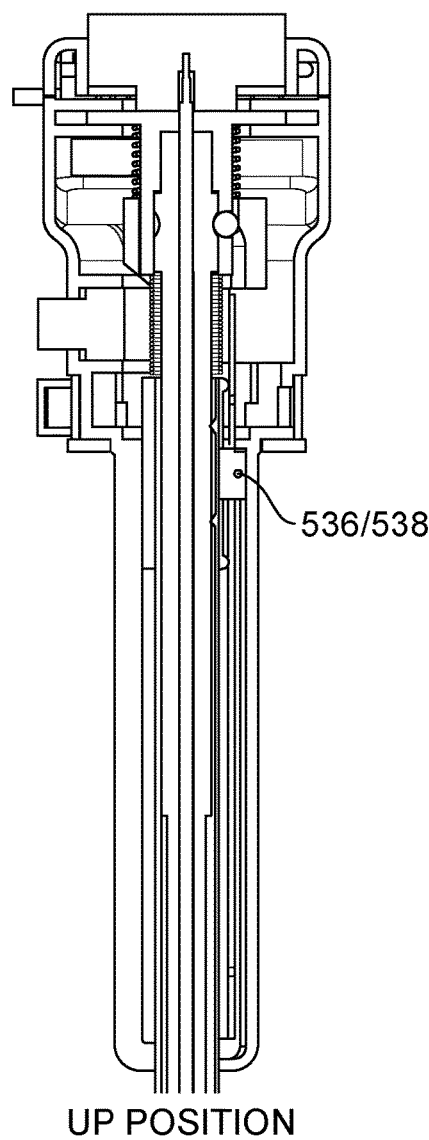
DOWN POSITION　　UP POSITION
*FIG. 22A*　　*FIG. 22B*

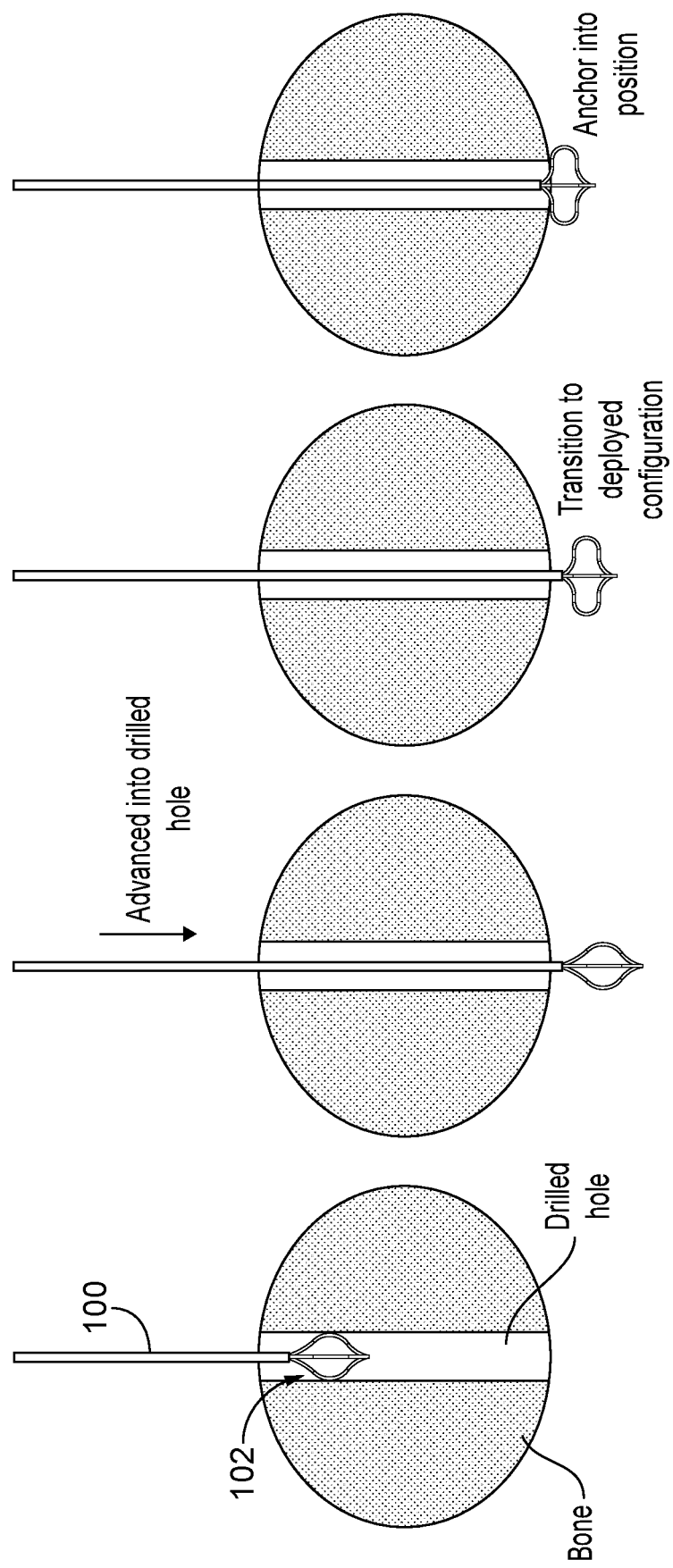

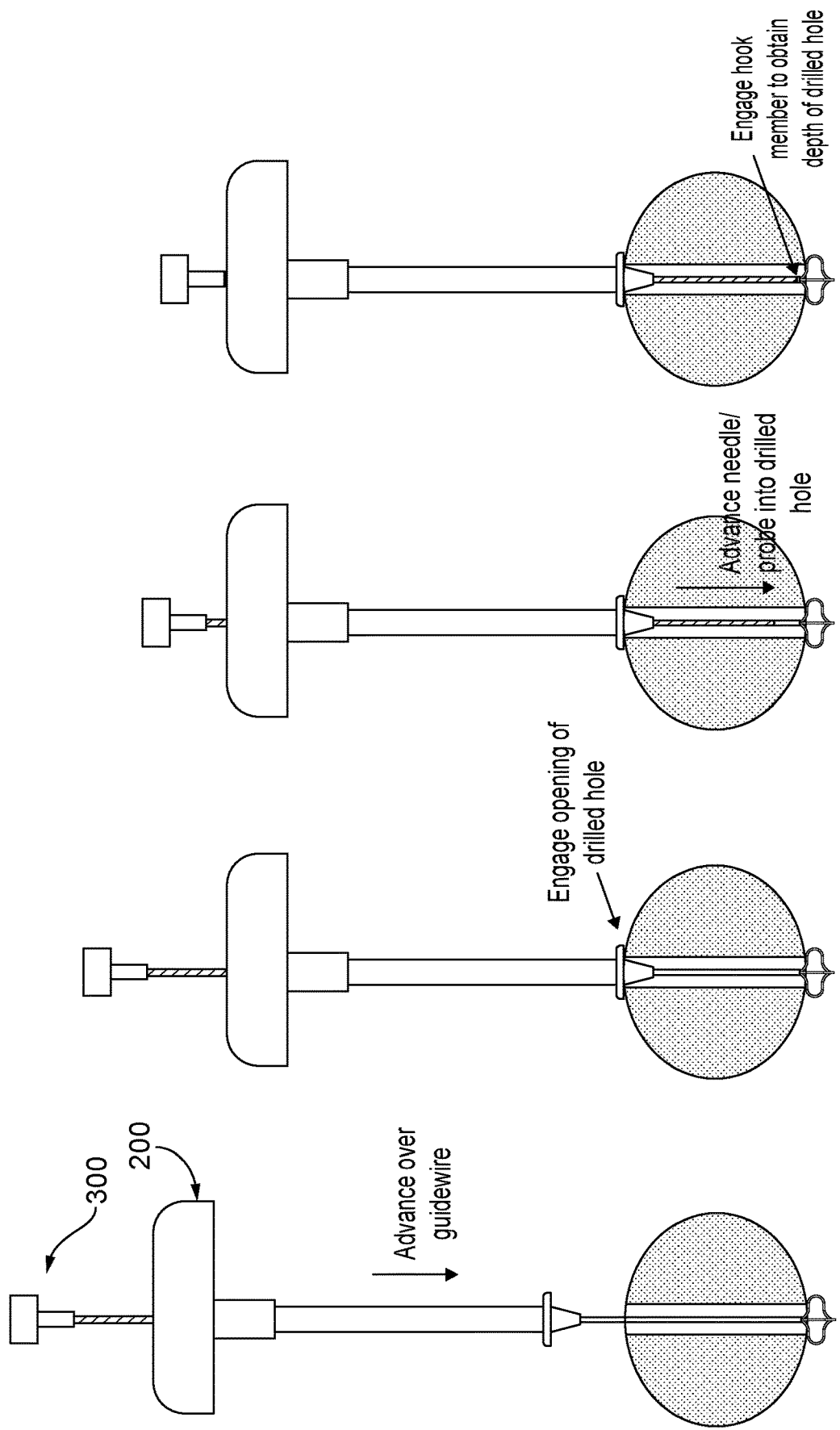

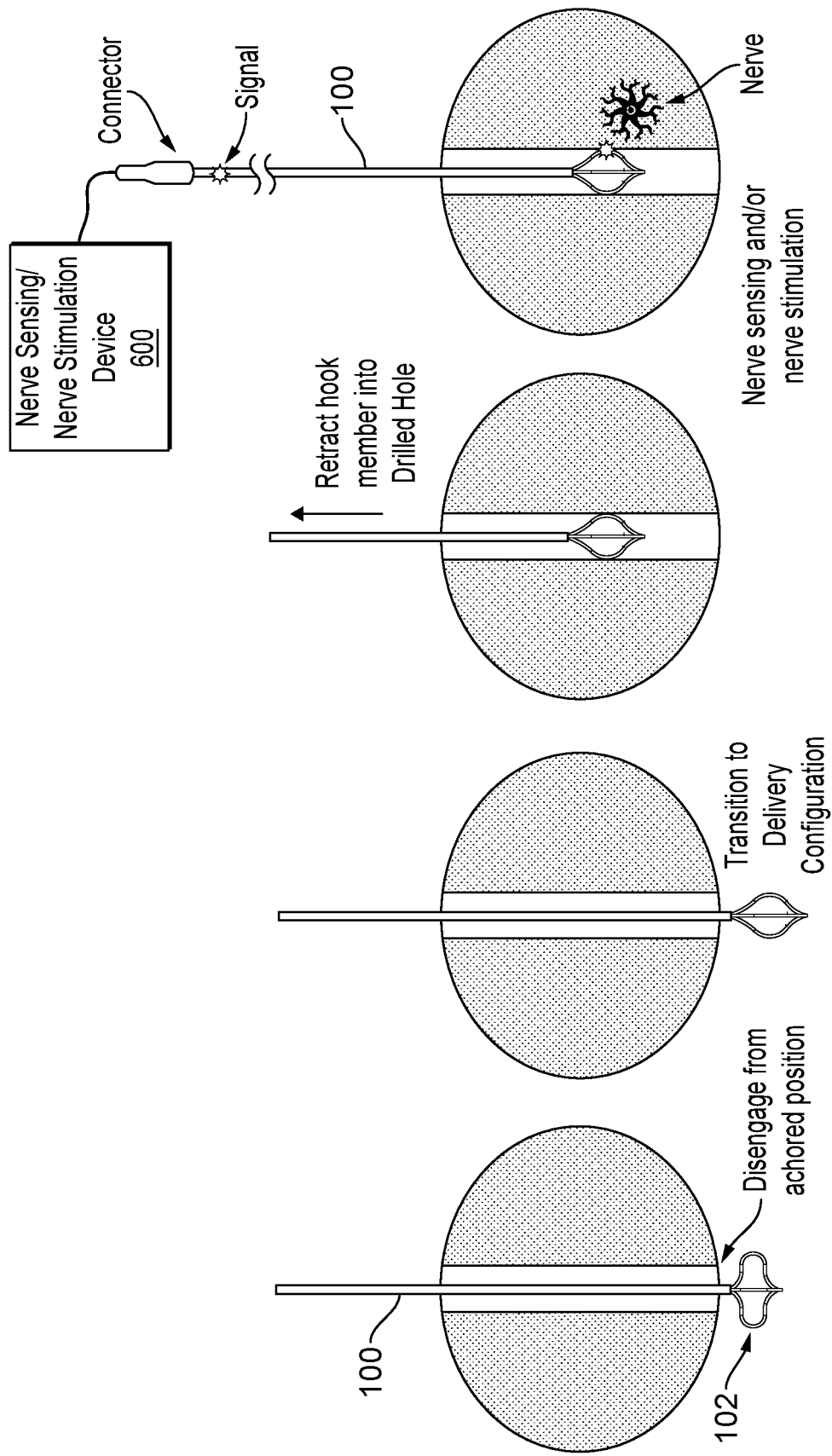

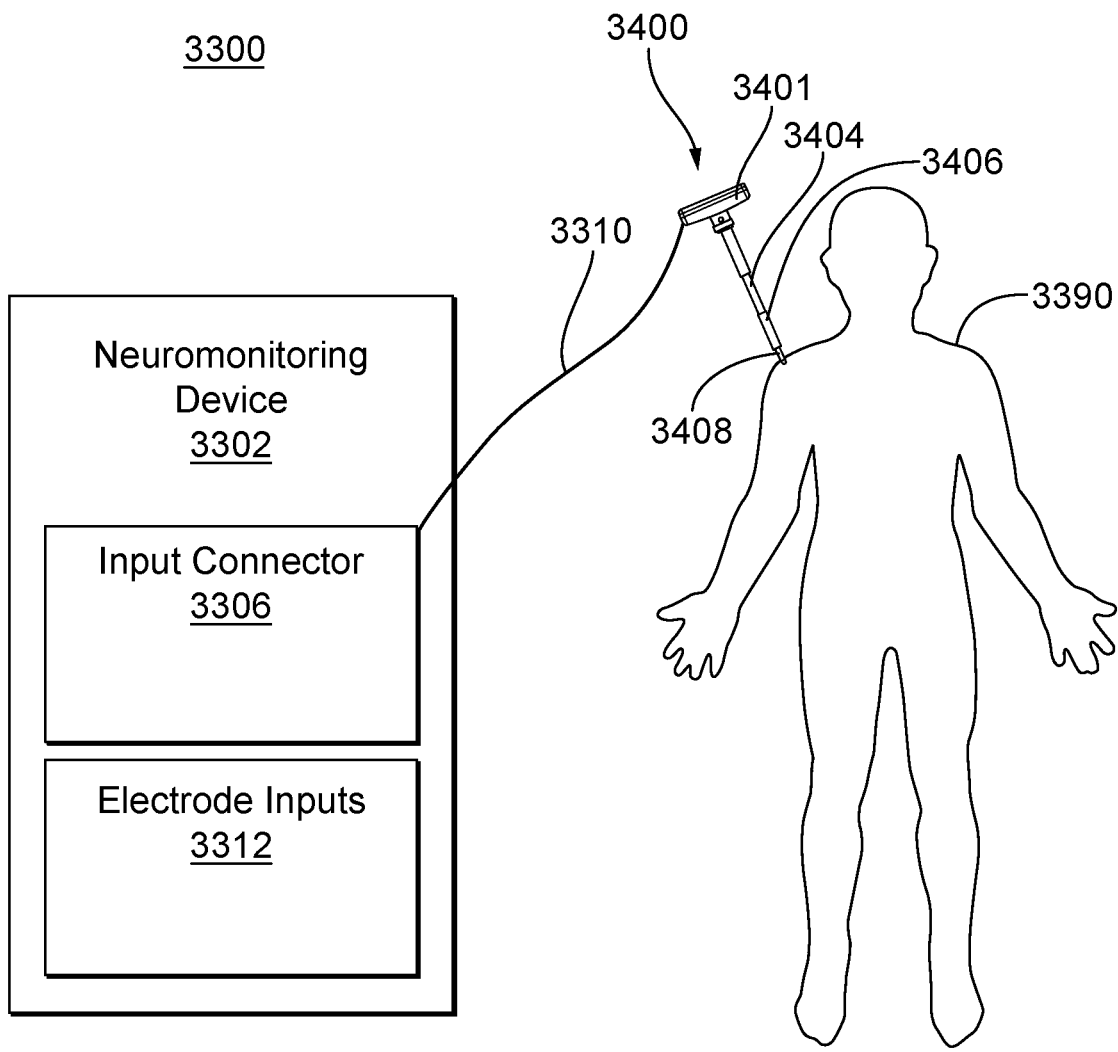
FIG. 33A  FIG. 33B

HANDHELD DEVICES FOR USE IN MEDICAL PROCEDURES

CROSS-REFERENCE TO RELATED APPLICATIONS

This application claims the benefit of, and priority to, U.S. Provisional Application 62/638,605, filed Mar. 5, 2018, the contents of which are incorporated by reference.

FIELD

The present disclosure relates to a system including a handheld device for use in open and minimally invasive surgical procedures.

BACKGROUND

Orthopedics is a medical specialty concerned with the correction of deformities or functional impairments of the skeletal system, especially the extremities and the spine, and associated structures, such as muscles and ligaments. Some orthopedic surgical procedures require surgeons to secure a device to one or more bones of a patient. For example, in some procedures, the surgeon may span and secure one or more bones, or pieces of a single bone, using a bone plate and one or more fasteners, such as screws. Other bone-related surgical procedures, however, may not require a bone plate and may instead solely rely on the use of one or more screws (e.g., securing a transplanted tendon).

In such bone-related surgical procedures, prior to attachment of a screw to bone, a hole or opening is typically drilled, or otherwise formed, into the bone to accommodate the screw. The surgeon must take great care when creating the opening for receipt of the screw. For example, in spinal surgery, when drilling or penetrating the pedicle, the bone cortex may be inadvertently pierced, broken or otherwise damaged by the penetrating instrument (e.g., the drill bit or piercing tip of an awl) and/or an adjacent nerve may be impinged. In turn, the patient may experience pain or potential paralysis (temporary or permanent). Furthermore, an improperly formed hole may then lead to poor positioning of the pedicle screw. In turn, the poor placement of one or more pedicle screws may also induce pain, hemorrhage, or potentially even paralysis (temporary or permanent) in the patient, and require another surgical intervention or, in certain cases, cause irreparable damage.

The current development trend in spine surgery is toward the performance of increasingly smaller incisions and less invasive surgical exposures to reduce collateral damage to normal soft tissues along the path of the surgical approach. For example, some current advances in spine surgical techniques involve the development of minimally invasive, tissue sparing approaches performed through tiny incisions under television image intensifier fluoroscopic guidance. For example, surgeons may utilize special surgical instruments modified to work in such small openings such as curettes, osteotomes, reamers, probes, retractors, forceps or the like to access the spine while monitoring their technique using a microscope, fluoroscope (real-time X-ray monitoring), and/ or an endoscope (a miniature TV camera with associated viewing monitor). Surgeons may sometimes use equipment for surgical navigation, which is expensive and cumbersome to implement, as well as equipment for stimulating nerves near a surgical site or for monitoring of sensory and/or motor evoked potentials, this being less expensive but also restricting as it requires the presence of a specialist whose mission is solely to carry out this monitoring operation. As a result, in many instances, the operators may rely solely on their knowledge of anatomy and their experience in order to accomplish spinal procedures, and thus the accuracy of pedicle screw placement remains a critical issue in spine surgery, as misplaced pedicles screws can lead to neurologic or vascular complications.

Furthermore, even if a hole is appropriately formed without complication, it is critical that the surgeon select a screw of appropriate length. For example, if the selected screw is too long, the distal end of the screw may pass through the end of the drilled hole and cause damage to the bone and/or protrude entirely through the bone, which can have deleterious effects, such as damage to surrounding tissue and/or pain and discomfort, or more serious complications, for the patient. For example, in some instances, the bone may abut against soft tissues that may be harmed if the screw is too long and may result in irritation of or damage to the soft parts. Additionally, a screw that protrudes through the bone may be tactilely felt by the patient, may prevent soft tissues (e.g., tendons, ligaments, or muscles) from moving over the bone surface as intended, or may even pierce the skin, which can lead to serious infection and complications.

The selection of an appropriate length screw is particularly important in spinal fixation procedures, such as lumbar sacral fusion and the correction of spinal deformities such as scoliotic curves. As an example, a screw mounted in the pedicle portion of the human spine should not extend to a point where the screw contacts the spinal cord itself, an event that can cause irreparable nervous system damage including paralysis. Accordingly, the determination of a length of the hole is important for choosing the appropriate length screw.

A depth gauge is commonly employed for directly measuring the depth of the hole from the top, drilling side to the bottom, opposite side of the hole. Currently, many designs are known and utilized for measuring the depth of a hole or bore in a portion of a bone. Generally speaking, these designs utilize a central probe member having a barb at a distal end, and a sleeve or channel member. The probe member is inserted into the pilot hole while the surgeon attempts to find the surface with the barb. More specifically, the probe member is inserted to a depth greater than the depth of the pilot hole so that the barb is beyond the opposite side, at which point the surgeon finds the surface by hooking the barb to the opposite side.

The probe member is received in the sleeve or channel member and may reciprocate relative thereto. The channel member has graduated markings along a portion of its length, typically in inches and/or millimeters. A marker is laterally secured to the probe member such that, as the probe member shifts relative to the channel member, the marker indicates the relative shift between the probe member and the channel member. Accordingly, once the probe member has been secured to the opposite side of the bone, the channel member is shifted relative to the probe member and toward the bone until the channel member abuts the surface of the bone. The depth gauge is then read by examining graduated markings indicated by the probe member marker.

A number of problems are experienced with this depth gauge. As an initial point, the components are typically made with surgical-grade stainless steel, and the graduated markings are embossed therein. Therefore, the brightness of the operating room lights on the highly reflective surface can make the markings difficult to read. The markings are commonly in small increments, such as millimeters, and surgeons often have trouble differentiating between the markings, or noting partial increments. Reading these gauges, then, often requires carefully holding the depth gauge as the reading is taken, and a surgeon's effort to closely examine the reading may result in a loss of securement or purchase of the barb on the bone, thus necessitating a re-measurement and a loss of time.

Furthermore, proper reading of the markings requires a surgeon's eyes to be properly aligned with the markings. That is, a proper view of the measurement requires the surgeon to view the gauge from a lateral point of view so that the view of the probe marker aligned with the graduated markings is proper not distorted by the surgeon's elevated, standing perspective. Therefore, it is often necessary for the surgeon to bend over while using these gauges to view an accurate reading. If the depth gauge is tilted in order to make the reading, the sleeve will shift relative to the probe, thus making the measurement inaccurate and possibly causing the barb to become unsecured, as described above. In addition, removal of the depth gauge often causes the measurement to be lost. As the bone is essentially clamped, by light pressure, between the distal end of the channel member and the distal barb of the probe member, it is often necessary to retract the channel member from the bone surface in order to extract the probe from the pilot hole.

SUMMARY

The present disclosure is directed to a system including a handheld device for use in a minimally invasive surgical procedure, such as a bone implant fixation procedure. The handheld device is configured to perform various functions during a bone implant fixation procedure. In particular, a handheld device consistent with the present disclosure is configured to perform at least one of: penetration of a bone to form a hole or opening for receipt of a screw; neuromonitoring, in cooperation with a neuromonitoring device, of the hole during, or post-, formation of the hole so as to sense any nearby nerves adjacent to the hole that may be in the path of a screw, or otherwise affected, when a screw is placed within the hole; neurostimulation, in cooperation with a neuromonitoring device, of nerves adjacent to the hole during, or post-, formation of the hole; and measuring of a depth of the hole and providing a digital measurement of the depth to assist the surgeon in selecting the appropriate length of screw.

The handheld device provides an improved manner in which a hole or opening is formed in bone by providing neuromonitoring functionality during penetration into the bone, which, in turn, provides real-time, or near real-time, alerts to the surgeon as to the presence of any nearby nerves that may be in the path of a screw, or otherwise affected, when a screw is placed within the hole. This real-time or near real-time feedback may be provided to the surgeon visually (i.e., via a digital display, such as a display screen, or via a light source, such as an LED array) and/or audibly (i.e., via a speaker). The neuromonitoring feedback can facilitate repositioning of the handheld device, particularly a penetration member of the device, if there is any sensing of nearby nerves, thereby ensuring a properly formed hole and subsequently ensuring proper positioning of a screw within the hole so as to avoid inadvertent piercing, breaching, damage, or impinging upon unintended structures or tissues. The handheld device further allows for accurate measurements of the depth of a formed hole and provides a digital display of the depth measurement, thereby providing the surgeon with a quick and accurate reading upon which they rely when selecting the appropriate length screw (ensuring they do not select a screw that is either too short or too long). The handheld device further provides neurostimulation functionality during penetration into the bone to form a hole or post formation of the hole. For example, the handheld device may be used for neuromonitoring functions to determine the presence of nerves adjacent to the hole prior to placement of a screw into the hole, and nerves that are present and adjacent to the hole may then be stimulated by electrical current delivered by the handheld device. The handheld device may generate the electrical current from a source incorporated into the handheld device itself or the handheld device may be coupled to and placed in electrical connection with an input connector of a neuromonitoring device that provides pulses of electrical current to the handheld device for the neurostimulation and neuromonitoring features described herein.

The handheld device generally includes a handle including a grip portion providing a surgeon or other medical professional with a means to manipulate the device and components thereof. The handheld device further includes an awl-tap member releasably coupled to the handle and configured to penetrate bone upon manipulation of the grip portion, a depth sleeve member operably associated with the handle and configured to move relative thereto, the depth sleeve member including an elongate body including a lumen extending therethrough within which a portion of the awl-tap member is received, and a sensor operably associated with the depth sleeve member and configured to detect movement of the depth sleeve member relative to the awl-tap member and generate an electronic signal indicative of a depth of a hole created by the awl-tap member based on the detected movement.

The awl-tap member comprises a tubular body including a penetrating distal tip configured to pierce bone and to create a pilot hole within the pedicle. The body of the awl-tap member is electrically conductive and is operable to carry electrical current for neurostimulation and neuromonitoring functions. A portion adjacent to the distal tip of the awl-tap member further includes a tapping feature configured to cut, or otherwise form, a thread on the inside surface of the hole created by the distal tip of the awl-tap member. In particular, the tapping feature may generally include a set of external cutting threads, which may be separated by flutes, wherein, upon rotation of the awl-tap member, the cutting threads are configured to cut the interior surface of the hole to thereby form the female portion of a mating pair (i.e., create the internal threading within pedicle for threaded engagement with corresponding external threading of bone screw).

Accordingly, in certain embodiments, the handheld device further includes a ratchet assembly that rotatably couples the handle and the awl-tap member to one another. The ratchet assembly provides ratcheting action which results in the awl-tap member advancing into or withdrawing from bone during hole formation. For example, the ratchet assembly includes a switch allowing a user to toggle between a first rotation setting and a second rotation setting. In the first rotation setting, rotation of the handle in a first direction results in the awl-tap member rotating in the same direction while rotation of the handle in an opposite second direction is independent of any rotation of the awl-tap member (i.e., the awl-tap member remains stationary). In the second rotation setting, rotation of the handle in the first direction is independent of any rotation of the awl-tap member (i.e., the awl-tap member remains stationary) while rotation of the handle in the opposite second direction results in the awl-tap member rotating in the same direction.

Accordingly, when using the handheld device having a ratchet assembly, the surgeon may form a hole in bone, and perform various neurostimulation and/or neuromonitoring functions, without concern over any related cables or wires (for use in the neurostimulation and/or neuromonitoring functions) becoming entangled around the handheld device as the handle is rotated. Essentially, the ratchet assembly allows the handle to remain relatively stationary as various functions involving rotating the handle are performed.

In some embodiments, the awl-tap member may be cannulated (i.e., hollow) and be configured to receive a medical tool or accessory therethrough, such as, for example, a probe, a stylet, a guidewire, or the like. For example, a stylet may be positioned within a lumen of the awl-tap member to prevent bone debris or other tissues from entering the lumen as the distal tip of the awl-tap member is advanced into bone. The stylet may be coupled to an anvil at a proximal end, which facilitates inserting and removing the stylet from the lumen. At least a proximal end of the awl-tap member is retained within the handle via a ball lock assembly. In some embodiments, the ball lock assembly provides a user with the ability to lock the awl-tap member in place to remain coupled to the handle during a procedure and unlock the awl-tap member, thereby disengaging the awl-tap member from the handle to allow removal of the awl-tap member if desired. Accordingly, the handle may be configured to receive one of a plurality of different awl-tap members, each releasably couplable to the handle and interchangeable with one another. In particular, the handle is able to be equipped with any one of a plurality of interchangeable awl-tap members as the surgeon sees fit, which is particularly beneficial as each awl-tap member may have a specific length, diameter, penetration member configuration, and other qualities that may be useful for any particular procedure.

As previously described, the body of the awl-tap member is electrically conductive and is operable to carry electrical current for neurostimulation and neuromonitoring functions. Accordingly, the handheld device can provide neuromonitoring functionality during penetration into the bone via the awl-tap member, which, in turn, provides real-time, or near real-time, alerts to the surgeon as to the presence of any nearby nerves that may be in the path of a screw, or otherwise affected, when a screw is placed within the hole. The neuromonitoring feedback can facilitate repositioning of the handheld device, particularly the penetrating distal tip of the awl-tap member, if there is any sensing of nearby nerves, thereby ensuring a properly formed hole and subsequently ensuring proper positioning of a screw within the hole so as to avoid inadvertent piercing, breaching, damage, or impinging upon unintended structures or tissues. The neuromonitoring feedback can also inform the determination of electrical parameters used for neurostimulation of nerves adjacent to the hole.

To perform at least the neurostimulation and neuromonitoring functions, the handheld device may be coupled to and placed in electrical connection with an input connector of a neuromonitoring device via a cable. The neuromonitoring device may include a junction box configured to carry electrical signals to and from the input connector and the handheld device. The junction box includes a processor configured to generate and transmit electrical signals to and from the input connector, and the handheld device. For example, in some embodiments, the processor may be configured to generate and transmit a pulse of electrical current to the awl-tap member, while positioned within a hole, to perform neuromonitoring of nerves adjacent or in close proximity to the hole. In addition, certain electrodes inserted into muscles of the patient may be used to detect a current flow from the awl-tap member to an electrode, indicating a completed circuit between the awl-tap member and the electrode, wherein such current flow is indicative of the presence of a nerve adjacent to the hole by detecting electrical activity at a muscle enervated by the nerve stimulated by the awl-tap member. The processor of the junction box is operably connected to the input connector, electrode inputs, and one or more PCBs. The one or more PCBs may include a pulse or current generating circuit configured to generate and transmit electrical current to the handheld device, a current generating confirmation circuit configured to detect electrical current delivered from the device to nerves, a muscle movement detection circuit configured to detect muscle movement in response to neurostimulation or neuromonitoring functions, and an electrode disconnection detection circuit configured to detect partial or total disconnection of an electrode from the junction box or the patient, or improper insertion of an electrode into the patient.

As previously described, the handheld device provides a depth measurement function in which a depth of the hole formed via the awl-tap member is measured in real-time (i.e., as the awl-tap member advances into bone) via the depth sleeve member and depth measurement sensor operably associated with the depth sleeve member.

The depth sleeve member comprises an elongate hollow body including a proximal end operably associated with the handle and an opposing distal end extending from the handle. The elongate hollow body includes a lumen extending entirely therethrough, in which at least a portion of an awl-tap member is received when the awl-tap member is coupled to the handle. The depth sleeve member and awl-tap member are configured to move independent of one another. Furthermore, the depth sleeve member is configured to move relative to the handle. For example, in some embodiments, the handheld device further includes a sleeve spring that applies a biasing force upon a portion of the depth sleeve member at or near the proximal end such that the depth sleeve member is biased in a direction away from the handle when in a default position. The distal end of the depth sleeve member is shaped and/or sized to engage an exterior surface of the bone along a periphery of an opening of a hole to be formed via the awl-tap member. Accordingly, upon engagement between the distal end of the depth sleeve member and the exterior surface of the bone, a user can advance the distal tip of the awl-tap member of the handheld device (via twisting the handle with the aid of the ratchet assembly) to begin forming the hole. As the distal tip of the awl-tap member is drawn into the bone and begins forming a hole, the handle is correspondingly drawn in a direction towards the bone. While both the awl-tap member and handle are drawn in a direction towards the bone as the hole is formed, the distal end of the depth sleeve member remains in contact with the exterior surface of the bone along the periphery of the opening of the hole and is essentially pushed in an opposing direction toward the handle, such that the portion of the depth sleeve member at or near the proximal end pushes upon the sleeve spring, thereby compressing the sleeve spring. The sensor senses the movement of the depth sleeve member relative to the awl-tap member and handle, and generates a signal indicative of a depth of a hole created by the awl-tap member based on the detected movement. In other words, the sensor sense movement of the depth sleeve member relative to at least the distal tip of the awl-tap member as the awl-tap member is drawn further into bone during formation of the hole and the depth sleeve member moves from its default, extended position to a retracted position. The sensor is in communication with depth gauge electronics and/or circuitry provided on a printed circuit board (PCB) enclosed within the handle.

In some embodiments, the handheld device further includes a digital display provided on the handle and configured to visually provide a digital readout of a depth measurement of the hole based on the electronic signal from the sensor. In other embodiments, the handheld device may be configured to wirelessly communicate and exchange data with a separate display or computing device, such as, for example, a monitor or panel display, a PC, a notebook, a tablet computer, a smartphone, or other wireless computing device.

As previously described, the handheld device may include a cannulated awl-tap member. Accordingly, in certain embodiments, the awl-tap member is configured to receive a guidewire having a deployable distal hook member configured to securely anchor into a desired position relative to a hole formed in bone. The distal hook member is configured to transition between a delivery configuration, in which the distal hook member can be positioned within and move through a drilled hole to a desired position, and a deployed configuration, in which the distal hook member is configured to anchor into place, either within the hole (e.g., at the base of a mono-cortical hole) or outside of the hole (e.g., on opposing side of a bicortical drilled hole). The guidewire is configured to assist in the placement of the screw(s) and/or implant(s). For example, the guidewire may be compatible with the handheld device consistent with the present disclosure. In particular, the guidewire, when the hook member is in the delivery configuration, may be inserted into the lumen of the awl-tap member and may translate along the length of the awl-tap member. Accordingly, once the hole is formed, the hook member may be extended out of the awl-tap member distal tip and then anchored into place (i.e., either at the base of the hole or on the opposing side of bone in a bicortical drilled hole). The awl-tap member may then be removed from the handle, at which point a cannulated screw may be loaded onto the guidewire and slid down the guidewire and into alignment with the hole. Accordingly, the guidewire provides improved stability during a screw placement procedure, as the guidewire essentially acts as a guide for the screw to slide along when a surgeon is placing the screw.

Accordingly, the handheld device of the present disclosure allows a surgeon to form a hole for a bone fixation procedure, perform and control neurostimulation and neuromonitoring functions during hole formation to ensure accuracy and safety during hole formation, and further measure a depth of the hole, all in a sterile environment and through use of a single device. The surgeon may perform all such aspects of the bone fixation procedure while receiving real-time or near real-time digital feedback on a display of the handheld device.

BRIEF DESCRIPTION OF THE DRAWINGS

Features and advantages of the claimed subjects matter will be apparent from the following detailed description of embodiments consistent therewith, which description should be considered with reference to the accompanying drawings, wherein:

FIG. 2 is a side view of the guidewire assembly of FIG. 1;

FIG. 3 is a side cross-sectional view of the guidewire assembly taken along lines A-A of FIG. 2;

FIG. 5 is a side view of the guidewire assembly of FIG. 4;

FIG. 6 is a side cross-sectional view of the guidewire assembly taken along lines B-B of FIG. 5;

FIGS. 7A and 7B are perspective views of the guidewire assembly illustrating the transition of the distal hook member from the delivery configuration (FIG. 7A) to the deployed configuration (FIG. 7B);

FIGS. 10A and 10B are side views of an assembled surgical depth instrument consistent with the present disclosure illustrating movement of the needle or probe from a starting position (FIG. 10A) to an extended position (FIG. 10B) for measurement of a hole depth;

FIGS. 11A and 11B are side cross-sectional views of the assembled surgical depth instrument taken along lines C-C of FIGS. 10A and 10B, respectively;

FIGS. 20A and 20B are enlarged cross-sectional views of the handheld device of FIG. 16 illustrating transitioning of the ball lock assembly between locked and unlocked positions, respectively;

FIGS. 22A and 22B are cross-sectional views of the handheld device of FIG. 16 illustrating different positions of the sleeve member relative to the housing which is used in determining the depth of a drilled hole;

FIGS. 31A-31H illustrate a series of steps for performing a procedure of deploying the hook member of the guidewire and subsequently obtaining a depth measurement using a surgical depth instrument consistent with the present disclosure;

FIGS. 32A-32D illustrate a series of steps for transitioning the hook member from the deployed configuration to the delivery configuration to allow for retraction of the hook member back into the drilled hole and subsequently utilizing the guidewire and hook member, particularly the plurality of struts or splines of the hook member, to carry electrical current to and from a nerve sensing/nerve stimulation device for neuromonitoring purposes;

FIGS. 33A and 33B are schematic illustrations of a system for a bone implant fixation procedure including a neuromonitoring device and a handheld device consistent with the present disclosure;

Figure 1:
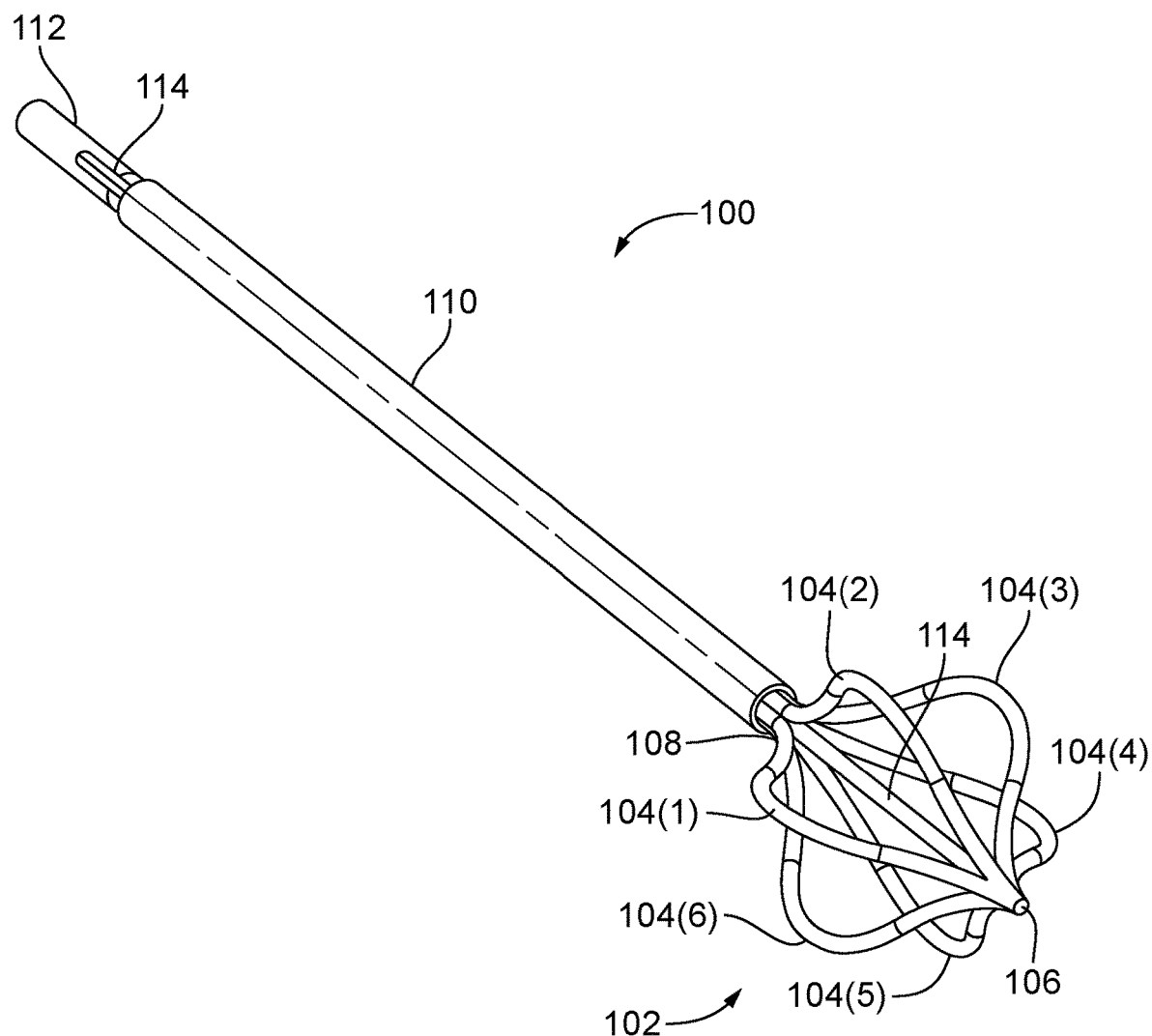
FIG. 1 is a perspective view of one embodiment of a guidewire assembly of the minimally invasive surgical depth instrument consistent with the present disclosure, illustrating the distal hook member in the delivery configuration.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to a system including a handheld device for use in open or minimally invasive surgical procedures, such as a bone implant fixation procedure. The handheld device may be used in any bone implant fixation procedure, including, for example, percutaneous pedicle screw fixation, which may include, but is not limited to, anterior lumbar interbody fusion, lateral interbody fusion, and posterior lumber interbody fusion or transforaminal lumbar interbody fusion. It should be further noted that, while the following description describes use of the handheld device in minimally invasive surgical procedures, the disclosed handheld device is designed for use in an open surgical procedure, alternatively or in addition to minimally invasive procedures.

The handheld device is configured to perform various functions during a bone implant fixation procedure. In particular, a handheld device consistent with the present disclosure is configured to perform at least one of: penetration of a bone to form a hole or opening for receipt of a screw; neuromonitoring, in cooperation with a neuromonitoring device, of the hole during, or post-, formation of the hole so as to sense any nearby nerves adjacent to the hole that may be in the path of a screw, or otherwise affected, when a screw is placed within the hole; neurostimulation, in cooperation with a neuromonitoring device, of nerves adjacent to the hole during, or post-, formation of the hole; and measuring of a depth of the hole and providing a digital measurement of the depth to assist the surgeon in selecting the appropriate length of screw.

The handheld device generally includes a handle including a grip portion providing a surgeon or other medical professional with a means to manipulate the device and components thereof. The handheld device further includes an awl-tap member releasably coupled to the handle and configured to penetrate bone upon manipulation of the grip portion, a depth sleeve member operably associated with the handle and configured to move relative thereto, the depth sleeve member including an elongate body including a lumen extending therethrough within which a portion of the awl-tap member is received, and a sensor operably associated with the sleeve member and configured to detect movement of the sleeve member relative to the awl-tap member and generate an electronic signal indicative of a depth of a hole created by the awl-tap member based on the detected movement.

The handheld device provides an improved manner in which a hole or opening is formed in bone by providing neuromonitoring functionality during penetration into the bone, which, in turn, provides real-time, or near real-time, alerts to the surgeon as to the presence of any nearby nerves that may be in the path of a screw, or otherwise affected, when a screw is placed within the hole. This real-time or near real-time feedback may be provided to the surgeon visually (i.e., via a digital display, such as a display screen, or via a light source, such as an LED array) and/or audibly (i.e., via a speaker). The neuromonitoring feedback can facilitate repositioning of the handheld device, particularly a penetration member of the device, if there is any sensing of nearby nerves, thereby ensuring a properly formed hole and subsequently ensuring proper positioning of a screw within the hole so as to avoid inadvertent piercing, breaching, damage, or impinging upon unintended structures or tissues. The handheld device further allows for accurate measurements of the depth of a formed hole and provides a digital display of the depth measurement, thereby providing the surgeon with a quick and accurate reading upon which they rely when selecting the appropriate length screw (ensuring they do not select a screw that is either too short or too long).

The handheld device further provides neurostimulation functionality during penetration into the bone to form a hole or post formation of the hole. For example, the handheld device may be used for neuromonitoring functions to determine the presence of nerves adjacent or in close proximity to the hole prior to placement of a screw into the hole, and nerves that are present and adjacent to the hole may then be stimulated by electrical current carried to the handheld device. The handheld device may generate the electrical current from a source incorporated into the handheld device itself or the handheld device may be coupled to and placed in electrical connection with an input connector of a neuromonitoring device that provides pulses of electrical current to the handheld device for the neurostimulation and neuromonitoring features described herein.

In certain embodiments, the awl-tap member is configured to receive a guidewire having a deployable distal hook member configured to securely anchor into a desired position relative to a hole formed in bone. In particular, the awl-tap member may be cannulated (i.e., hollow) and thus include a lumen extending entirely therethrough. As such, the guidewire may be fed into and through the lumen of the awl-tap member. The distal hook member of the guidewire is configured to transition between a delivery configuration, in which the distal hook member can be positioned within and move through a drilled hole to a desired position, and a deployed configuration, in which the distal hook member is configured to anchor into place, either within the hole (e.g., at the base of a mono-cortical hole) or outside of the hole (e.g., on opposing side of a bicortical drilled hole). The guidewire is configured to assist in the placement of the screw(s) and/or implant(s). For example, the guidewire may be compatible with the handheld device consistent with the present disclosure. In particular, the guidewire, when the hook member is in the delivery configuration, may be inserted into the lumen of the awl-tap member and may translate along the length of the awl-tap member. Accordingly, once the hole is formed, the hook member may be extended out of the awl-tap member distal tip and then anchored into place (i.e., either at the base of the hole or on the opposing side of bone in a bicortical drilled hole). The awl-tap member may then be removed from the handle, at which point a cannulated screw may be loaded onto the guidewire and slid down the guidewire and into alignment with the hole. Accordingly, the guidewire provides improved stability during a screw placement procedure, as the guidewire essentially acts as a guide for the screw to slide along when a surgeon is placing the screw.

Accordingly, the handheld device of the present disclosure allows a surgeon to form a hole for a bone fixation procedure, perform and control neurostimulation and neuromonitoring functions during hole formation to ensure accuracy and safety during hole formation, and further measure a depth of the hole, all in a sterile environment and through use of a single device. The surgeon may perform all such aspects of the bone fixation procedure while receiving real-time or near real-time digital feedback on a display of the handheld device.

The following description relates to exemplary embodiments of guidewire assemblies, surgical depth instruments, and handheld devices for use in a minimally invasive surgical procedure, such as a bone implant fixation procedure. Each of the described guidewire assemblies, surgical depth instruments, and variations of handheld devices may be used in a system described herein.

FIG. 1 is perspective view of one embodiment of a guidewire assembly 100 consistent with the present disclosure. FIG. 2 is a side view of the guidewire assembly 100 and FIG. 3 is a side cross-sectional view of the guidewire assembly 100 taken along lines A-A of FIG. 2. The guidewire assembly 100 generally includes a deployable hook member 102 at a distal end of the guidewire 100. The distal hook member 102 includes a plurality of struts or splines 104(1)-104(6), each of which includes a distal end fixedly coupled to a distal-most end 106 of the guidewire 100 and a proximal end fixedly coupled to a portion of the guidewire body 108 positioned a distance from the distal-most end 106. Accordingly, the plurality of struts 106 share common fixation points at their respective distal and proximal ends to form a basket-like or mushroom-like structure.

The plurality of struts 104 may be made of a resilient, biologically inert material, such as NITINOL metal, stainless steel, or silicone rubber, for example, and may be arranged either symmetrically or asymmetrically about a longitudinal axis of the hook member 102. Although shown with a total of six struts 104(1), 104(2), 104(3), 104(4), 104(5), and 104(6), it should be noted that a hook member 102 consistent with the present disclosure may include more or less than six struts and is thus not limited to any number of struts.

Figure 4:
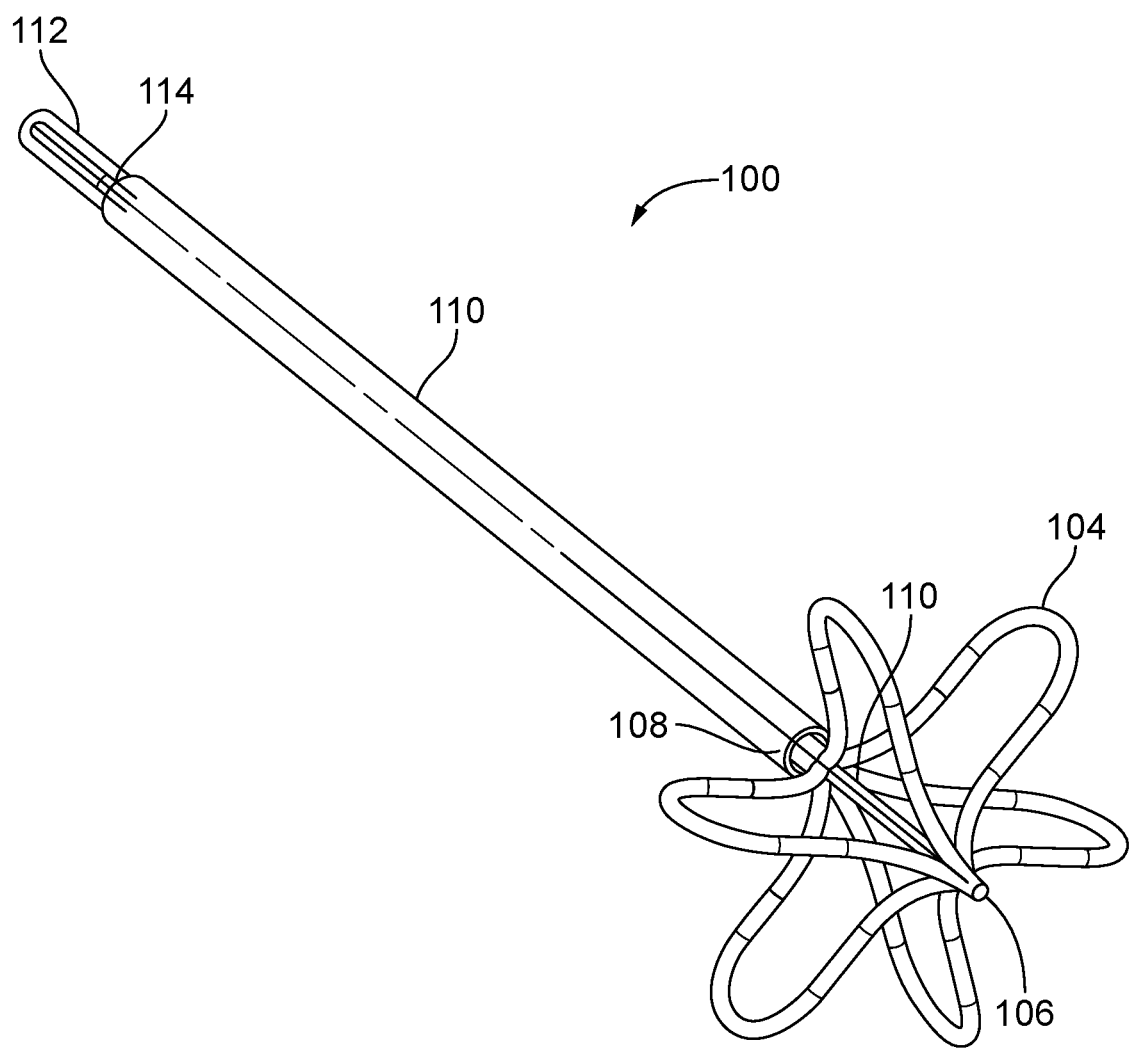
FIG. 4 is perspective view of the guidewire assembly illustrating the distal hook member in the deployed configuration.

The hook member 102 is configured to transition between a delivery configuration, as illustrated in FIGS. 1-3, and a deployed configuration, as shown in FIGS. 4-6. In particular, guidewire assembly 100 may further include a guide tube or cover 110 configured to provide rigidity to the guidewire 100 during positioning in a drilled hole, a pull rod 112, and a pull-wire 114 coupled to the pull rod 112 and coupled to the distal-most end 106 of the guidewire 100. The pull rod 112 and pull-wire 114 are configured to assist the hook member 102 from transitioning between the delivery and deployed configurations. For example, when in the default state (i.e., no application of pulling force upon the pull-rod 112 and pull-wire 114), the hook member 102 may remain in a delivery configuration, in which the hook member 102 has a relatively compact size and has a first diameter $D_1$. When in the delivery configuration and due to its compact size, the hook member 102 may be freely positioned within and move through a drilled hole or other passage to a desired position. Due to the resilient nature of the material from which the struts are made from, the hook member 102 may be pushed into a drilled hole until reaching a desired position (i.e., either the bottom of the hole or entirely through the hole if a bicortical drill hole).

Upon reaching the desired position, a user (i.e., surgeon or other medical professional) need only apply a pulling force upon the pull-wire 114 (i.e., pull the pull rod 112), which, in turn, results in retraction of the distal-most end 106 of the guidewire 100, thereby causing the distal end of each of the plurality of struts 104 coupled thereto to move towards the opposing proximal end of each strut and cause the hook member 102 to expand in diameter and thereby transition to the deployed configuration, as shown in FIGS. 4-6. For example, when in the deployed configuration, the hook member 102 has a second diameter $D_2$ which is greater than the first diameter $D_1$ when the hook member 102 is in the delivery configuration.

FIGS. 7A and 7B are perspective views of the guidewire 100 illustrating the transition of the hook member 102 from the delivery configuration (FIG. 7A) to the deployed configuration (FIG. 7B). The expansion in diameter of the hook member 102 results in anchoring of the hook member 102 in a desired position. When in the deployed configuration, the hook member 102 is configured to anchor into place, either within the hole (e.g., at the base of a mono-cortical hole) or outside of the hole (e.g., on opposing side of a bicortical drilled hole). For example, if the hook member 102 is transitioned to the deployed configuration within the drilled hole, the expanded diameter causes the struts 104 to engage interior walls of the drilled hole, thereby lodging the hook member 102 within. In some procedures in which a plate or implant is to be secured with screws through a bicortical drill hole, the distal hook member may be advanced entirely through the hole (from one side of the bone to the other), at which point the surgeon may then transition the hook member to the deployed configuration, in which the expanded diameter is much greater than the drilled hole diameter and opening, and thus the user need only pull back on the guidewire 100 until the expanded hook member 102 securely engages the exterior surface of the bone adjacent to the drilled hole. Due to the resilient nature of the material of the struts, the hook member may essentially flatten against the surface of the bone upon a user pulling back on the guidewire, wherein such flattening may enhance tactile feel, providing the user with an indication that the hook member is sufficiently anchored. The user can maintain the tension on the pull-wire 114 by simply winding a portion of the pull-wire 114 around the pull rod 112 and subsequently reestablishing a connection between the pull rod 112 and the need only position the pull rod 112 in the guide tube or cover 114, as shown in FIGS. 5 and 6. When the user wishes to disengage the hook member 102 from an anchored position, they need only release the tension on the pull-wire 114 and the struts 104 will return to their default shape, thereby returning the hook member 102 to the delivery configuration, at which point the guidewire 100 can be removed.

The guidewire 100 is configured to assist in depth measurement procedures, as well as the placement of the screw(s) and/or implant(s). For example, the guidewire may be compatible with a variety of separate medical instruments, which may include measuring devices for determining the depth of the hole, as well as other medical instruments used in a bone implant fixation procedure, such as tools for the placement of the screw(s) and/or implant(s).

Figure 8:
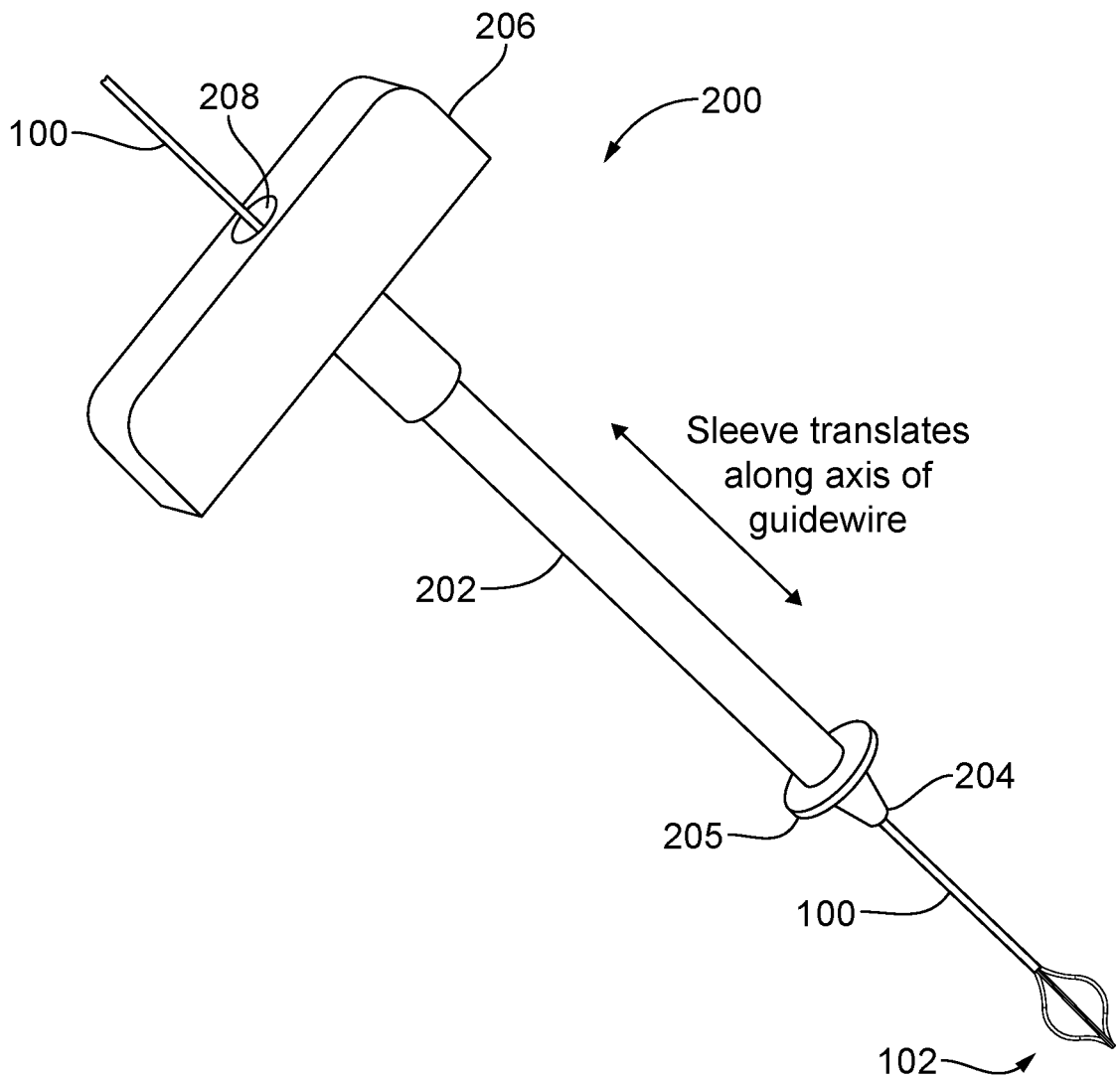
FIG. 8 is a perspective view of a sleeve member of a surgical depth instrument consistent with the present disclosure, illustrating a sleeve member of the surgical depth instrument slidably mounted to the guidewire assembly.

For example, an exemplary measuring or surgical depth instrument may include a sleeve member 200 and a needle or probe member 300 compatible for use with the guidewire 100. FIG. 8 is a perspective view of the sleeve member 200 slidably mounted to the guidewire 100 and FIG. 9 is a perspective view of the needle or probe member 300 of the surgical depth instrument relative to the corresponding sleeve member 200.

As shown, the sleeve member 200 generally includes an elongate body 202, which may serve as a handle for the user during a procedure, wherein the body 202 has a distal end 204 and a proximal end 206, as well as a bore 208 extending entirely through the body 202 from the distal end 204 to the proximal end 206. The bore 208 is shaped and/or sized to receive the guidewire body therein. Accordingly, the sleeve member 200 may be slid onto the guidewire 100, by way of the bore 208, and may thereby translate along a length of the guidewire 100, either during positioning and anchoring of the distal hook member 102 or once the distal hook member 102 is deployed and anchored in position. As will be described in greater detail herein, the distal end 204 of the sleeve member 200 is configured to engage at least an opening of a drilled hole during a procedure and a flanged member 205 generally serves as a abutting feature for engaging the exterior surface of the bone along a periphery of the hole opening.

Figure 9:
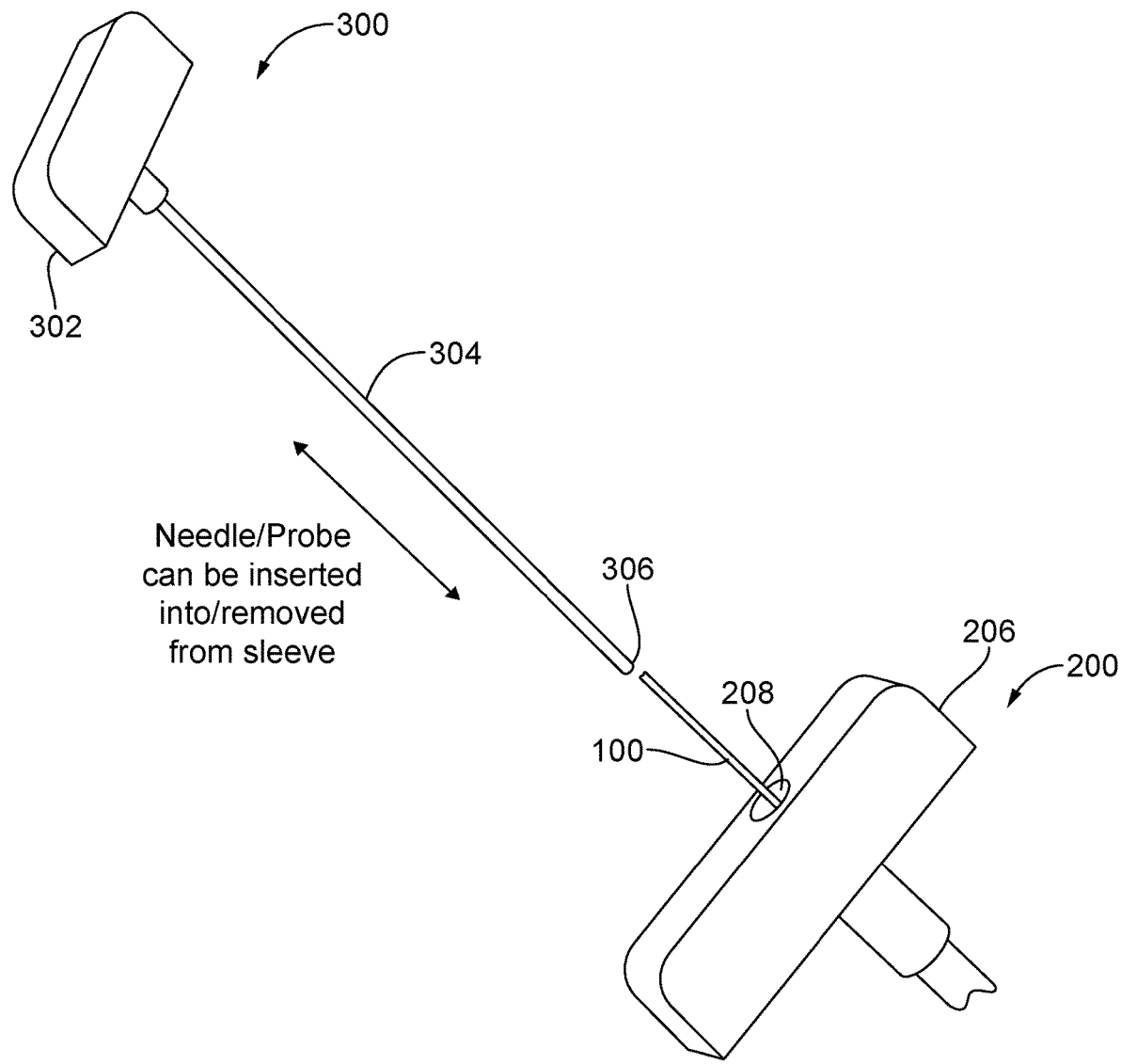
FIG. 9 is a perspective view of the needle or probe member of the surgical depth instrument relative to the corresponding sleeve member.

The surgical depth instrument may further include a needle or probe 300, illustrated in FIG. 9. The needle or probe 300 includes a handle 302, an elongate body 304 extending from the handle 302, and a distal tip 306. For sake of clarity and ease of description, the needle or probe 300 is hereinafter referred to as "probe 300". The probe 300 is configured to be slidably mounted within the sleeve member 200, by way of the bore 208. For example, the bore 208 of the sleeve member 200 may be shaped and/or sized to accommodate both the guidewire 100 and the probe 300. Yet still, in other embodiments, the probe 300 may be hollow, such that the probe 300 may receive the guidewire 100 within, thereby allowing for the probe 300 to translate along a length of the guidewire 100 and further slide along a length of the sleeve member 200.

Accordingly, once the hook member 102 is anchored in place, the guidewire 100 provides improved stability during a depth measurement procedure and/or screw placement procedure, as the guidewire 100 essentially acts as a guide for the sleeve member 200 and/or probe 300 to slide along a length thereof. Furthermore, the hook member 100 provides an accurate datum from which the depth of the hole can be determined, thereby improving the precision with which depths of holes can be determined.

For example, upon establishing an anchored position with the hook member 102, a user need only slide the sleeve member 200 towards the drilled hole until a distal-most end 204 of the sleeve member 200, which is tapered, engages the opening of the hole and establishes engagement and maintains the sleeve member 200 in a stabilized position, at which point, the probe 300 can be used for measuring the depth of the hole. In some embodiments, the distal end 204 may further include edges or prongs that, upon rotation of the sleeve member 200, can stick into the interior surface of the hole and thereby further establish purchase with the bone and prevent inadvertent dislodging from the hole. In order to remove the sleeve member, the user need only rotate the sleeve member in the opposite direction, which will release the edges or prongs from engagement.

FIGS. 10A and 10B are side views of the sleeve member 200 and probe 300 assembled with one another illustrating movement of the needle or probe from a starting position (FIG. 10A) to an extended position (FIG. 10B) for measurement of a hole depth. FIGS. 11A and 11B are side cross-sectional views of the sleeve member 200 and probe 300 assembled with one another taken along lines C-C of FIGS. 10A and 10B, respectively. The surgical depth instrument further includes at least one sensor configured to generate an electronic signal indicative of a depth of the hole as a result of sensing a distance of movement of the probe 300 into the drilled hole. For example, as will be described in greater detail herein, a surgeon need only advance the probe 300 into the hole until they establish engagement between the distal tip 306 of the probe 300 with the anchored hook member 102. Again, the guidewire 100 essentially acts as a guide upon which the probe 300 may either slide over, or slide alongside, when advancing to the anchored hook member 102, which provides the datum from which the depth of the hole is determined.

The sensor is configured to generate an electronic signal based on a distance of movement of the probe 300, wherein the electronic signal is indicative of at least a depth of the hole. In particular, the sensor may include inductive or capacitive elements or assemblies configured to sense the location of the distal tip 306 of the probe 300 relative to a distal end 204 of the sleeve member 200, and, as a result, generate an electronic signal representing the distance there between. Accordingly, the sensed distance between the distal end 204 of the sleeve member 200 (when abutting the bone surface) and the distal tip of the probe member (when abutting the anchored hook member) is the depth of the hole.

Figure 12:
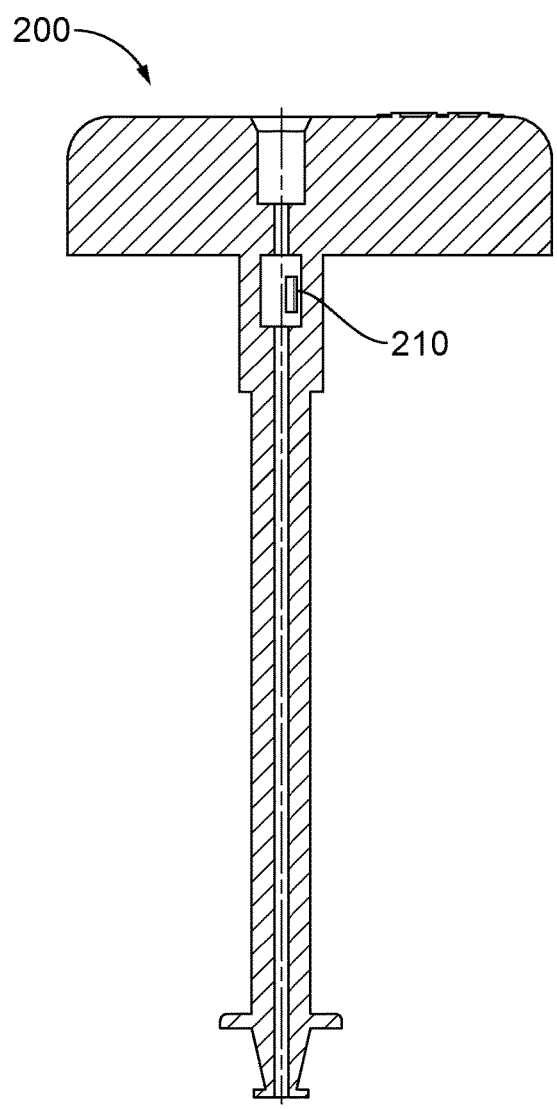
FIGS. 12 and 13 are cross-sectional views of the sleeve member illustrating different sensor systems/arrangements for determining depth of a drilled hole.
Figure 13:
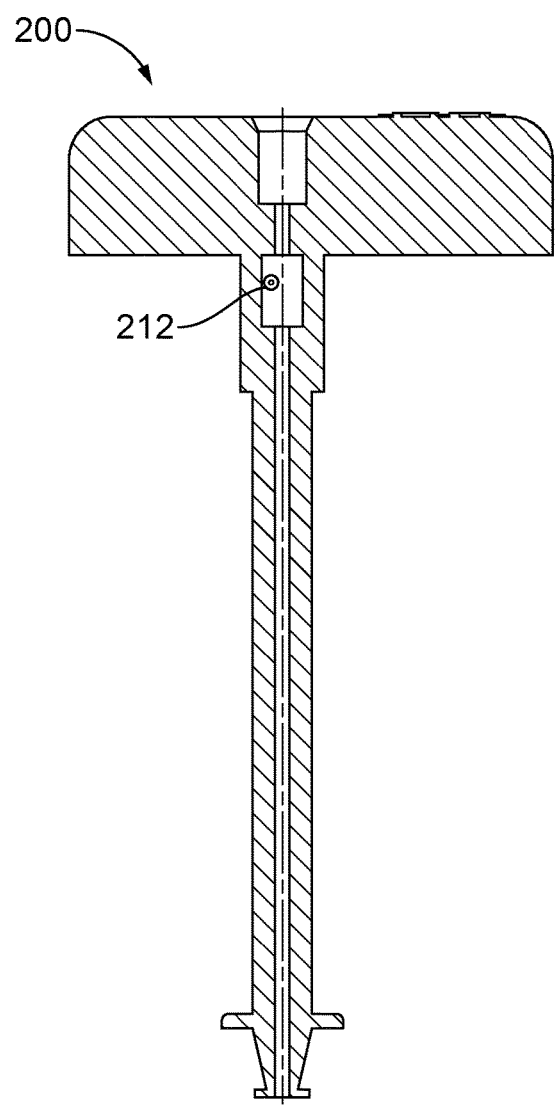

FIGS. 12 and 13 are cross-sectional views of the sleeve member 200 illustrating different sensor systems/arrangements for determining depth of a drilled hole based on movement of the probe 300. In some embodiments, the sensor system may include a potentiometer 210 arrangement (FIG. 12). In some embodiments, as shown in FIG. 13, the sensor system for determining depth may include a worm gear measurement system, wherein the sleeve member 200 may include a pinion gear 212 and the probe may have a corresponding worm gear configuration on its exterior surface. Yet still, in some embodiments, the sensor system may include a laser diode configured to read or otherwise sense machine-readable markings on the probe to determine distance traveled when determining/calculating depth of the drilled hole.

It should be noted that the surgical instrument may include logic or allow for adjustment to the sensing capabilities so as to program the sensor to account for other variables when sensing the depth of the hole. For example, in some embodiments, certain procedures require fixing a plate or implant to the bone via screws. Accordingly, the screw length must not only be sufficient to fill the hole but also long enough to account for the thickness of a plate or implant through which it passes when engaging the hole. Accordingly, in some embodiments, the sensor may be programmed so as to account for the thickness of the plate or implant and will further include that thickness in the electronic signal produced, such that the electronic signal is indicative of the total depth that a corresponding screw length will need to cover, including the depth of the hole in the bone in addition to the thickness of the plate or implant through which the screw will pass through and the screw head will engage.

Accordingly, the digital sensing of the hole depth provides a much more accurate measurement than conventional analog depth gauges and also requiring very little, if any, input or interpretation from the surgeon. Accordingly, by providing a much more accurate measurement of a hole depth, the surgeon is able to select the correct length screw for any given hole so as to improve the chances of a successful surgery.

In some embodiments, the surgical instrument may further include a display provided on the sleeve member 200, for example, and may be configured to visually provide a digital readout of a depth measurement of the hole based on the electronic signal from the sensor. In other embodiments, the surgical depth instrument may be configured to wirelessly communicate and exchange data with a separate display or computing device, such as, for example, a monitor or panel display, a PC, a notebook, a tablet computer, a smartphone, or other wireless computing device.

Upon receiving the electronic signal from the sensor, the separate display or computing device may be configured to visually provide the depth measurement of the hole based on the electronic signal from the sensor. Furthermore, in some embodiments, the computing device may include a specific software application that may be directed to maintaining a record of the hole measurements and/or provide an interactive user interface in which multiple holes can be mapped to a particular plate or implant and the depth of each hole (including the thickness of the plate or implant) can be included and stored for records.

Figure 14:
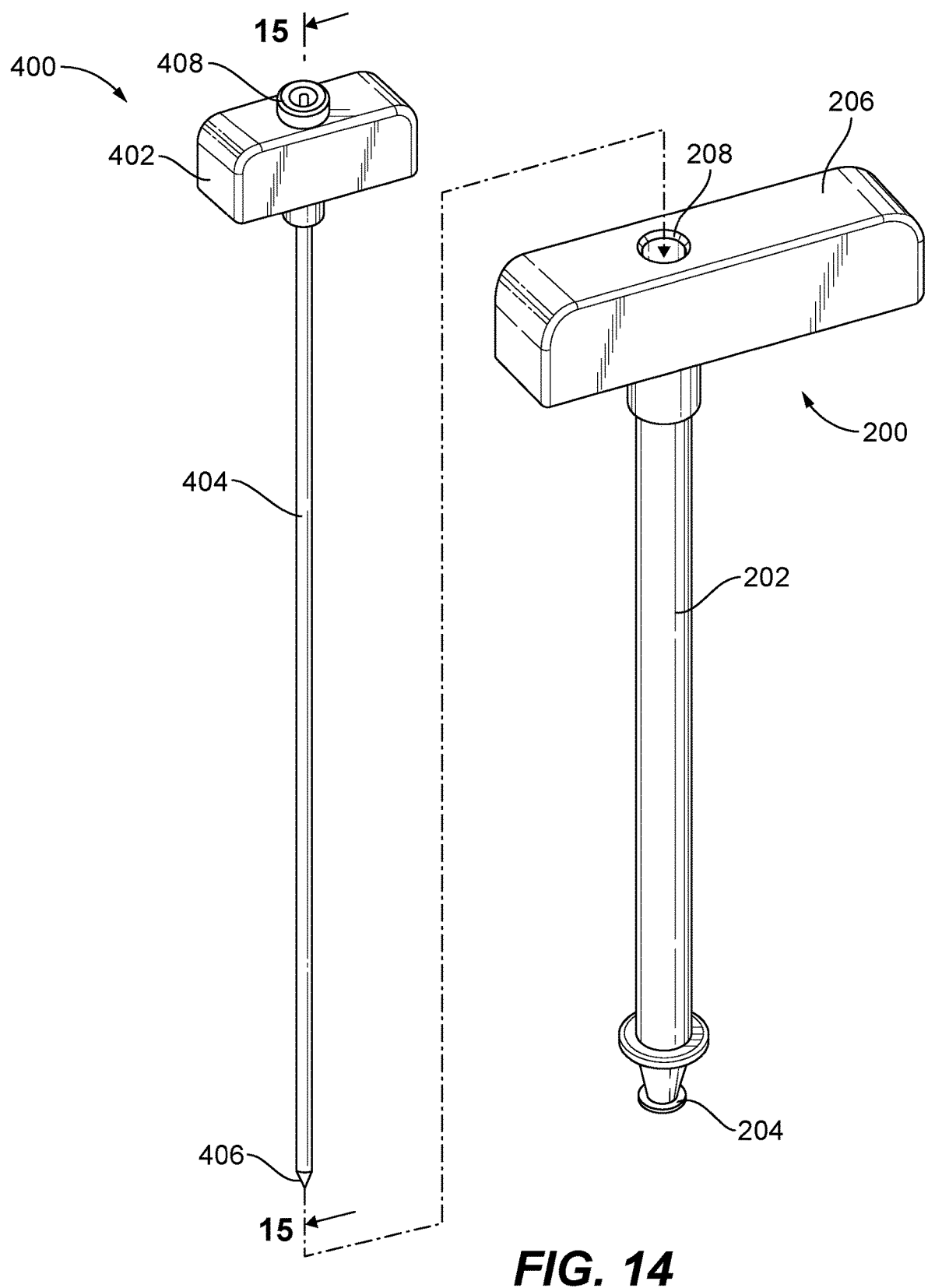
FIG. 14 is a perspective view of another embodiment of a probe, generally resembling an awl, relative to the sleeve member and compatible therewith.

FIG. 14 is a perspective view of another embodiment of a probe 400 consistent with the present disclosure and compatible with the sleeve member 200. As shown, the probe 400 generally resembles an awl and is configured to pierce tissue, including soft bone tissue, such as the soft bone tissue in the vertebrae, to thereby form a hole into which a screw or other fixing device is to be placed. The probe 400 includes a handle 402, an elongate body or shaft 404 extending from the handle 402, and a distal tip 406. The tip 406 may be sufficiently rigid and include an edge or point sufficient to engage and pierce bone and create a pathway (i.e., bore) into which a screw or other fixing device is to be placed. In this embodiment, the probe 400 is configured to be slidably mounted within the sleeve member 200, by way of the bore 208, in which the sleeve member 200 may provide a surgeon with sufficient rigidity and stability with one hand while the surgeon utilizes their other hand for manipulating the probe 400 so as to pierce the desired target area, whereby the sleeve member 200 may generally act as a guide of sorts.

In addition to penetrating tissue and bone, the probe 400 may further be utilized for neuromonitoring purposes (i.e., sensing any nearby nerves adjacent to the bore that may be in the path of a screw, or otherwise affected, when a screw is placed within the bore and thereby prevent unintended nerve pain and/or damage). In particular, the probe 400 may be configured to be coupled to a separate neuromonitoring apparatus, such as a nerve sensing/nerve stimulation device or system 600, such as existing capital equipment or a battery-powered neuromonitoring device, for example. As illustrated in FIG. 14, the probe 400 may include a coupling member 408 for electrically coupling a portion of the probe 400, specifically an inner core or wire 410 (shown in FIG. 15), with a connector of the nerve sensing device 600, generally in a male-female coupling arrangement.

Figure 15:
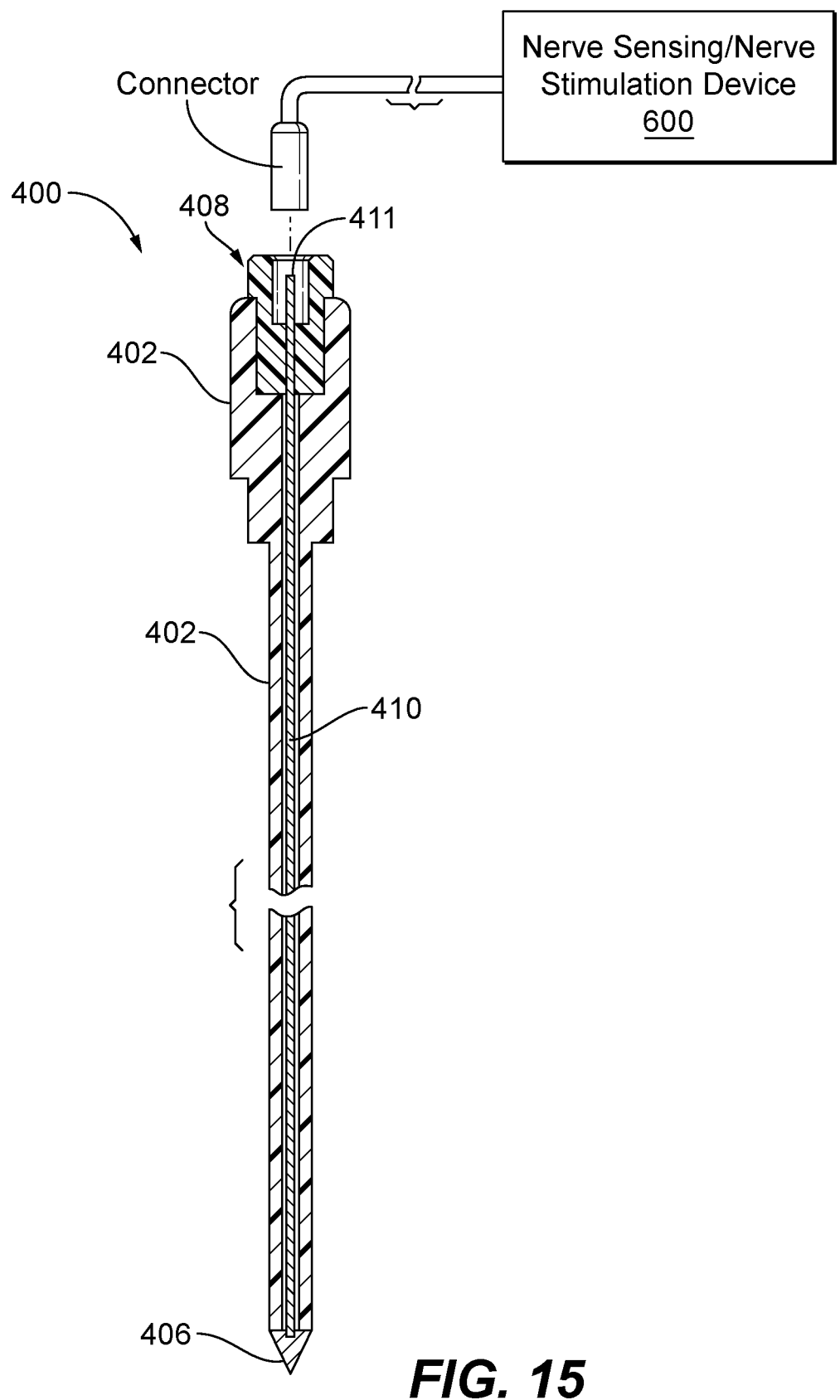
FIG. 15 is a side cross-sectional view of the needle member taken along lines 15-15 of FIG. 14 and illustrating an internal configuration of the probe, specifically an internal conductive core or wire configured to carry electrical current to and from a nerve sensing/nerve stimulation device to provide at least neuromonitoring features.

FIG. 15 is a side cross-sectional view of the probe 400 taken along lines 15-15 of FIG. 14 and illustrating the internal configuration of the probe 400, specifically an internal conductive core 410 configured to carry electrical current to and from a nerve sensing/nerve stimulation device or system 600 to provide at least neuromonitoring features. As shown, the body or shaft 404 of the probe 400 may include an electrically conductive core 410 that extends the length of the shaft 404 from the handle 402 through to the tip 406. Accordingly, the shaft 404 generally functions as an outer casing, surrounding the inner core 410, which may be in the form of a wire, for example. The core 410 may include a proximal end 411 that is exposed within the coupling member 408 and is electrically coupled to the nerve sensing/ nerve stimulation device or system 600 when the connector is engaged with the coupling member 408. The inner core or wire 410 may include an electrically conductive material configured to act as an extension to the nerve sensing/ stimulation device 600 and may be used to sense/stimulate nerves within or adjacent to the bone. The inner core or wire 410 may include an electrically conductive material (e.g., a metal such as stainless steel, nitinol, or aluminum, or other electrically conductive material) and thus may carry an electrical current. In some embodiments, the inner core or wire 410 may include a polyether ether ketone (PEEK) material. In some embodiments, the inner core or wire 410 may include a graphite material. The shaft 404 may include a polygon composite material, such as POLYMED composite tubing offered by Polygon Company (Walkerton, Ind.). The polygon composite material may essentially act as an electrically insulating material, while still allowing for nerve sensing and/or stimulation via the inner core or wire 410 to occur.

Accordingly, an electrical current from the nerve sensing/nerve stimulation device 600 may be supplied to the inner core or wire 410, which may then carry the electrical current along the length of the probe shaft 404 and to the distal tip 406, which may then be used to sense/stimulate nerves adjacent or in close proximity to the hole in the bone, either when the probe 400 is creating the hole (i.e., during the penetration of the bone), so as to provide real-, or near real-time feedback, or after the hole has been created to ensure that subsequent screw placement will not result in nerve damage or nerve pain.

As previously described herein, the present disclosure further relates to a handheld device is configured to perform at least one of penetration of a bone to form a hole or opening for receipt of a screw, neuromonitoring of the hole during, or post-, formation of the hole so as to sense any nearby nerves adjacent to the hole that may be in the path of a screw, or otherwise affected, when a screw is placed within the hole, and measuring of a depth of the hole and providing a digital measurement of the depth to assist the surgeon in selecting the appropriate length of screw.

Figure 16:
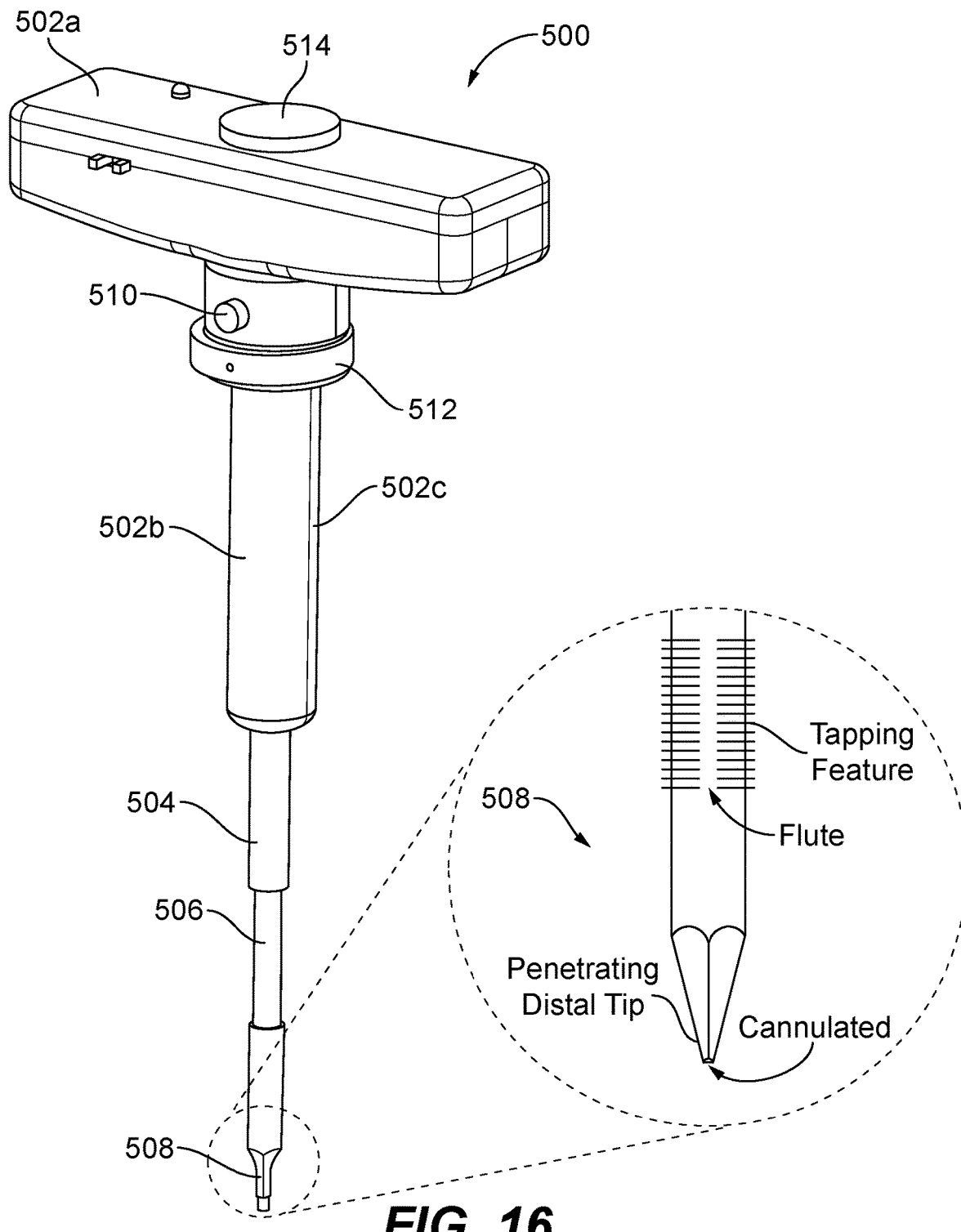
FIG. 16 is a perspective view of one embodiment of a handheld device consistent with the present disclosure.
Figure 17:
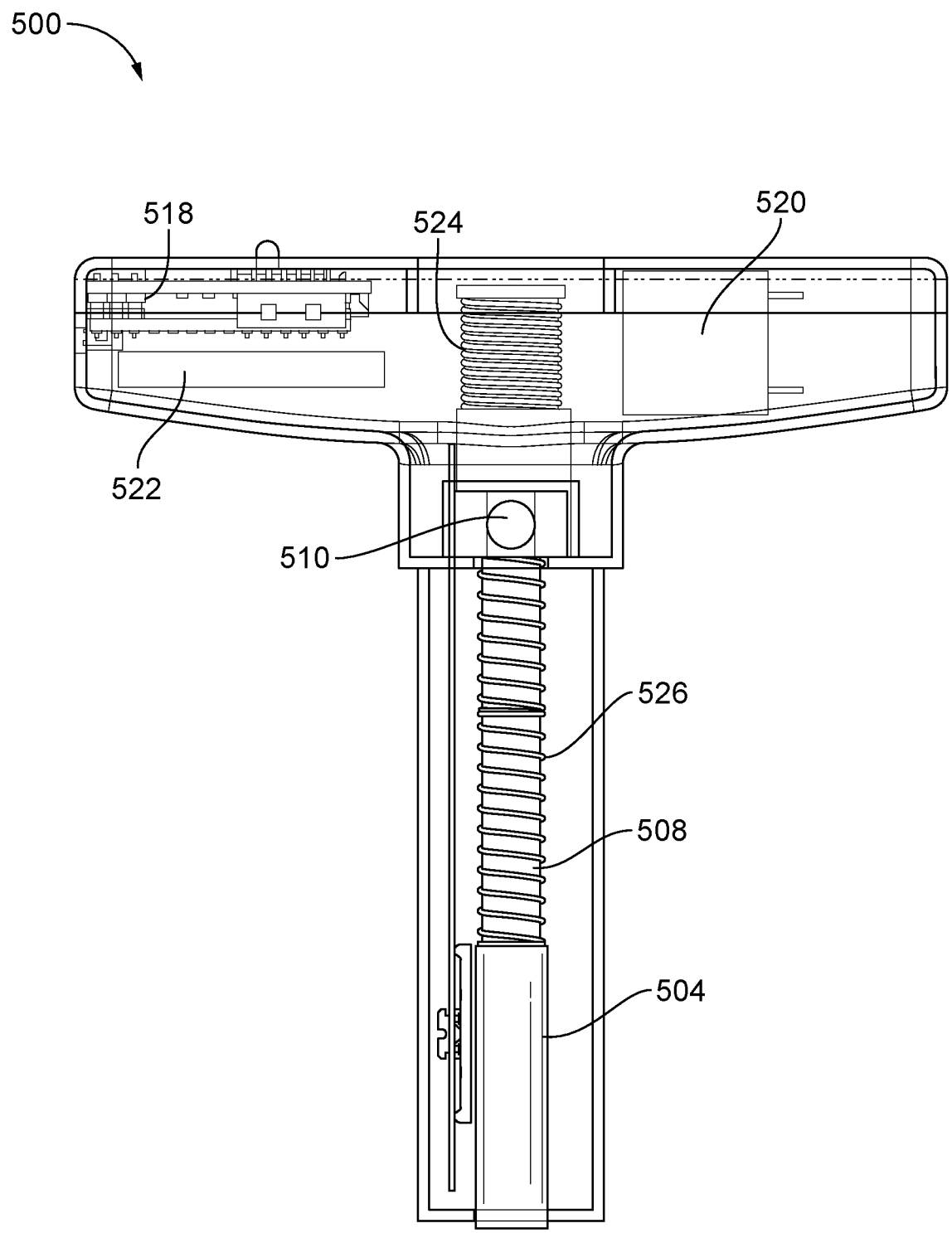
FIG. 17 is a side view of the handheld device of FIG. 16 partly in phantom illustrating internal components thereof.
Figure 18:
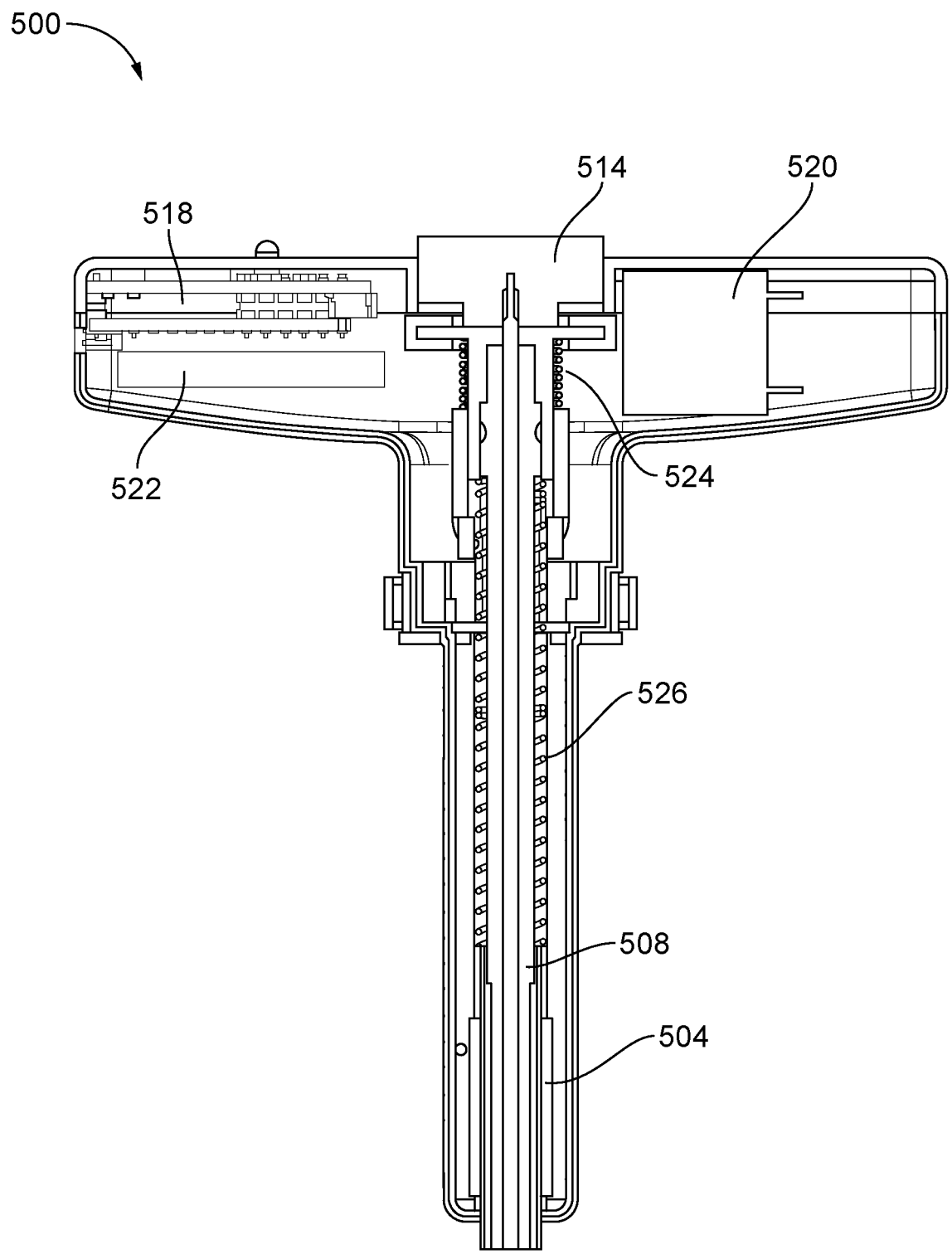
FIG. 18 is a cross-sectional view of the handheld device of FIG. 16.

FIG. 16 is a perspective view of a handheld device 500 consistent with the present disclosure. FIG. 17 is a side view of the handheld device 500, partly in phantom, and FIG. 18 is a cross-sectional view of the handheld device 500, each of which illustrates internal components thereof. As shown, the handheld device generally includes a housing having a top portion 502a, which may generally resemble and serve as a handle, and an elongate body portion extending therefrom, which may be formed by opposing front and back portions 502b, 502c. The device 500 further includes one or more depth sleeve members 504, 506 partially enclosed within the housing. For example, at least a proximal end of sleeve 504 resides within the body portion of the housing while a distal end of the sleeve 504 extends from the body portion and may terminate at a distal tip (not shown).

The depth sleeve member 504 is hollow such that the sleeve is configured to receive a medical tool or accessory therein, such as, for example, a probe, a pedicle awl, guidewire, or the like. For example, as shown in the figures, the handheld device 500 includes a cannulated awl-tap member 508. The awl-tap member 508 comprises a tubular rod having a penetrating distal tip configured to pierce bone and to create a pilot hole within the pedicle. The distal end of the awl-tap member further includes a tapping feature configured to cut or otherwise form a thread on the inside surface of the hole created by the distal tip of the awl-tap member. In particular, the tapping feature may generally include a set of external cutting threads, which may be separated by flutes, wherein, upon rotation of the awl-tap member, the cutting threads are configured to cut the interior surface of the hole to thereby form the female portion of a mating pair (i.e., create the internal threading within pedicle for threaded engagement with corresponding external threading of bone screw). At least a proximal end of the awl-tap member resides within the depth sleeve member 504 and is retained within the housing via a ball lock assembly.

As described in greater detail herein, the ball lock assembly provides a user with the ability to selectively lock and unlock rotational movement of the awl-tap member relative to the housing via a release button 510.

The handheld device 500 may be configured to allow for neuromonitoring functionality either during awl-tap member penetration into the bone, which, in turn, provides real-time, or near real-time, alerts to the surgeon as to the presence of any nearby nerves that may be in the path of a screw, or otherwise affected, when a screw is placed within the hole, or neuromonitoring functionality post hole creation. For example, the handheld device may include a return electrode assembly 512, which can allow for such neuromonitoring functionality, as will be described in greater detail herein, particularly with respect to FIG. 23. The neuromonitoring feedback can facilitate repositioning of the handheld device 500, particularly repositioning of the awl-tap member 508 during penetration into the bone, if there is any sensing of nearby nerves, thereby ensuring a properly formed hole and subsequently ensuring proper positioning of a screw within the hole so as to avoid inadvertent piercing, breaching, damage, or impinging upon unintended structures or tissues.

It should be noted that, in some embodiments, the awl-tap member itself may be conductive and thus may be configured to carry electrical current to and from a nerve sensing/nerve stimulation device or system 600 to provide at least neuromonitoring features. Additionally, or alternatively, one or both of the depth sleeve members 504, 506 may be conductive and thus configured to carry electrical current to and from a nerve sensing/nerve stimulation device or system 600 to provide at least neuromonitoring features. Thus, in some embodiments the awl-tap member and/or sleeves 504, 506 may be used for the sensing and/or stimulating of nerves adjacent or in close proximity to the hole in the bone, either when the awl-tap member 508 is creating the hole (i.e., during the penetration and tapping of the bone), so as to provide real-, or near real-time feedback, or after the hole has been created to ensure that subsequent screw placement will not result in nerve damage or nerve pain.

In addition to formation of a hole, and neuromonitoring functionality, the handheld device 500 enables the measuring of a depth of a hole and further outputting of a digital measurement of the depth. For example, the handheld device 500 further includes at least one sensor coupled to the depth sleeve member 504 and configured to generate an electronic signal indicative of a depth of the hole as a result of sensing movement (i.e., distance traveled) of the sleeve 504 or the housing relative to one another when the sleeve 504 is placed within a drilled hole and the distal tip meets sufficient resistance (i.e., abuts a base of the drilled hole or an opposing end of a bicortical drilled hole). The device 500 may allow for depth measurement from 5 mm to 100 mm, and in some embodiments, may allow for depth measurement from 13 mm to 70 mm.

Figure 30:
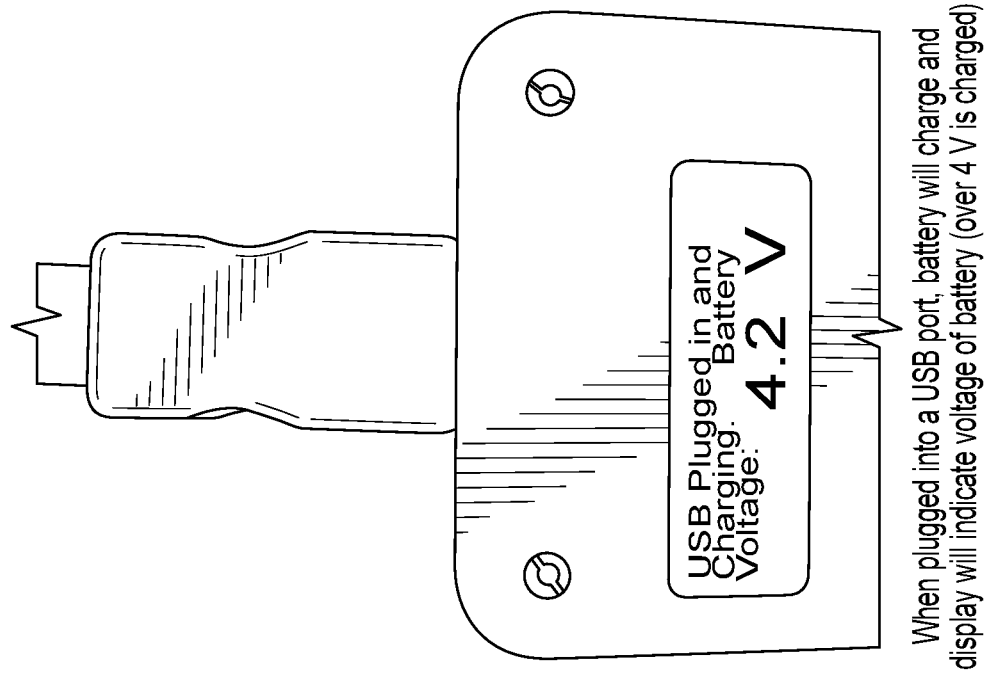
FIG. 30 is a view of the top portion of the housing illustrating exemplary data displayed thereon.
Figure 29:
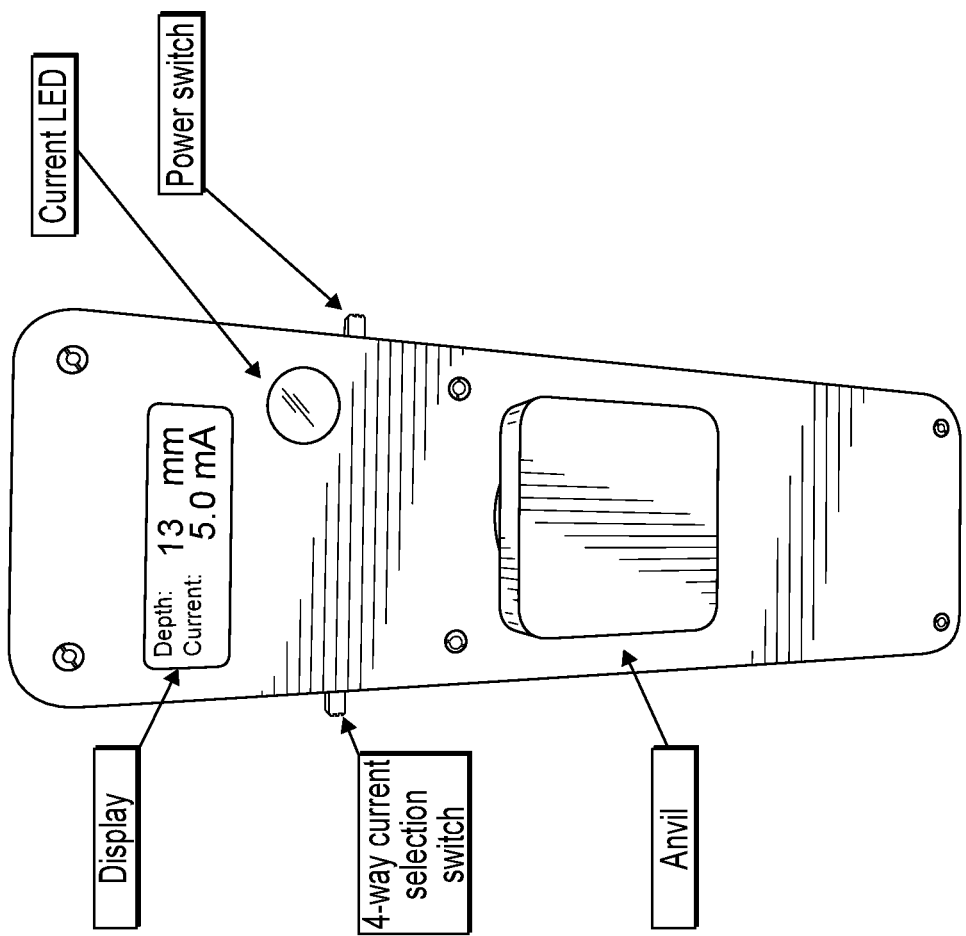
FIG. 29 is a view of the top portion of the housing illustrating one embodiment of a display provided thereon.

The sensor is further in communication with depth gauge electronics and/or circuitry provided on a printed circuit board (PCB) 518 enclosed within the housing. The device 500 may include other circuitry, such as a transistor 520, for example, depending on the functions provided. It should be further noted that the handheld device is a standalone device that is battery-operated (battery 522). The battery 522 may include, for example, a 3.7 volt lithium ion polymer battery. In some embodiments, the handheld device 500 may further include a display provided on the housing and configured to visually provide a digital readout of a depth measurement of the hole based on the electronic signal from the sensor, as well as other data, including, but not limited to, neurostimulation/neuromonitoring feedback, charge level of the battery, and the like (as shown in FIGS. 29 and 30). The battery may be rechargeable by way of micro-USB, or other means.

In some embodiments, the handheld device 500 may be configured to wirelessly communicate and exchange data with a separate display or computing device, such as, for example, a monitor or panel display, a PC, a notebook, a tablet computer, a smartphone, or other wireless computing device.

As shown in FIGS. 17 and 18, the device 500 further includes a return spring 526 applying a biasing force upon the depth sleeve member 504 such that a length of the sleeve extends out of the body portion of the housing when in a default position. The return spring 526 may generally comprise two stacked springs having a force of approximately 1 pound. The sleeve 504 may be shaped and/or sized to be received within the drilled hole, such that, upon engagement between the distal tip of the sleeve 504 and a base of the drilled hole, a user can continue pressing the handheld device 500 towards the drilled hole until, for example, a distal end of the body portion of the housing makes contact with the bone. The return spring 526 will become compressed due to the resistance upon the distal tip of the sleeve 504, while the surrounding body portion of the housing is moving towards the hole relative to the stationary sleeve. The device 500 further includes a ball lock return spring 524 (part of the ball lock assembly) used in applying a biasing force to maintain the awl-tap member 504 in a locked position, as will be described in greater detail herein.

Figure 19A:
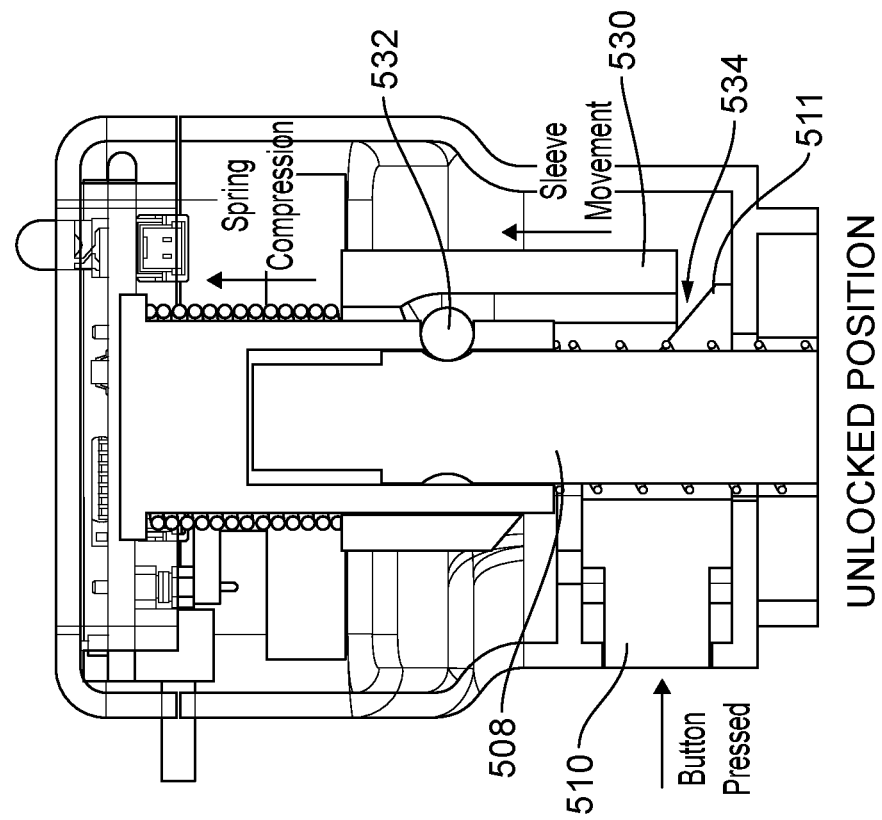
FIGS. 19A and 19B are enlarged side views, partly in section, of the handheld device of FIG. 16 illustrating transitioning of the ball lock assembly between locked and unlocked positions, respectively.
Figure 19B:
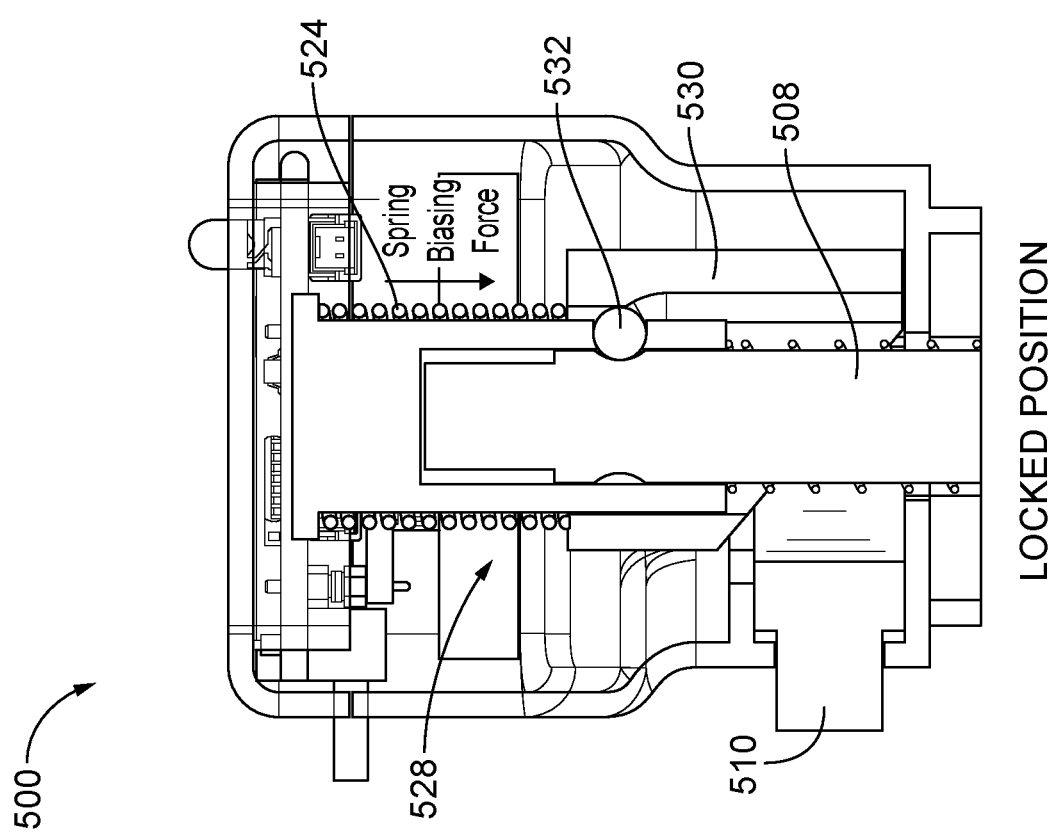

As previously described, the handheld device 500 includes a ball lock assembly for retaining the awl-tap member 508 in a rotational stationary position with respect to the housing. FIGS. 19A and 19B are enlarged side views, partly in section, of the handheld device 500 illustrating transitioning of the ball lock assembly 528 between a locked position (FIG. 19A) and unlocked position (FIG. 19B). FIGS. 20A and 20B are enlarged cross-sectional views of the handheld device 500 and similarly illustrate the transitioning of the ball lock assembly 528 between locked and unlocked positions, respectively. As shown, the ball lock assembly 528 generally comprises a housing surrounding a proximal portion of the awl-tap member 508, a ball lock sleeve 530 that is slidably mounted about the housing 528, a ball 532 positioned between the ball lock sleeve 530 and the awl-tap member 508, the ball lock return spring 524 applying a biasing force upon the slidable ball lock sleeve 530, and the release button 510 that allows for a user to selectively transition the ball lock assembly 528, particularly the ball lock sleeve 530, from a locked position (shown in FIGS. 19A and 20A) to an unlocked position (shown in FIGS. 19B and 20B). As shown, the proximal portion of the awl-tap member 508 may include an indentation or depression into which the ball 532 may rest and thereby prevent rotation of the awl-tap member 508 when the ball lock sleeve 530 is in the locked position (shown in FIGS. 19A and 20A), as the ball lock sleeve 530 is effectively maintaining the ball 532 within the corresponding indentation of the awl-tap member 508.

The ball lock assembly provides a user with the ability to lock the awl-tap member in a stationary position (i.e., no rotation relative to the housing) which further allows for the user to rotate the top portion of the housing (i.e., the handle) which, in turn, rotates the awl-tap resulting in advancement of the penetrating distal tip into bone to form a pilot hole and further engagement of the tapping feature within the pilot hole to create the internal threading for subsequent placement of a bone screw. The ball lock assembly further allows for a use to unlock the awl-tap member, thereby disengaging the awl-tap member from the housing with regard to rotational movement (i.e., rotation of the handle and rotation of the awl-tap member are independent of one another).

For example, by having the awl-tap member 508 locked in a stationary position (i.e., no rotation relative to the housing), a user is able to rotate the top portion of the housing (i.e., the handle) which, in turn, rotates the awl-tap 508 resulting in advancement of the penetrating distal tip into bone and subsequent engagement of the tapping feature with the interior surface of the hole. A user can unlock the awl-tap member 508 (i.e., disengage the awl-tap member 508 from the housing with regard to rotational movement) by simply pressing the release button 510, as shown in FIGS. 19B and 20B. When pushed, the release button 510 includes an angled surface 511 that engages, indicated at arrow 534, and subsequently moves the ball lock sleeve 530 towards the ball lock return spring 524, thereby disengaging a portion of the ball lock sleeve 530 from the ball 532 such that the ball 532 moves out of the indentation on the awl-tap member 508, allowing for rotation of the handle and rotation of the awl-tap member 508 independent of one another. When the user removes a pressing force upon the release button 510, the awl-tap member 508 becomes locked once again, as the biasing force of the ball lock return spring 524 causes the ball lock sleeve 530 to move back into the default position and into engagement with the ball 532, which subsequently returns to its position within the indentation on the proximal portion of the awl-tap member 508. It should be noted that the ball lock return spring 524 may have a force of approximately 2 pounds.

Measurement of the depth of the hole (formed by the awl-tap member) can be initially estimated at least based on the length of the distal tip and tapping feature of the awl-tap member. For example, the sharp distal tip of the awl-tap member may be advanced to a specific depth (i.e., depth of 20 mm which corresponds to length of the awl-tap member from the distal tip to the first external thread of the tapping feature along the length of the awl-tap member). Subsequently, upon rotation of the handle of the device when the ball lock assembly is in the locked position, the external threads begin to engage the pedicle and effectively pull the awl-tap member further into the bone, thereby increasing the depth of the hole formed. Depending on the specific type of bone screw to be used (i.e., specific length depending on specific procedure, bone, and area of the bone to receive the screw), the length of the tapping feature of the may be between 5 mm and 50 mm, for example. In one embodiment, the tapping feature (i.e., the external threading) may extend a length of approximately 20 mm. Accordingly, a surgeon will know once they have reached a depth of 40 mm once the threading has been completely engaged into the bone. It should be noted that different awl-tap members can be produced to be used with this handheld device, so as to accommodate various length screws and various screw diameters (i.e., 4 mm, 5 mm, 6 mm, 7 mm, and so on).

Figure 21:
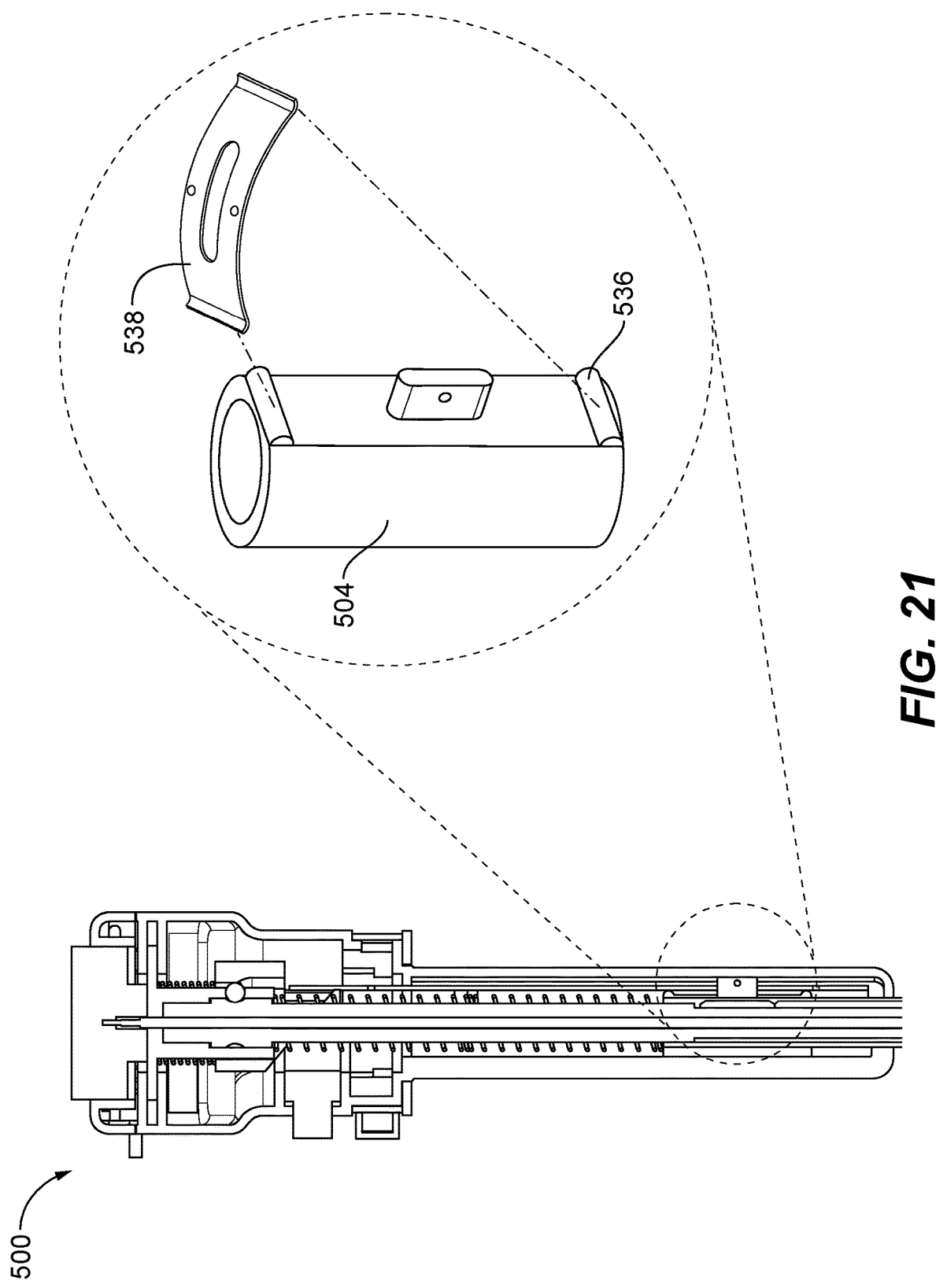
FIG. 21 is a cross-sectional view of the handheld device of FIG. 16 including an enlarged view of an exemplary resistor strip and contact coupled to the depth sleeve member and used in determining depth measurements based on a position of the sleeve member relative to the housing.

FIG. 21 is a cross-sectional view of the handheld device 500 illustrating one exemplary sensors for use in determining depth measurements. As previously described, the device 500 enables the measuring of a depth of a hole and further outputting of a digital measurement of the depth. For example, the handheld device 500 may include at least one sensor coupled to the depth sleeve member 504 and configured to generate an electronic signal indicative of a depth of the hole as a result of sensing movement (i.e., distance traveled) of the sleeve 504 or the housing relative to one another when the sleeve 504 is placed within a drilled hole and the distal tip meets sufficient resistance (i.e., abuts a base of the drilled hole or an opposing end of a bicortical drilled hole). As shown in FIG. 21, such a sensor may include an assembly consisting of an exemplary contact carrier 536 and brass contact 538 coupled to the sleeve member 504 and used in determining depth measurements based on a position of the sleeve member relative to the housing. For example, a depth measurement gauge member may be included in the body portion of the housing and the brass contact 538 may be used to provide depth measurement data as a result of direct contact between the brass contact 538 and the depth measurement gauge and subsequent movement of the brass contact 538 along a length of the depth measurement gauge, the measurement data being transmitted to depth gauge electronics and/or circuitry provided on the PCB 518 enclosed within the housing. FIGS. 22A and 22B are cross-sectional views of the handheld device 500 illustrating different positions of the sleeve member 504 and thus the contact carrier/brass contact 536, 538 assembly relative to the depth measurement gauge positioned within the housing, wherein said position is determinative of the depth of a drilled hole.

Figure 23:
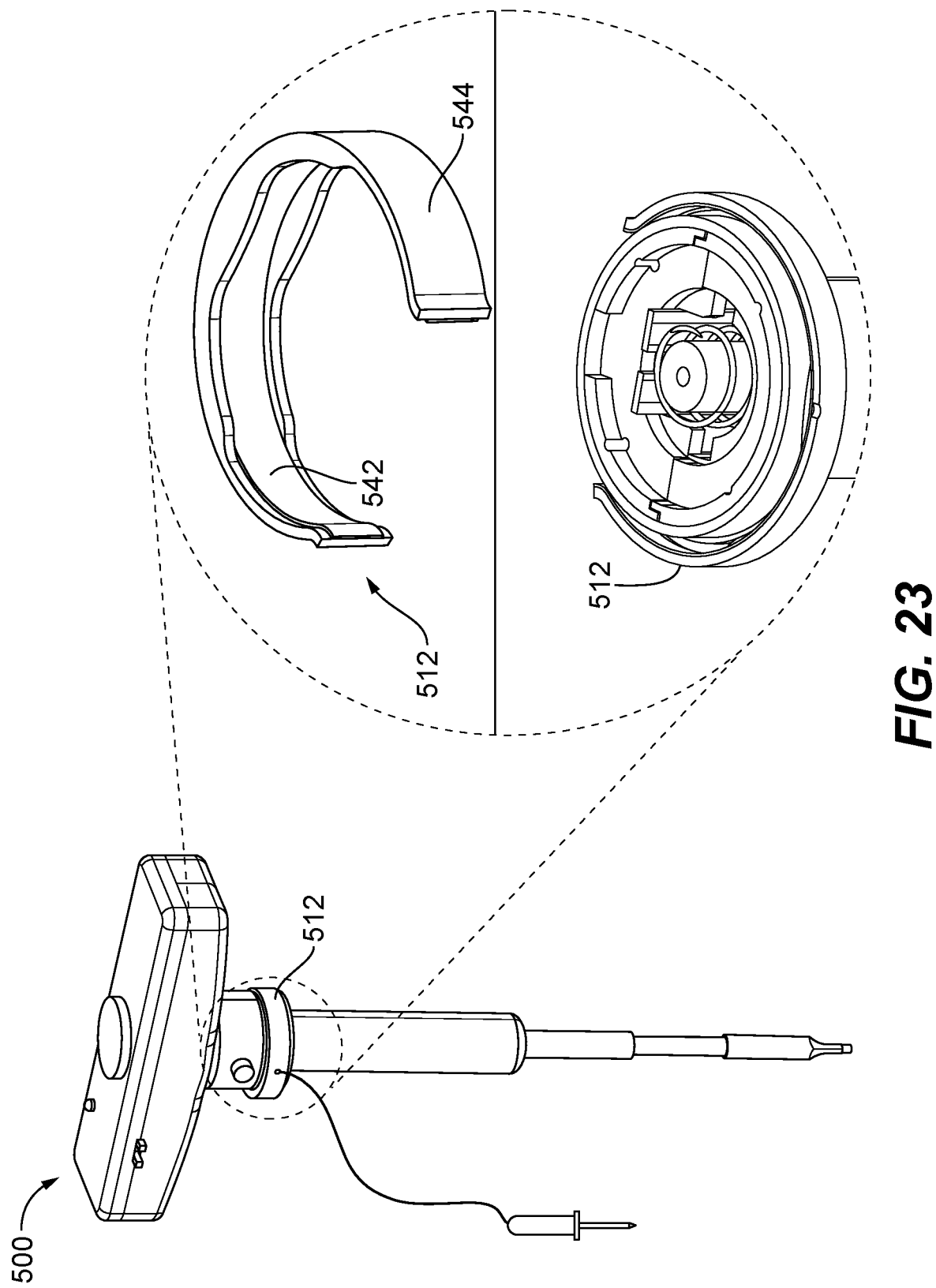
FIG. 23 is a perspective view of the handheld device of FIG. 16 including an enlarged view of an exemplary return electrode assembly for providing neuromonitoring capabilities.

FIG. 23 is a perspective view of the handheld device 500 including an enlarged view of an exemplary return electrode assembly 512, which can further allow for neuromonitoring capabilities. As shown, the return electrode assembly 512 generally includes a formed brass strip 542 and a plastic carrier 544 configured to hold the brass strip 542. The plastic carrier 544 is generally in the form of a clip configured to clip onto a portion of the housing of the device 500. A corresponding brass ring can be assembled onto the housing to thereby create an electrical pathway to the interior of the device. The assembly 512 further includes an electrical line coupled to a probe (e.g., needle probe), as shown in FIG. 23. The plastic carrier 544 clips on to the housing and thereby allows for independent movement about the housing (i.e., swivel around the housing).

Figure 24:
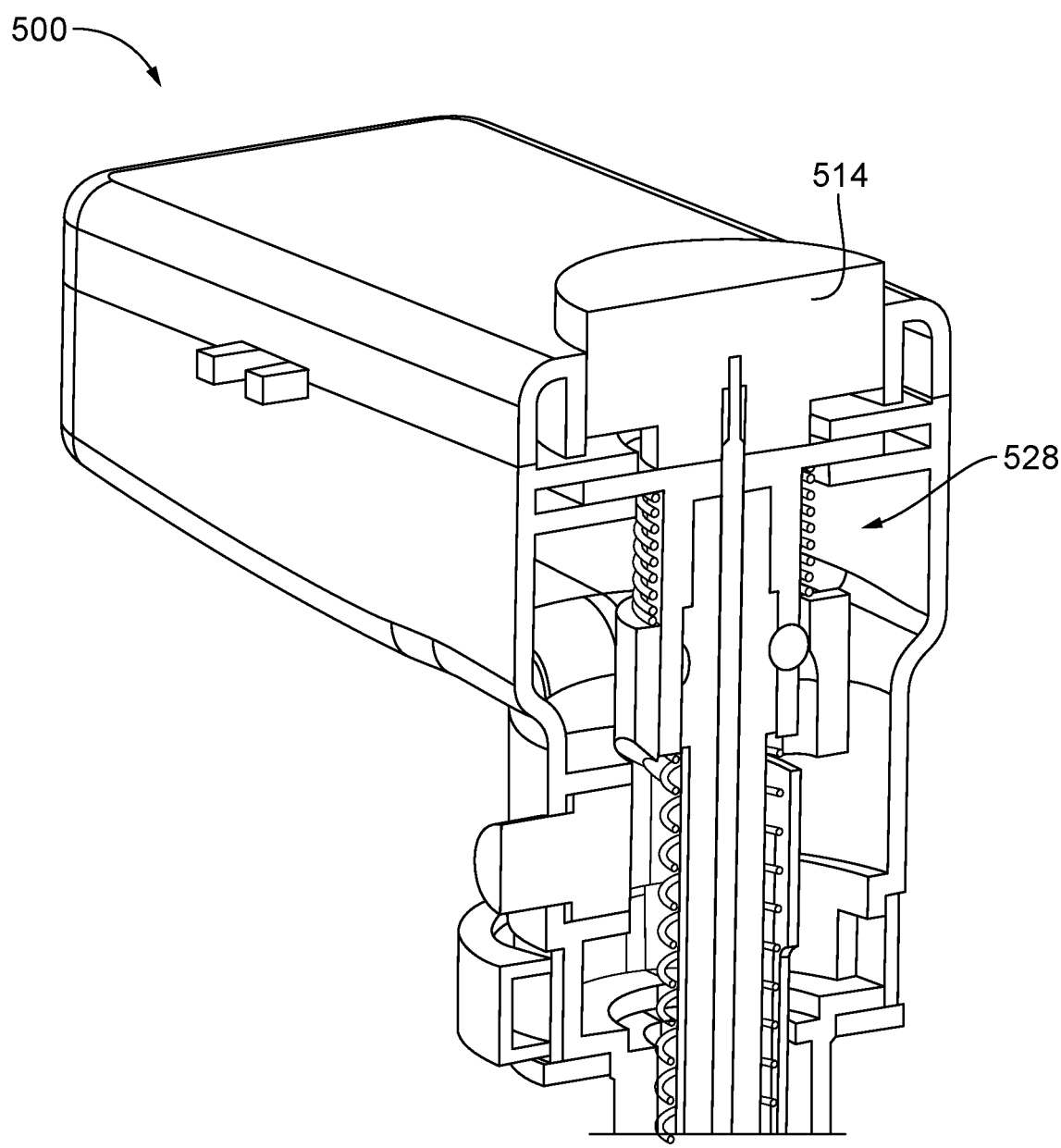
FIG. 24 is a perspective view, partly in section, of the handheld device of FIG. 16 illustrating an anvil member.

FIG. 24 is a perspective view, partly in section, of the handheld device 500 illustrating the anvil member 514 positioned on the top portion of the housing. The anvil 514 may comprise a polycarbonate material and is configured to be attached to a stimulation electrode or the like, thereby allowing for neuromonitoring and/or stimulation functionality.

As previously described herein, the awl-tap member 508 is cannulated (i.e., hollow) and is configured to receive a medical tool or accessory therein. For example, the cannulated awl-tap member 508 may be configured receive the guidewire assembly 100 described herein, which would improve accuracy of depth measurements and the ease with which an operator can take such depth measurements. In particular, the guidewire 100, when the hook member 102 is in the delivery configuration, may be inserted into the awl-tap member 508 and may translate along the length of the awl-tap member 508. Accordingly, once the hole is drilled, the hook member 102 may be extended out of the distal tip of the awl-tap member 508 and then anchored into place (i.e., either at the base of the hole or on the opposing side of bone in a bicortical drilled hole), such that the guidewire provides improved stability during a depth measurement procedure and/or screw placement procedure, as the guidewire essentially acts as a guide for the depth sleeve member to slide along a length thereof. Furthermore, the hook member provides an accurate datum from which the depth of the hole can be determined, thereby improving the precision with which depths of holes can be determined. For example, upon establishing an anchored position with the hook member, a user need only slide the sleeve member towards the drilled hole until a distal-most end of the sleeve member engages the hooked end.

Accordingly, once the hook member is anchored in place, the guidewire provides improved stability during a depth measurement procedure and/or screw placement procedure, as the guidewire essentially acts as a guide for a depth sleeve member of the handheld device to slide along a length thereof when measuring a depth of the drilled hole. Furthermore, the hook member provides an accurate datum from which the depth of the hole can be determined, thereby improving the precision with which depths of holes can be determined. For example, upon establishing an anchored position with the hook member, a user need only slide the depth sleeve member of the handheld device towards the drilled hole until a distal-most end of the sleeve member engages the hook end. Accordingly, in combination with the hooked end guidewire, the handheld device allows for accurate measurements of the depth of a hole and provides a digital display of the depth measurement, thereby providing the surgeon with a quick and accurate reading upon which they rely when selecting the appropriate length screw (ensuring they do not select a screw that is either too short or too long).

Figure 25:
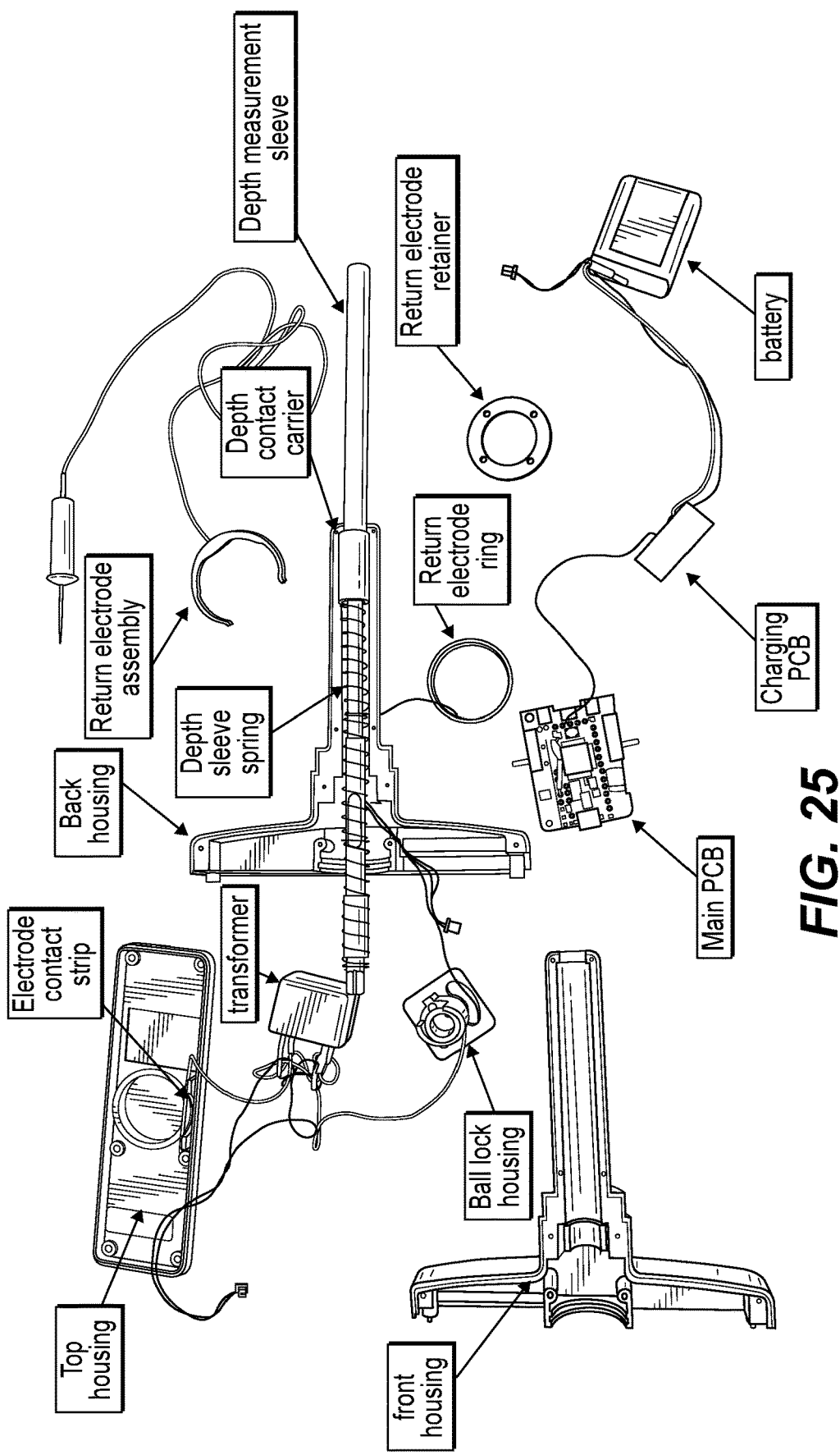
FIG. 25 is an exploded view of the handheld device of FIG. 16 illustrating components thereof.
Figure 26:
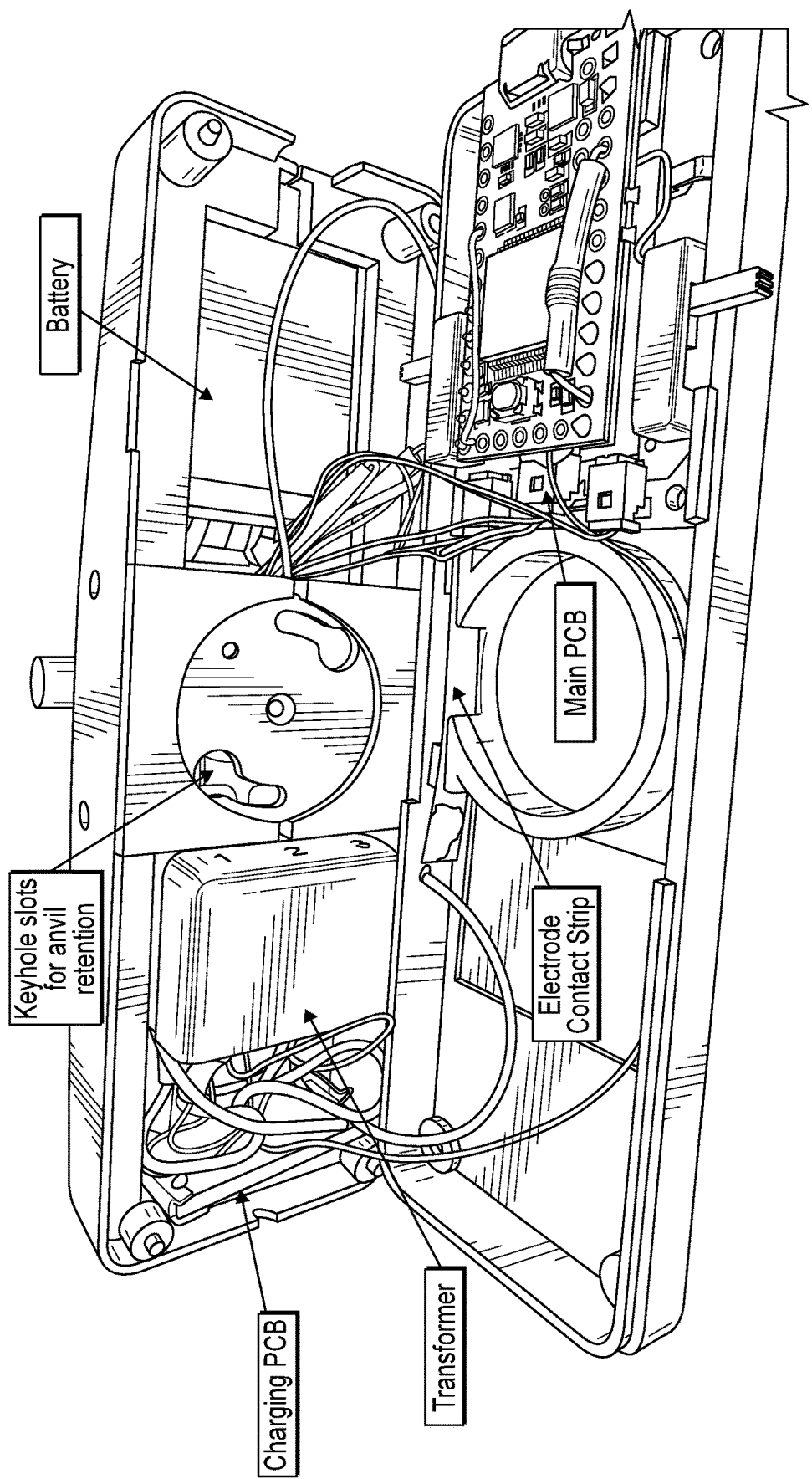
FIG. 26 is an interior view of the top portion of the housing illustrating internal components housed therein.

FIG. 25 is an exploded view of the handheld device illustrating the various components thereof, as previously described herein. FIG. 26 is an interior view of the top portion of the housing illustrating internal components housed therein.

Figure 28:
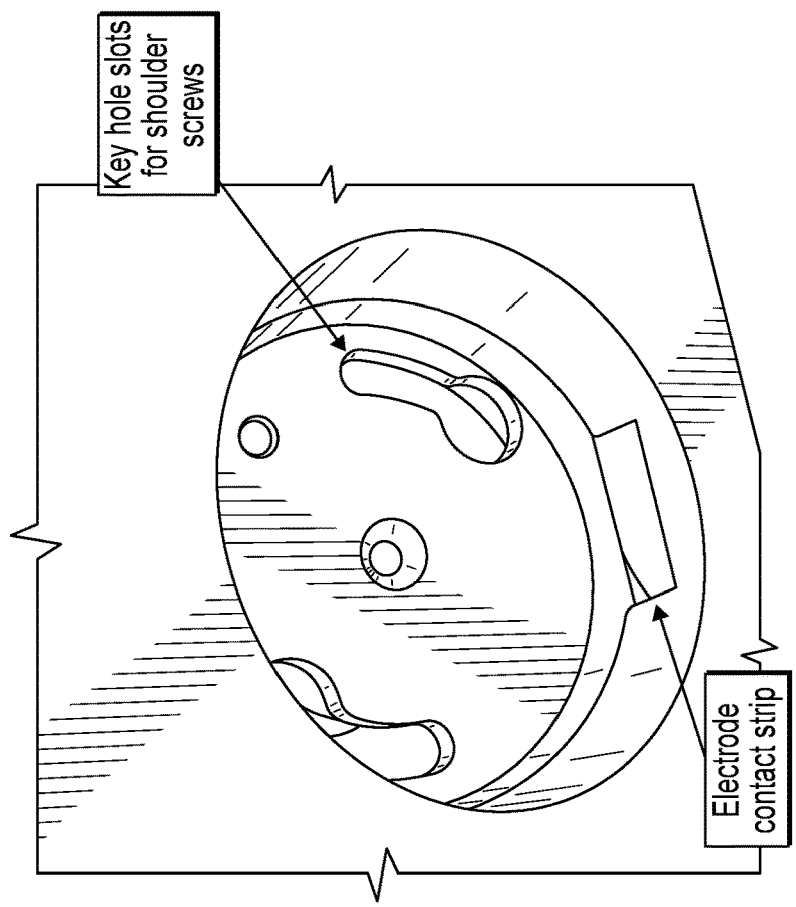
FIG. 28 is a perspective view of the top portion of the housing illustrating a recess formed therein configured to receive the anvil member.
Figure 27:
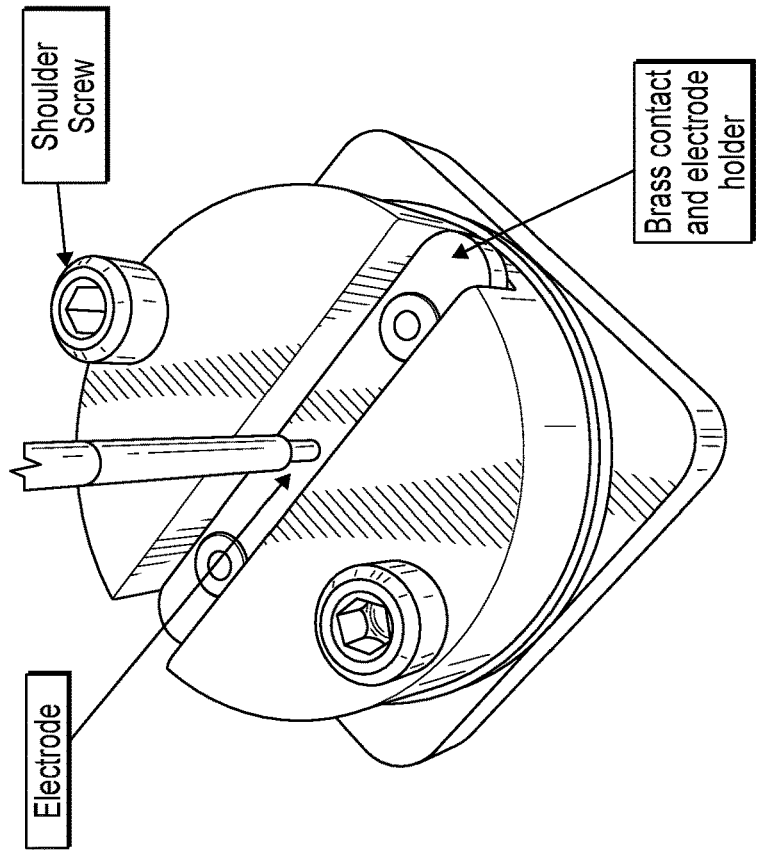
FIG. 27 is a perspective view of the anvil member.

FIG. 27 is a perspective view of the anvil member and FIG. 28 is a perspective view of the top portion of the housing illustrating a recess formed therein configured to receive the anvil member.

FIG. 29 is a view of the top portion of the housing illustrating one embodiment of a display and exemplary data displayed thereon. The display screen may indicate depth, current settings, as well as battery voltage during charging. For example, as shown in FIG. 29, the data may include, for example, the measured depth as well as the amount of current applied during a neurostimulation/neuromonitoring event, for example. FIG. 30 is a view of the top portion of the housing illustrating additional exemplary data displayed thereon, including the voltage of the rechargeable battery to thereby indicate the charge level of the battery.

As previously described, the handheld device 500 may be configured to allow for neuromonitoring functionality either during awl-tap member penetration into the bone, which, in turn, provides real-time, or near real-time, alerts to the surgeon as to the presence of any nearby nerves that may be in the path of a screw, or otherwise affected, when a screw is placed within the hole, or neuromonitoring functionality post hole creation. The neuromonitoring feedback can facilitate repositioning of the handheld device 500, particularly repositioning of the awl-tap member 508 during penetration into the bone, if there is any sensing of nearby nerves, thereby ensuring a properly formed hole and subsequently ensuring proper positioning of a screw within the hole so as to avoid inadvertent piercing, breaching, damage, or impinging upon unintended structures or tissues. For example, in a first configuration, nerve stimulation is provided through the bi-polar electrode. The patient's muscles must be monitored for feedback. Nerve stimulation can be performed at 0.5, 5 and 20 ma, for example.

In a second configuration, neuromonitoring is provided through a single pole electrode and a return electrode placed into a muscle. The handheld device is configured to monitor whether or not an electrical circuit is created between the two electrodes. If a circuit is detected, then a nerve is too close to the awl-tap member. In a third configuration, a neuromonitoring probe can be provided. Most, if not all, electronics that control either nerve stimulation or neuromonitoring can be eliminated and the return electrode is used to connect to an existing neuromonitoring console. The device becomes a depth measuring probe for the neuromonitoring console.

It should be noted that, once depth of the hole is determined, and any neuromonitoring/neurostimulation has been performed, the bone screw can be positioned and secured within the hole by utilizing a guidewire, including a guidewire consistent with the present disclosure. For example, guidewire 100 may be used to help guide a cannulated bone screw to the bone and hold the bone relatively steady as the surgeon advances the screw into the hole further secures the screw via rotation thereof.

FIGS. 31A-31H illustrate a series of steps for performing a procedure of deploying the hook member 102 of the guidewire 100 and subsequently obtaining a depth measurement using a surgical depth instrument consistent with the present disclosure. For example, FIGS. 31A-31H illustrate processes for obtaining a depth measurement using the sleeve member 200 and probe 300. However, it should be noted that depth measurement can also be obtained using the handheld instrument 500 illustrated in FIGS. 16, 17, 18, 19A-19B, 20A-20B, 21, 22A-22B, 23, 24, 25, 26, 27, 28, 29, and 30. As shown in FIG. 31A, a procedure may begin in which the surgeon, or other medical professional, begins to advance the guidewire 100, specifically the hook member 102, into a drilled hole in a bone. The hook member 102 is in the delivery configuration, and due to its compact size while in the delivery configuration, the hook member 102 may be freely positioned within and move through the drilled hole. In the figures, the hole is drilled entirely through the bone (i.e., bicortical drill hole), and thus the surgeon advances the hook member 102 entirely through the hole, as shown in FIG. 31B.

Upon reaching the desired position, the surgeon then actively controls transitioning of the hook member from the delivery configuration to the deployed configuration, as shown in FIG. 31C. In this instance, the surgeon would like to obtain the depth of the hole for the purpose of selecting the correct length of screw to use for the bicortical drill hole. Accordingly, upon transitioning the hook member to the deployed configuration, in which the expanded diameter is much greater than the drilled hole diameter and opening, and the surgeon pulls back on the guidewire 100 until the expanded hook member 102 securely engages the exterior surface of the bone adjacent to the drilled hole, as shown in FIG. 31D. Due to the resilient nature of the material of the struts, the hook member 102 may essentially flatten against the surface of the bone in response to the surgeon pulling back on the guidewire 100, and the flattening may enhance tactile feel, providing the surgeon with an indication that the hook member 102 is sufficiently anchored.

At this point, with the guidewire secured 100 in position, the surgeon can simply slide the sleeve member 200 over the guidewire 100 and further assemble the probe 300 with the sleeve member 200, as shown in FIG. 31E. In order to begin the depth measurement of the hole via the probe 300, the surgeon may first advance the sleeve member 200, while mounted to the guidewire 100, towards the opening of the hole until the distal end 204 of the sleeve member 200 engages at least the opening of a drilled hole, at which point, the flanged member 205 is configured to engage the exterior surface of the bone along a periphery of the hole opening, as shown in FIG. 31F. The distal end 204 of the sleeve member 200 establishes engagement and maintains the sleeve member 200 in a stabilized position, at which point, the probe 300 can be used for measuring the depth of the hole. In particular, as shown in FIG. 31G, the surgeon advances the probe 300 within the hole until it reaches the anchored hook member 102, which serves as a stopping point for the probe 300 and thus provides a datum from which the depth of the hole can be determined. Upon the distal tip 306 of the probe 300 engaging the hook member 102, shown in FIG. 31H, the measurement of the depth of the hole is now complete, in that the sensor has determined the distance traveled by the probe 300 and thus is able to calculate the corresponding depth of the hole.

FIGS. 32A-32D illustrate a series of steps for transitioning the hook member 102 from the deployed configuration to the delivery configuration to allow for retraction of the hook member 102 back into the drilled hole and subsequently utilizing the guidewire 100 and hook member 102, particularly the plurality of struts or splines 104 of the hook member 102, to carry electrical current to and from a nerve sensing/nerve stimulation device 600 for neuromonitoring purposes. In particular, the guidewire 100 and hook member 102 may include an electrically conductive material configured to carry an electrical signal to and from a nerve sensing/nerve stimulation device 600, which may include a metal or other conductive material.

Upon obtaining the depth measurement (shown in FIG. 31H), the surgeon, or other medical professional, may wish to determine whether there are any nearby nerves that may present potential issues during placement of a screw within the drilled hole. In particular, there may be nerves present within the bone itself (as opposed to nerves positioned outside of the bone but adjacent thereto). Accordingly, a surgeon may wish to know whether there are any nerves within the bone adjacent the pathway of the drilled hole. As shown in FIG. 32A, a surgeon may first disengage the hook member 102 from its anchored position at the exit point of the drilled hole. Then, the surgeon may transition the hook member from its deployed configuration to its delivery configuration, essentially collapsing the struts or splines so as to decrease the overall diameter of the hook member, shown in FIG. 32B. The surgeon then need only collapse the hook member 102 to a sufficient diameter so as to allow the hook member 102 to be retracted back into the hole, while leaving the struts or splines 104 expanded enough so as to contact the interior surface of the hole, as shown in FIG. 32C. At this point, with the struts or splines 104 in contact with the interior surface of the drilled hole, the surgeon need only couple a proximal end of the guidewire directly to a connector (or other coupling device) of the nerve sensing/nerve stimulation device 600, at which point, the guidewire 100 and hook member 102 may be configured to act as an extension to the nerve sensing/stimulation device 600 and may be used to sense/stimulate nerves within or adjacent to the bone. As a result of being made from a conductive material, guidewire 100 and hook member 102, specifically the struts or splines 104, may carry signals to and from the interior surface of the drilled hole used to sense/stimulate nerves adjacent or in close proximity to the drilled hole in the bone when the hook member 102 is directly placed within the drilled hole.

As previously described, the present invention further includes a system and a handheld device for use in a minimally invasive surgical procedure, such as a bone implant fixation procedure. The following description relates to a system including a handheld device configured to perform various functions during a bone implant fixation procedure, including performing at least one of: penetration of a bone to form a hole or opening for receipt of a screw; neuromonitoring of the hole during, or post-, formation of the hole so as to sense any nearby nerves adjacent to the hole that may be in the path of a screw, or otherwise affected, when a screw is placed within the hole; neurostimulation of nerves adjacent to the hole during, or post-, formation of the hole; and measuring of a depth of the hole and providing a digital measurement of the depth to assist the surgeon in selecting the appropriate length of screw.

FIGS. 33A and 33B are schematic illustrations of a system 3300 for a bone implant fixation procedure. The system 3300 includes a neuromonitoring device 3302, which may be coupled to and placed in electrical connection with a handheld device 3400 via cable 3310. Cable 3310 is connected to neuromonitoring device 3302 at input connector 3306. The neuromonitoring device 3302 includes electrode inputs 3312, to which various electrodes may be electrically connected, depending on the function intended. For example, for neuromonitoring functions, a return electrode is used to detect a muscle of a patient 3390 enervated by a nerve adjacent to a hole into which the cannulated awl-tap member 3406 of handheld device 3400 is inserted.

The handheld device 3400 generally includes a handle 3401 including a grip portion providing a surgeon or other medical professional with a means to manipulate the device 3400 and components thereof. The handheld device 3400 further includes a depth sleeve member 3404 operably associated with the handle and configured to move relative thereto. The handheld device 3400 further includes an awl-tap member 3406 releasably coupled to the handle 3401, the awl-tap member 3406 includes a distal tip 3408 configured to penetrate bone upon manipulation of the grip portion of the handle 3401. The depth sleeve member 3404 comprises an elongate body including a lumen extending therethrough within which a portion of the awl-tap member 3406 is received and extends therefrom. As will be described in greater detail herein, the handheld device 3400 provides a depth measurement function in which a depth of the hole formed via the awl-tap member 3406 is measured in real-time (i.e., as the awl-tap member 3406 advances into bone) via the depth sleeve member 3404 and an associated depth measurement sensor operably associated with the depth sleeve member 3404. The body of the awl-tap member 3406 is electrically conductive and is operable to carry electrical current for neurostimulation and neuromonitoring functions by way of a cable 3310 coupled to the handheld device 3400 and in communication with the awl-tap member 3406. The neurostimulation and neuromonitoring functions are described in greater detail herein.

Figure 34:
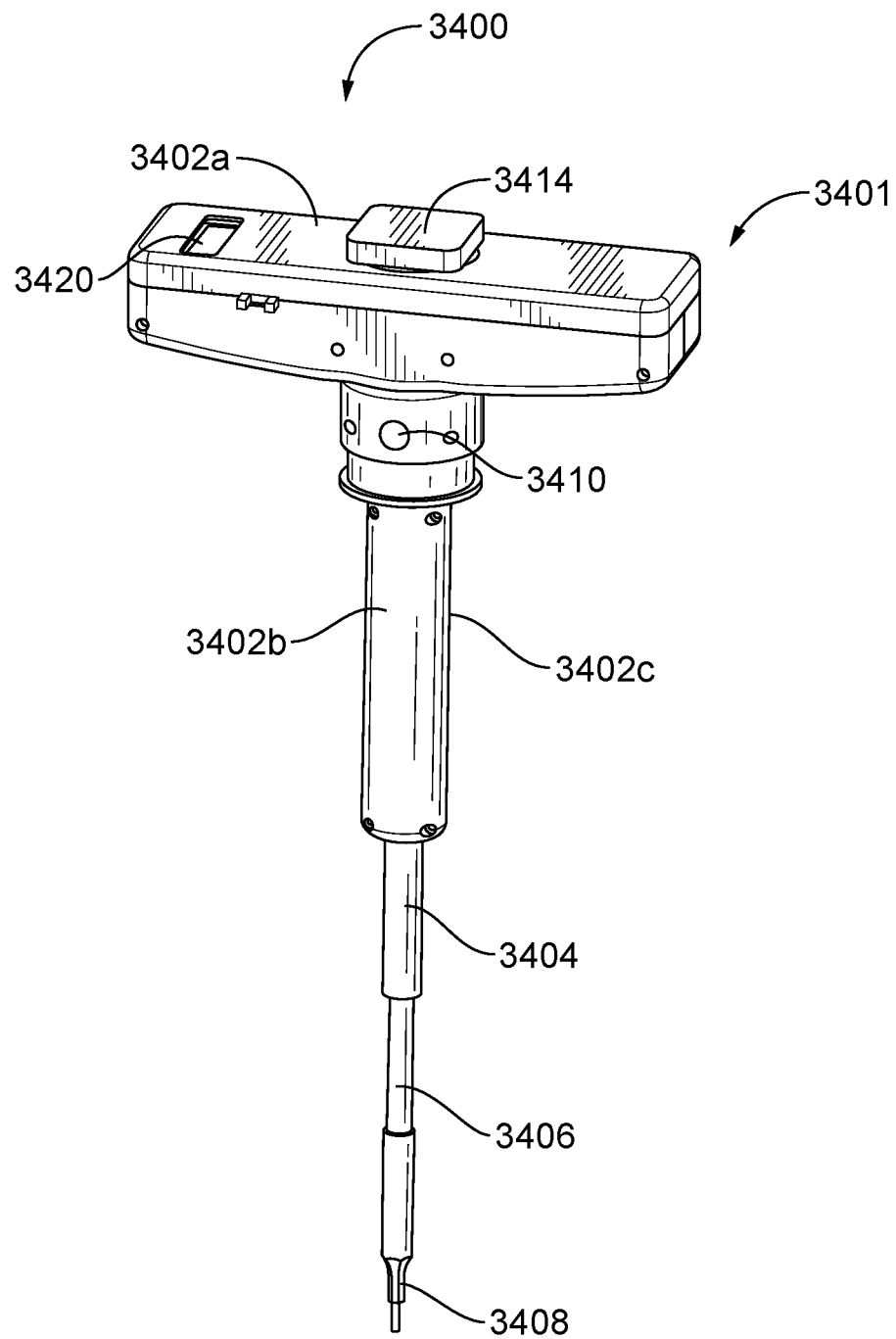
FIG. 34 is a perspective view of the handheld device of FIG. 33B consistent with the present disclosure.
Figure 35:
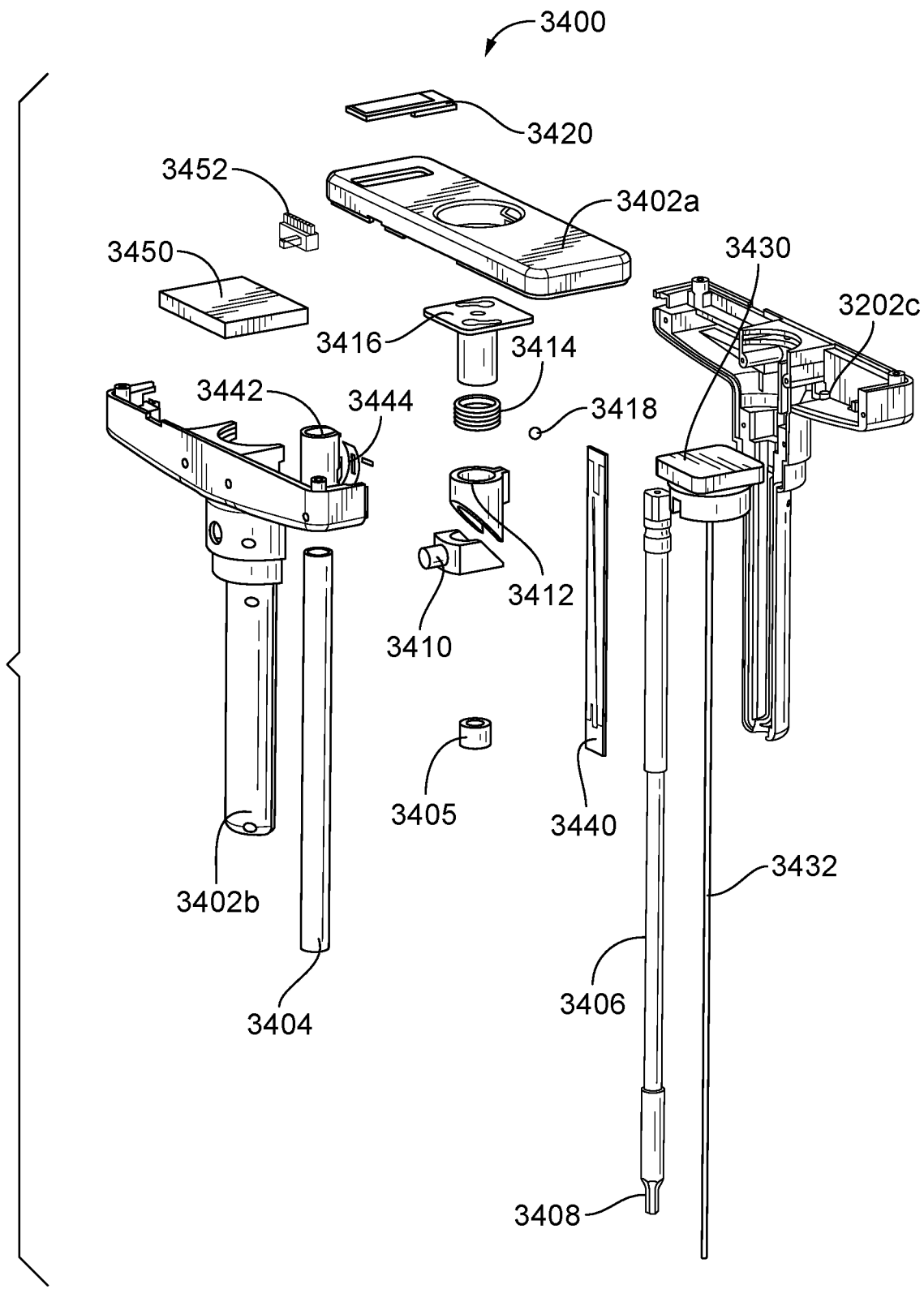
FIG. 35 is an exploded view of the handheld device of FIG. 34 illustrating components thereof.

FIG. 34 is a perspective view of the handheld device 3400 in more detail. FIG. 35 is an exploded view of the handheld device 3400 illustrating components thereof. As shown, the handheld device 3400 includes a handle 3401 comprising a body including a grip portion at its proximal end and an elongate portion extending from the grip portion and forming a distal end of the body. The handle 3401 is formed from multiple components that, when assembled to one another, form a complete handle that further houses various components within, including portions of the depth sleeve member 3404 and the cannulated awl-tap member 3406. For example, the handle 3401 includes at least a top panel 3402*a* and opposing front and back panels 3402*b*, 3402*c* that, when coupled to one another, form an assembled handle 3401.

The depth sleeve member 3404 comprises an elongate hollow body including a proximal end operably associated with the handle 3401 and an opposing distal end extending from the handle 3401. For example, as shown, at least a portion of the depth sleeve member 3404 (i.e., a length of the depth sleeve member 3404 at the proximal end) is enclosed within the handle 3401 and a length of the depth sleeve member 3404 adjacent the distal end extends from the elongate body portion of the handle 3401. The hollow body of the depth sleeve member 3404 includes a lumen extending entirely therethrough, in which the body of the awl-tap member 3406 is received within when the awl-tap member 3406 is coupled to the handle 3401. The depth sleeve member 3404 and awl-tap member 3406 are configured to move independent of one another (i.e., the awl-tap member 3406 is able to rotate about a longitudinal axis thereof in response to rotation of the grip portion of the handle 3401 while the depth sleeve member 3404 may remain stationary and/or the awl-tap member 3406 is able to be advanced into bone while the depth sleeve member 3404 remains stationary relative to the bone).

Furthermore, the depth sleeve member 3404 is configured to move relative to the handle 3401 as well, which is particularly useful when measuring a depth of a hole formed by the awl-tap member 3406, as will be described in greater detail herein. For example, in some embodiments, the handheld device 3400 further includes a sleeve spring 3405 that applies a biasing force upon a portion of the depth sleeve member 3404 at or near the proximal end such that the depth sleeve member 3404 is biased in a direction away from the handle 3401 when in a default position (i.e., prior to a hole formation procedure in bone). The distal end of the depth sleeve member 3404 is shaped and/or sized to engage an exterior surface of the bone along a periphery of an opening of a hole to be formed via the awl-tap member 3406. Accordingly, upon engagement between the distal end of the depth sleeve member 3404 and the exterior surface of the bone, a user can advance the distal tip 3408 of the awl-tap member 3406 into bone to begin forming the hole (either by rotation of the awl-tap member 3406 or applying force upon the awl-tap member 3406 to press the distal tip 3408 into bone). As the distal tip 3408 of the awl-tap member 3406 is drawn into the bone and begins forming a hole, the handle 3401 is correspondingly drawn in a direction towards the bone. While both the awl-tap member 3406 and handle 3401 are drawn in a direction towards the bone as the hole is formed, the distal end of the depth sleeve member 3404 remains in contact with the exterior surface of the bone along the periphery of the opening of the hole and is essentially pushed in an opposing direction toward the handle 3401, such that the portion of the depth sleeve member 3404 at or near the proximal end thereof pushes upon the sleeve spring 3405, thereby compressing the sleeve spring 3405. Such movement of the depth sleeve member 3404 is measured in real-time (i.e., as the awl-tap member advances into bone) via a depth measurement sensor operably associated with the depth sleeve member 3406.

The awl-tap member 3406 comprises a tubular body including a penetrating distal tip 3408 configured to pierce bone and to create a pilot hole within the pedicle. The body of the awl-tap member is electrically conductive and is operable to carry electrical current for neurostimulation and neuromonitoring functions. The distal tip 3408 of the awl-tap member 3406 further includes a tapping feature configured to cut, or otherwise form, a thread on the inside surface of the hole created by the distal tip of the awl-tap member. In particular, the tapping feature may generally include a set of external cutting threads, which may be separated by flutes, wherein, upon rotation of the awl-tap member, the cutting threads are configured to cut the interior surface of the hole to thereby form the female portion of a mating pair (i.e., create the internal threading within pedicle for threaded engagement with corresponding external threading of bone screw). Accordingly, in certain embodiments, the handheld device 3400 further includes a ratchet assembly that rotatably couples the handle 3401 and the awl-tap member 3406 to one another, as will be described in greater detail herein, more specifically with reference to FIGS. 39-41.

The awl-tap member is cannulated (i.e., hollow) and is configured to receive a medical tool or accessory therethrough, such as, for example, a probe, a stylet, a guidewire, or the like. For example, a stylet 3432 may be positioned within a lumen of the awl-tap member 3406 to prevent bone debris or other tissues from entering the lumen as the distal tip 3408 of the awl-tap member 3406 is advanced into bone. The stylet 3432 may be coupled to an anvil 3430 at a proximal end, which facilitates inserting and removing the stylet 3432 from the lumen of the awl-tap member 3406.

At least a proximal end of the awl-tap member 3406 is retained within the handle 3401 via a ball lock assembly. In some embodiments, the ball lock assembly may provide a user with the ability to selectively lock and unlock rotational movement of the awl-tap member 3406 relative to rotational movement of the handle 3401. The ball lock assembly includes a ball housing 3416, a spring 3414, a ball 3418, a ball retainer 3412, and release button 3410. Additionally, or alternatively, the ball lock assembly may provide a user with the ability to lock the awl-tap member 3406 in place to remain coupled to the handle 3401 during a procedure and unlock the awl-tap member 3401 upon completion of the procedure, thereby disengaging the awl-tap member 3406 from the handle 3401 to allow removal of the awl-tap member 3406 if desired. Accordingly, the handle 3401 may be configured to receive one of a plurality of different awl-tap members, each releasably couplable to the handle 3401 and interchangeable with one another. In particular, the handle 3401 is able to be equipped with any one of a plurality of interchangeable awl-tap members as the surgeon sees fit, which is particularly beneficial as each awl-tap member may have a specific length, diameter, penetration member configuration, and other qualities that may be useful for any particular procedure.

As previously described, the body of the awl-tap member 3406 is electrically conductive and is operable to carry electrical current for neurostimulation and neuromonitoring functions. Accordingly, the handheld device 3400 can provide neuromonitoring functionality during penetration into the bone via the awl-tap member 3406, which, in turn, provides real-time, or near real-time, alerts to the surgeon as to the presence of any nearby nerves that may be in the path of a screw, or otherwise affected, when a screw is placed within the hole. The neuromonitoring feedback can facilitate repositioning of the handheld device 3400, particularly the penetrating distal tip 3408 of the awl-tap member 3406, if there is any sensing of nearby nerves, thereby ensuring a properly formed hole and subsequently ensuring proper positioning of a screw within the hole so as to avoid inadvertent piercing, breaching, damage, or impinging upon unintended structures or tissues. The neuromonitoring feedback can also inform the determination of electrical parameters used for neurostimulation of nerves adjacent or in close proximity to the hole. The performing of neurostimulation and neuromonitoring functions with the neuromonitoring device 3302 and handheld device 3400, as well as the associated components, are described in greater detail herein with reference to FIGS. 36-38.

As previously described, the handheld device 3400 provides a depth measurement function in which a depth of the hole formed via the awl-tap member 3406 is measured in real-time (i.e., as the awl-tap member 3406 advances into bone) via the depth sleeve member 3404 and a depth measurement sensor operably associated with the depth sleeve member 3404. For example, a depth measurement of the hole may be determined and displayed simultaneously as the hole is being formed via the distal tip 3408 of awl-tap member 3406. In particular, sleeve member 3404 is provided with a sleeve spring 3405 that biases the sleeve member 3404 in a direction away from the handle 3401. The sleeve member 3404 has an initial resting position, at which at least a portion of distal tip 3408 of the awl-tap member 3406 protrudes from the distal end of sleeve member 3404. It should be noted that, in the embodiment illustrated in FIG. 34, the sleeve member 3404 is shown in a partially retracted configuration and is not shown in the fully extended configuration in which most of the length of the awl-tap member 3406 would be enclosed within the sleeve member 3404. Rather, as illustrated in FIG. 34, the sleeve member 3404 is shown pushed upward into the handle 3401, thereby revealing a length of the awl-tap member 3406.

The distal end of the depth sleeve member 3404 is shaped and/or sized to engage an exterior surface of the bone along a periphery of an opening of a hole to be formed via the awl-tap member 3406. Accordingly, at an initial position, in which there is engagement between the distal end of the depth sleeve member 3404 and the exterior surface of the bone, a user can then begin formation of the hole in the bone by advancing the distal tip 3408 of the awl-tap member 3406 into bone (either by rotation of the awl-tap member 3406 or applying force upon the awl-tap member 3406 to press the distal tip 3408 into bone). As the distal tip 3408 of the awl-tap member 3406 is drawn into the bone and begins forming a hole, the handle 3401 is correspondingly drawn in a direction towards the bone. While both the awl-tap member 3406 and handle 3401 are drawn in a direction towards the bone as the hole is formed, the distal end of the depth sleeve member 3404 remains in contact with the exterior surface of the bone along the periphery of the opening of the hole and is essentially pushed in an opposing direction toward the handle 3401, such that the portion of the depth sleeve member 3404 at or near the proximal end thereof pushes upon the sleeve spring 3405, thereby compressing the sleeve spring 3405. Such movement of the depth sleeve member 3404 is measured in real-time (i.e., as the awl-tap member advances into bone) via a depth measurement sensor operably associated with the depth sleeve member 3404. In particular, a depth measurement sensor operably associated with the sleeve member 3404 senses movement of the sleeve member 3404 relative to the awl-tap member 3406 and handle 3401 and is configured to generate an electronic signal in response to the movement sensed. The sensor is able to account for the length of distal tip 3408 protruding from the distal end of sleeve member 3404, at the initial default resting position, when generating a signal indicating the depth measurement.

The depth measurement sensor assembly includes a sleeve contact 3444 coupled to an exterior surface of depth sleeve collar 3442. The sleeve collar 3442 is coupled to a proximal end of depth sleeve member 3404, resting on an upper surface of a flange of the depth sleeve member 3404, and within the handle 3401. The sensor assembly senses lateral movement of the depth sleeve member 3404 relative to handle 3401 and the awl-tap member 3406 by sensing contact between the sleeve contact 3444 and depth gauge electronics and/or circuitry provided on a printed circuit board (PCB) 3440 enclosed within the handle 3401. In particular, the sensor assembly may include inductive or capacitive elements or assemblies configured to sense movement of the sleeve contact 3444 based on a relative change in the contact position of sleeve contact 3444 and associated inductive or capacitive elements or assemblies of the PCB 3440. It should be further noted that the handheld device 3400 is a standalone device that is battery-operated (battery 3450). The battery 3450 may include, for example, a 3.7 volt lithium ion polymer battery. The battery may be rechargeable by way of micro-USB, or other means. As shown, a display 3420 may be provided on the handle 3401 and configured to visually provide a digital readout of a depth measurement of the hole based on the electronic signal from the depth measuring sensor assembly. Thus, the depth measurement of the hole may be determined and visually displayed on a display 3420 of the handheld device 3400 in real-time or near real-time, as the awl-tap member 3406 is advancing into bone and forming a hole therein. Display 3420 may also be configured to provide other data, including, but not limited to, information related to neuromonitoring and/or neurostimulation procedures (e.g., nerve location/sensing feedback, a level of electricity being transmitted to nerves from an awl-tap member 3406, etc.), a charge level of the battery, and the like. In some embodiments, the handheld device 3400 may be configured to wirelessly communicate and exchange data with a separate display or computing device, such as, for example, a monitor or panel display, a PC, a notebook, a tablet computer, a smartphone, or other wireless computing device.

With the same handheld device 3400, the surgeon may also visually receive real-time or near real-time feedback concerning the location of nerves adjacent to the hole as it is formed, and throughout the bone fixation procedure. The neuromonitoring feedback can inform repositioning of the awl-tap member 3406 during penetration into the bone, if there is any sensing of nearby nerves, thereby ensuring a properly formed hole and subsequently ensuring proper positioning of a screw within the hole so as to avoid inadvertent piercing, breaching, damage, or impinging upon unintended structures or tissues. In addition, without removing device 3400 from the hole, the surgeon may further perform neurostimulation of nerves adjacent to the hole and receive digital feedback of the level of electricity transmitted to the nerves in real-time or near real-time. The surgeon may also adjust a level of electricity used for neurostimulation or neuromonitoring features on the device 3400 itself, in the sterile environment. For example, the handle 3401 may further include a switch 3452 for adjusting a level of electricity (e.g., a current level) used for neurostimulation or neuromonitoring by the handheld device. In one embodiment, the switch 3452 is a three-position switch, but any switch suitable to adjust a level of electricity used for neurostimulation or neuromonitoring by the handheld device 3400 may be used. Thus, device 3400 provides the surgeon with a single disposable device for performing a bone fixation procedure while receiving visual digital feedback throughout, and the ability to control neurostimulation or neuromonitoring features from within the sterile environment, without relying on a specialist to carry out the monitoring operation. Accordingly, a surgeon performing a bone fixation procedure may receive real-time or near real-time feedback from the information visually shown on display 3420 of device 3400, and may use the information displayed to accurately determine the depth of a hole and to inform selection of a screw having a corresponding length.

To perform at least the neurostimulation and neuromonitoring functions, the handheld device may be coupled to and placed in electrical connection with an input connector of a neuromonitoring device via a cable. The neuromonitoring device may include a junction box configured to carry electrical current to and from the input connector and the handheld device. The junction box includes a processor configured to generate and transmit electrical current to and from the input connector, and the handheld device. For example, the processor may be configured to generate and transmit a pulse of electricity to the awl-tap member, while positioned within a hole, to perform neuromonitoring of nerves adjacent to the hole. In addition, certain electrodes inserted into muscles of the patient may be used to detect a current flow from the awl-tap member to an electrode, indicating a completed circuit between the awl-tap member and the electrode, wherein such current flow is indicative of the presence of a nerve adjacent to the hole by detecting electrical activity at a muscle enervated by the nerve stimulated by the awl-tap member. The processor of the junction box is operably connected to the input connector, electrode inputs, and one or more PCBs. The one or more PCBs may include a pulse or current generating circuit configured to generate and transmit electrical current to the handheld device, a current generating confirmation circuit configured to detect electrical current transmitted from the device to nerves, a muscle movement detection circuit configured to detect muscle movement in response to neurostimulation or neuromonitoring functions, and an electrode disconnection detection circuit configured to detect partial or total disconnection of an electrode from the junction box or the patient, or improper insertion of an electrode into the patient.

Figure 36:
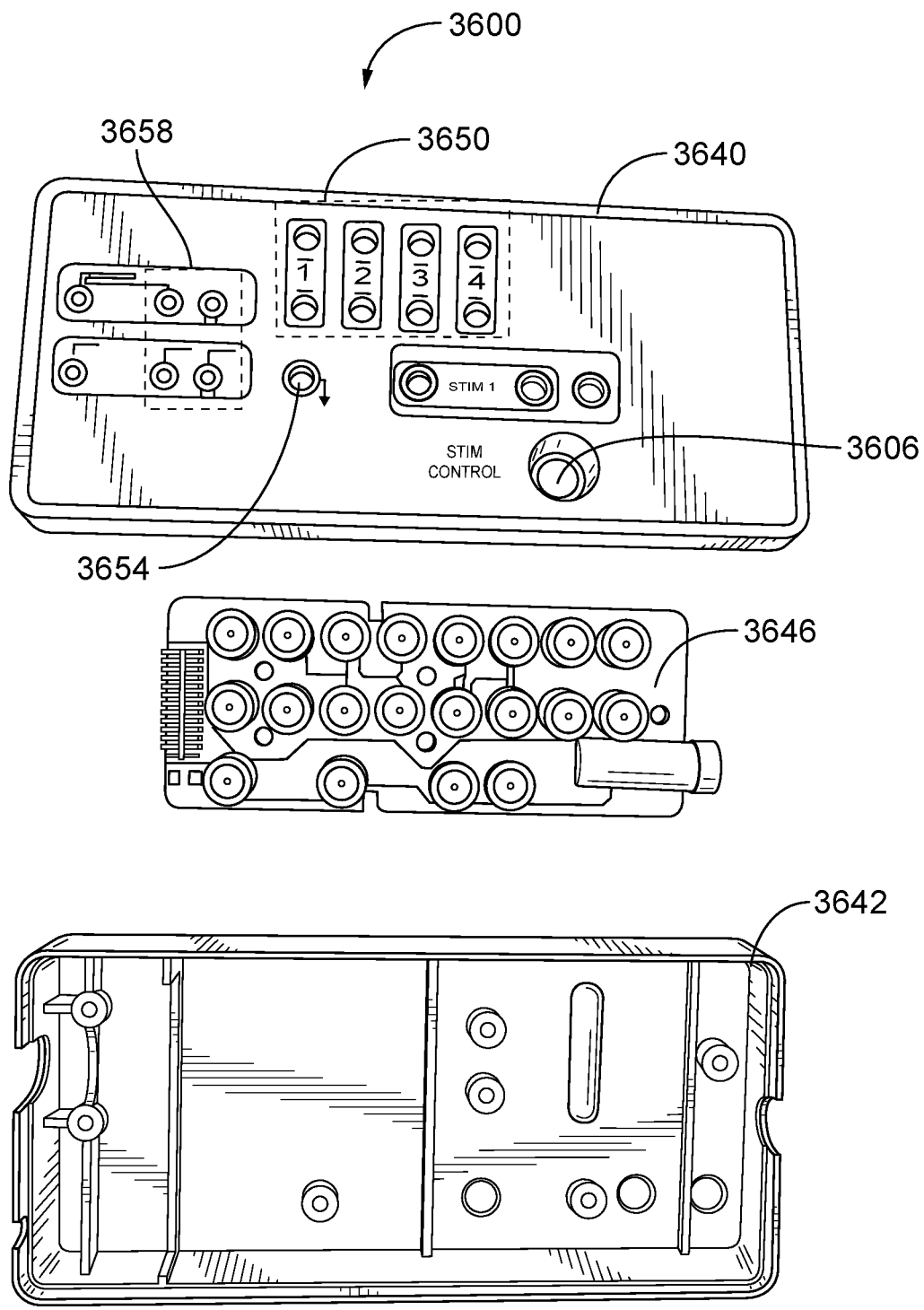
FIG. 36 is an exploded view of an exemplary neuromonitoring device for use with the handheld device of the present disclosure and illustrating components thereof.

FIG. 36 is an exploded view of a neuromonitoring device 3600, illustrating components thereof. The neuromonitoring device 3600 includes a front housing 3640 and a back housing 3642, together enclosing a PCB 3646 operably connected to a processor (not shown). For example, the processor may be a microprocessor configured to communicate electrical current to and from at least an input connector 3606. The front housing 3640 may include a graphic overlay to indicate the position at which various connectors and electrodes may be connected. In this example, neuromonitoring device 3600 may be connected to at least an input connector 3606, sensing electrodes 3652, a ground electrode 3654, and a return electrode 3658. The electrodes may be placed in electrical connection with the neuromonitoring device by connecting the electrodes to electrode inputs of the neuromonitoring device. As shown, front housing 3640 and back housing 3642 are secured together, with PCB 3646, a processor, and other components housed therein, by screws or fasteners. It should be noted that the neuromonitoring device 3600 includes an indicator feature for providing a user with an indication as to whether the neuromonitoring device 3600 is properly set up and functioning as intended, particularly with regard to the electrode set up. In particular, the neuromonitoring device 3600 is configured to identify whether the sensing electrodes 3652, a ground electrode 3654, and a return electrode 3658 are plugged in and further functioning properly or are unplugged or experiencing issues (i.e., improper transmission of signals or the like). The neuromonitoring device 3600 is configured to provide a visual indication of the status of the electrode set up and functioning. For example, in one embodiment, the neuromonitoring device 3600 may provide a green light indicating that the electrode set up and functioning is acceptable and a red light indicating that there is an issue with the electrode set up or functioning.

In this illustration, neuromonitoring device 3600 may be electrically coupled to at least a ground electrode 3654, a return electrode 3658, sensing electrodes 3652, and input connector 3606. For example, neuromonitoring device 3600 may be electrically connected to two, four, six, eight, or more than eight pairs of sensing electrodes 3652. The number of sensing electrodes 3652 used may be selected according to the procedure intended, the muscle involved, the injury being treated, or other patient or procedure-related parameters. During a procedure, each pair of sensing electrodes may be inserted into muscles of a patient, usually in a configuration having one electrode of the pair inserted on one side of the muscle, and the other electrode of the pair inserted on the opposite side of the muscle. Once the sensing electrodes are inserted into the muscle, the sensing electrodes are connected to neuromonitoring device 3600, and an electrode selection switch of neuromonitoring device 3600 may be switched to a position corresponding to the number of sensing electrodes used.

A ground electrode 3654 may be inserted into a different body part of the patient, preferably near the buttocks, and does not have to be inserted into a muscle. The ground electrode 3654 is subsequently connected to neuromonitoring device 3600. A return electrode 3658 may be inserted near or into an incision area of the patient, at which a hole is to be formed in a bone or is already formed. The return electrode is subsequently connected to neuromonitoring device 3600. The neuromonitoring device 3600 may then be electrically connected to the handheld device 3400 as described herein by connecting a cable between input connector 3606 and the handheld device.

While a hole is being formed by the awl-tap member of the handheld device, or post formation, neuromonitoring device 3600 may generate and transmit electrical current that is carried to the handheld device 3400 for neurostimulation or neuromonitoring of nerves adjacent or in close proximity to the awl-tap member when positioned within a hole. In one example, the electrical current is carried from input connector 3606 through a cable to the electrically conductive body of the awl-tap member to provide neurostimulation or neuromonitoring features. In some embodiments, portions of the awl-tap member body may be insulated (i.e., include a coating of insulating material or include a layer or outer jacket of insulating material) while other portions are left uninsulated. In turn, electrical current transmitted to the handheld device 3400 will travel through the awl-tap member and be emitted from the uninsulated portions. For example, in some embodiments, the distal tip of the awl-tap member may be uninsulated and thus the electrical current is emitted therefrom. In other embodiments, only the external threading portion of the awl-tap member is uninsulated, while the remaining portions of the awl-tap member are insulated (i.e., the remaining length of the awl-tap member and the distal tip of the awl-tap member). As a result, electrical current is delivered from the awl-tap member to the surrounding bone during a hole formation procedure and any nerves within the bone and adjacent to the awl-tap member may be stimulated by the electrical current. Nerve stimulation can be performed at 0.5, 5 and 20 ma, for example. It should be noted that, in some embodiments, the handheld device 3400 itself may generate the electrical current from an internal source incorporated into the handheld device and thus does not rely upon the neuromonitoring device 3600 for electrical current.

During neurostimulation, the sensing electrodes 3652 may be used to monitor the patient's muscles for feedback. The processor of neuromonitoring device 3600 is configured to generate and transmit a control signal to adjust a level of electricity stimulating a nerve in response to the control signal. For example, the processor may be configured to generate a control signal to increase, decrease, or stop current flow to the awl-tap member when a predetermined level of electricity is sensed by sensing electrodes 3652. In this example, if the processor of neuromonitoring device 3600 determines that the level of electricity transmitted from neuromonitoring device 3600 to the awl-tap member is greater than a pre-determined level, the processor may then generate and transmit a control signal to decrease the current flow to the awl-tap member. As previously described, the handheld device may also include a switch or other control device to adjust the level of electricity transmitted from the awl-tap member to the nerves. The switch or control device communicates with the processor of the neuromonitoring device 3600 to cause the processor to generate and transmit a control signal to adjust the level of electricity transmitted from the awl-tap member. The processor of neuromonitoring device 3600 may be further configured to generate and transmit a signal to a display of the handheld device to cause the display to visually indicate the level of electricity stimulating a nerve, any abnormalities in current flow, or other like information.

Neuromonitoring functions may be performed by inserting return electrode 3658 into the open exposed tissue of a surgical site at which the bone fixation procedure is being performed, or into tissue near or adjacent to the surgical site. A pulse of electricity or a current is supplied to nerves adjacent to the hole by the awl-tap member. The pulse of electricity is carried from neuromonitoring device 3600 by a cable connecting the neuromonitoring device to the handheld device 3400. Thus, neuromonitoring may be performed by enervating a nerve adjacent to the awl-tap member when the awl-tap member is within a hole that is formed or is being formed and detecting a current in a muscle enervated by the nerve. Detection of a current indicates that a circuit has been created between the awl-tap member and return electrode 3658. Accordingly, if a current is detected, then a nerve is too close to the hole. The processor of neuromonitoring device 3600 is also configured to generate and transmit a signal to a display of the handheld device so that the display visually indicates the presence of a nerve adjacent to the hole and other related information. The surgeon may use the information displayed to inform repositioning of the awl-tap member, during formation of the hole, if there is any sensing of nearby nerves. This real-time or near real-time feedback of nerves sensed adjacent to the hole ensures a properly formed hole and subsequently ensures proper positioning of a screw within the hole so as to avoid inadvertent piercing, breaching, damage, or impinging upon unintended structures or tissues.

In some embodiments, the processor of neuromonitoring device 3600 is further configured to receive electrical signals from a sensor coupled to a depth sleeve member of the handheld device. The sensor is configured to generate an electronic signal indicative of a depth of the hole as a result of sensing movement (i.e., distance traveled) of the sleeve relative to the handle of the handheld device when the distal end of the sleeve abuts an exterior surface of bone along a periphery of an opening of a hole to be formed via the awl-tap member of a hole and is pushed upward and into the handle as the distal tip of the awl-tap member advances into the hole as described above. The processor of neuromonitoring device 3600 is also configured to generate and transmit a signal to a display of the handheld device to visually indicate the depth of the hole.

Figure 37:
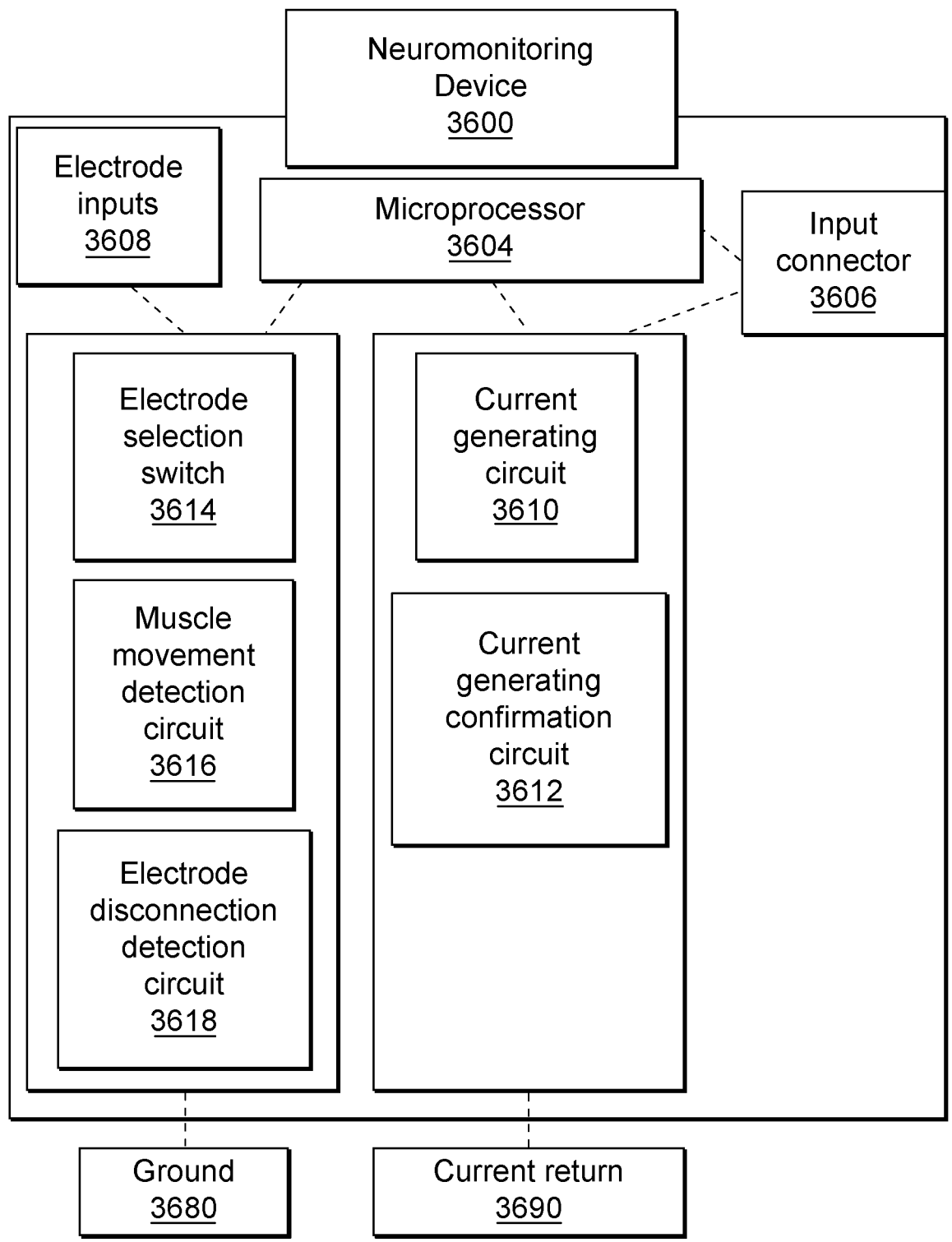
FIG. 37 is a schematic illustration of an exemplary neuromonitoring device for use with the handheld device of the present disclosure.

FIG. 37 is a schematic illustration of a neuromonitoring device 3600 for use with the handheld device 3400 of the present disclosure. As shown, neuromonitoring device 3600 includes a microprocessor 3604 operably coupled to an input connector 3606 for electrically connecting neuromonitoring device 3600 to the handheld device as described herein, and electrode inputs 3608. Microprocessor 3604 is operably coupled to one or more PCBs which include a pulse or current generating circuit 3610 and a current generating confirmation circuit 3612 that is connected to a current return 3690. Microprocessor 3604 is also operably coupled to one or more PCBs which include a muscle movement detection circuit 3616 connected to ground 3680, and an electrode disconnection circuit 3618 connected to ground 3680.

The pulse or current generating circuit 3610 is configured to generate and transmit electrical current to a handheld device 3400 for neurostimulation or neuromonitoring functions, as previously described herein. The pulse or current generating confirmation circuit 3612 is configured to detect electrical current transmitted from the awl-tap member of the handheld device. The current generating circuit 3610 and the current confirmation circuit 3612 are operably coupled to current return 3690, which is configured to detect a return current present between the awl-tap member and a return electrode.

The electrical current generated by the current generating circuit 3610 may be carried to the handheld device as described herein, by a cable electrically connected to input connector 3606, and the electrical current may be used for neurostimulation or neuromonitoring of nerves adjacent to a hole. For example, the current generating circuit 3610 may include an adjustable constant current source, a step up transformer, and other electrical components depending on the intended use, including transformers, transistors, diodes, capacitors, resistors, potentiometers, and one or more switches having multiple positions to adjust parameters of the pulse or current generated or transmitted. In another example, the current generating confirmation circuit 3612 may include a current detection chip configured to detect a current generated by the current generation circuit and transmit a signal to the processor in response to the current detected. The processor 3604 is also configured to generate and transmit a signal to the display of the handheld device to cause the display to visually indicate a level of electricity transmitted from the awl-tap member of the handheld device, as well as whether any nerves are present and adjacent to the awl-tap member.

The muscle movement detection circuit 3616 is configured to detect electrical activity of a muscle enervated by electrical current transmitted to a hole from the current generating circuit 3610. The movement detection circuit 3616 may include an analog-to-digital converter (ADC) that converts an analog signal received by neuromonitoring device 3600 into a multi-level digital signal readable by the processor.

The electrode disconnection detection circuit 3618 is operably connected to ground 3680 and is configured to detect partial or total disconnection of an electrode from neuromonitoring device 3600, or improper insertion of an electrode into a patient. Processor 3604 may be configured to generate and transmit a signal to the display of the handheld device to indicate such a partial or total disconnection of an electrode. In one example, the electrode disconnection detection circuit 3618 may include a lead off chip to detect partial or total disconnection of the electrode.

Figure 38:
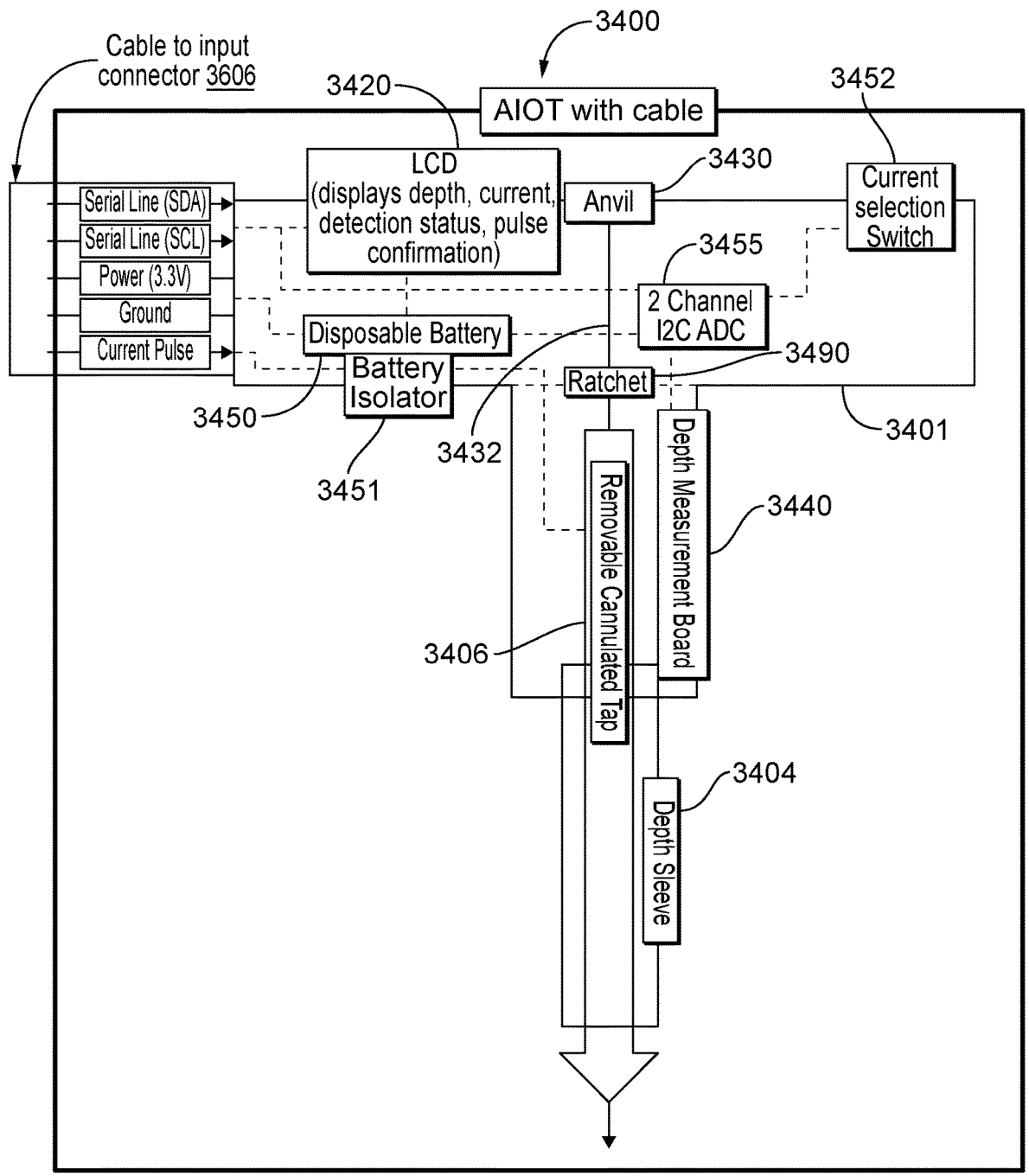
FIG. 38 is a schematic illustration of the handheld device.

FIG. 38 is a schematic illustration of the handheld device 3400 consistent with the present disclosure. As shown, handheld device 3400 includes a handle having a display 3420, a current selection switch 3452, and a battery 3450 connected to a removable battery isolator 3451. During operation, the battery isolator 3451 is first removed to allow current flow to and from the battery 3450 and other electrical components of device 3400. In one example, current selection switch 3452 may be used to adjust a current flow between a neuromonitoring device and device 3400, in particular, awl-tap member 3406. Device 3400 includes a ratchet assembly 3490 that rotatably couples the handle 3401 and the awl-tap member 3406 and allows for a ratcheting movement of the handle 3401 and awl-tap member 3406 relative to one another. The ratchet assembly 3490 is described in detail below with reference to FIGS. 39-41. As shown, awl-tap member 3406 has a stylet 3432 removably positioned within a hollow inner channel of the awl-tap member to prevent bone debris or other tissues from entering the inner channel as the distal tip of the awl-tap member 3406 is advanced into a hole. The stylet 3432 may be coupled to an anvil 3430 at a proximal end, which facilitates inserting and removing the stylet from the inner channel. As previously described, the body of the awl-tap member 3406 is electrically conductive and is operable to carry electrical current for neurostimulation and neuromonitoring functions.

The handheld device 3400 also includes depth sleeve member 3404, through which the awl-tap member 3406 extends along the length of. Sleeve member 3404 has a sleeve collar connected to its tubular body and the sleeve collar has a sleeve contact connected to its exterior surface. The sleeve contact contacts depth measuring board 3440, which may include a PCB. As sleeve 3404 moves relative to the awl-tap member 3406 and handle 3401 in a lateral orientation (as opposed to rotational movement), the contact position between the sleeve contact and the depth measuring board 3440 will change, and an electrical signal is carried from the depth measuring board 3440 to an ADC converter 3455. Analog electrical signals are converted to digital signals by ADC converter 3455. These digital signals may be used by the display 3420 to provide the surgeon with a visual representation of a depth measurement of the hole. The electrical signals from ADC converter 3455 may optionally be transmitted to a neuromonitoring device, such as that described with reference to FIGS. 36 and 37, via a cable electrically connected between the input connector 3606 of the neuromonitoring device and handheld device 3400. In this example, the single cable includes a current pulse line that carries electrical current to awl-tap member 3406, a power line and a ground line connected to battery 3450, a serial data line for transmitting and receiving data between ADC converter 3455 and the input connector 3606, and a serial clock line for synchronizing data transfers from ADC converter 3455 to other components of the handheld device or the neuromonitoring device.

Figure 39:
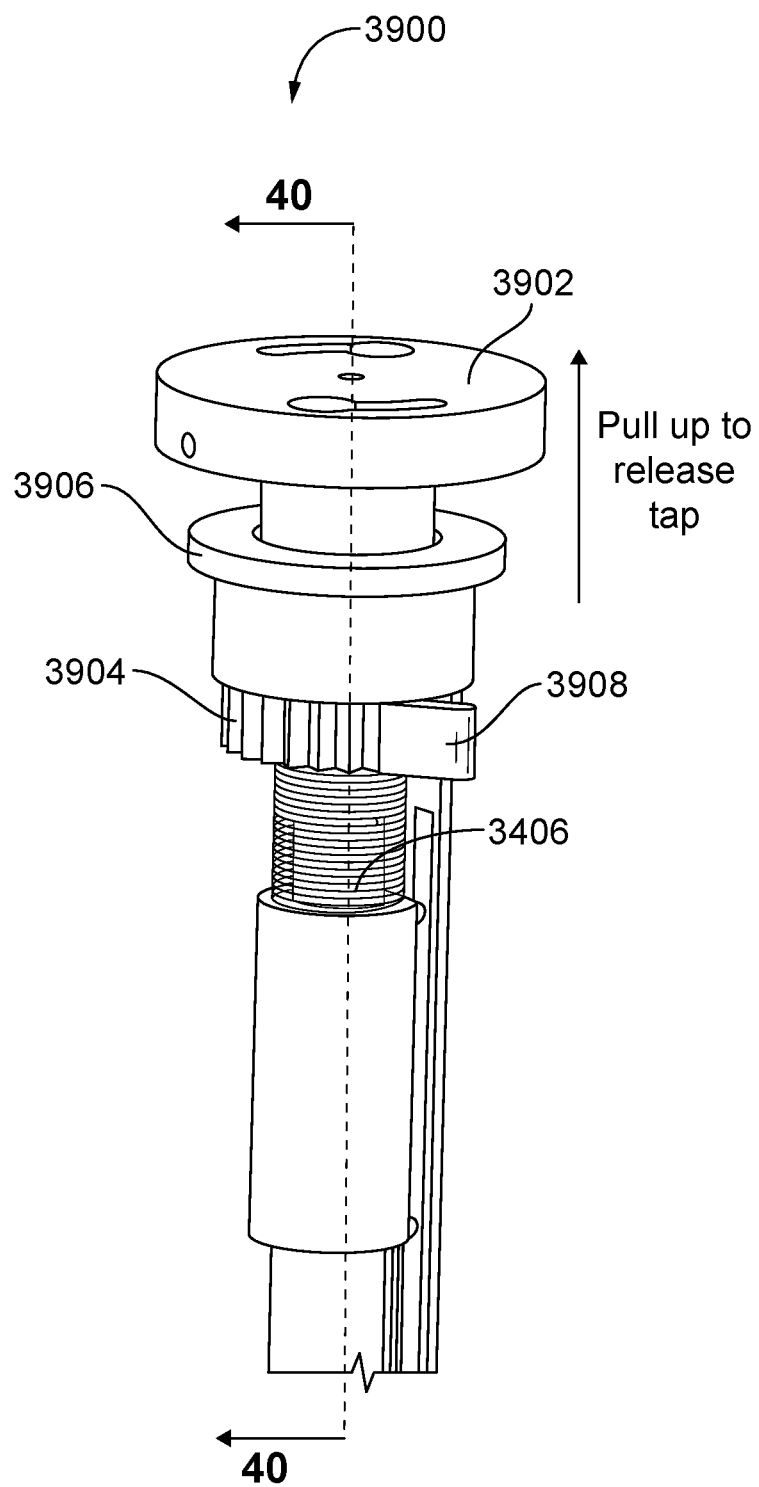
FIG. 39 is a perspective view of a ratchet assembly for use with the handheld device of the present disclosure.
Figure 40:
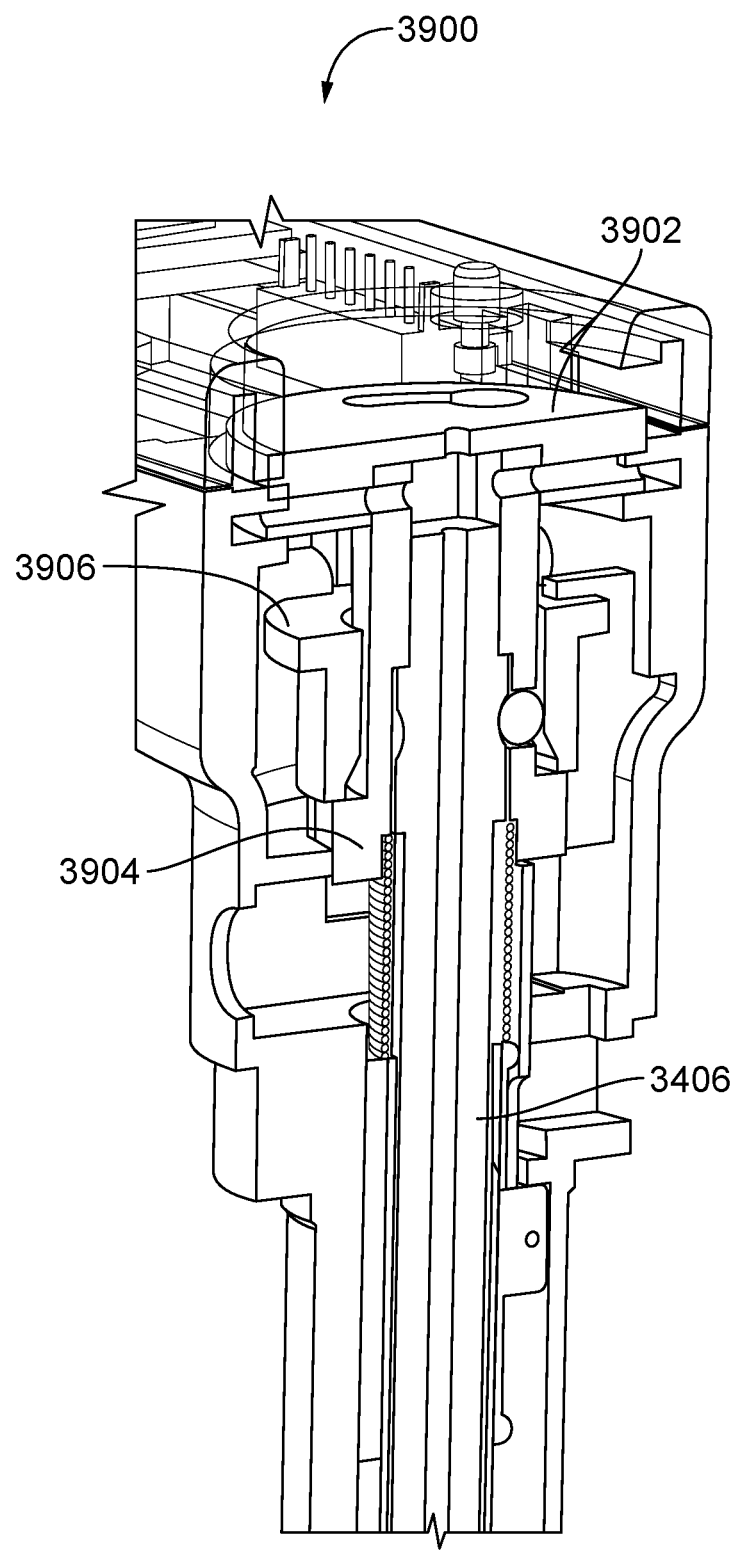
FIG. 40 is a cross-sectional view of the ratchet assembly taken along lines 40-40 of FIG. 39.

As previously described, the handheld device 3400 further includes a ratchet assembly that rotatably couples the handle 3401 and the awl-tap member 3406 to one another. FIG. 39 is a perspective view of an exemplary ratchet assembly 3900 for use with the handheld device 3400 of the present disclosure. FIG. 40 is a cross-sectional view of the ratchet assembly 3900 taken along lines 40-40 of FIG. 39.

The ratchet assembly 3900 provides ratcheting action which results in the awl-tap member 3406 advancing into or withdrawing from bone during hole formation. For example, the ratchet assembly 3900 includes a toothed gear 3904, at least one pawl 3908, and a collar 3902 coupled to the handle 3401 of the handheld device 3400. The ratchet assembly 3900 is rotatably coupled to at least a portion of the body of the cannulated awl-tap member 3406. The ratchet assembly 3900 is also operably coupled to a lock ring 3906, such that the lock ring prevents rotation of the toothed gear 3904. The toothed gear 3904 has teeth spaced about the perimeter of the gear, and a minimum diameter between opposing teeth. The toothed gear 3904 may have any number of teeth and may have any minimum diameter between such teeth as long as the toothed gear is suitable for operation as described herein. Preferably the toothed gear may have 24, 22, 20, or less than 20 teeth. As shown, pawl 3908 is positioned tangent to the minimum diameter such that a distal end of the pawl 3908 engages the gear 3904 and prevents further rotation of the gear 3904 in a second direction opposite the first direction. The ratchet assembly 3900 further includes a switch allowing a user to toggle between a first rotation setting and a second rotation setting.

In the first rotation setting, rotation of the handle 3401 in a first direction results in the awl-tap member 3406 rotating in the same direction while rotation of the handle 3401 in an opposite second direction is independent of any rotation of the awl-tap member 3406 (i.e., the awl-tap member 3406 remains stationary). As such, rotation of the awl-tap member 3406 in the first direction may cause the distal tip 3408 of the awl-tap member 3406 to penetrate and be drawn into the bone (via the external threading). In the second rotation setting, rotation of the handle 3401 in the first direction is independent of any rotation of the awl-tap member 3406 (i.e., the awl-tap member 3406 remains stationary) while rotation of the handle 3401 in the opposite second direction results in the awl-tap member 3406 rotating in the same direction. As such, rotation of the awl-tap member 3406 in the second opposite direction may cause the distal tip 3408 of the awl-tap member 3406 to withdraw from the hole. For example, a pawl 3908 may be configured to allow rotation of the handle and awl-tap member 3406 in a clockwise direction, but prevent rotation in a counterclockwise direction, or vice versa. In this example, pawl 3908 allows rotation of awl-tap member 3406 in a first direction corresponding to rotation of the handle 3401 in the first direction, but does not allow corresponding rotation of the awl-tap member 3406 when the handle 3401 is rotated in the second opposite direction. The collar 3902 is configured to disengage the pawl 3908 from gear 3904 to allow rotation in the second direction. Accordingly, once a desired depth of a hole is reached by the distal tip 3408 of cannulated awl-tap member 3406, collar 3902 may be pulled toward the proximal end of the awl-tap member 3406 to disengage pawl 3908 from toothed gear 3904, thereby releasing gear 3904 such that rotation of the handle 3401 in the second direction results in corresponding rotation of the awl-tap member 3406, resulting in withdrawal of the distal tip 3408 of the awl-tap member 3406.

Figure 41:
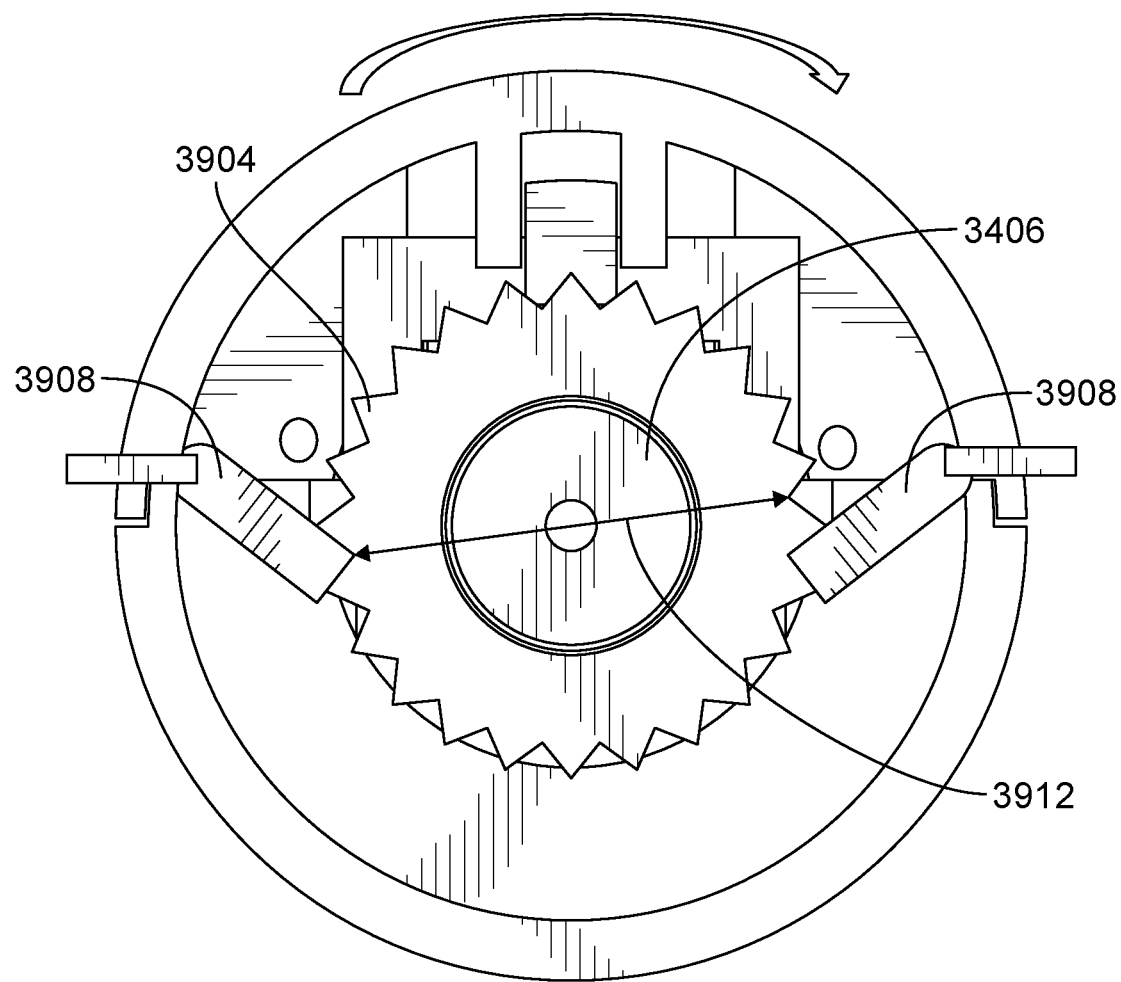
FIG. 41 is a plan view of a portion of the ratchet assembly illustrating operation of the gear and pawls.

FIG. 41 is a plan view of a portion of the ratchet assembly 3900, illustrating operation of the toothed gear and pawls. As shown, ratchet assembly 3900 includes a toothed gear 3904 having a minimum diameter 3912 between opposing teeth on opposite sides of the diameter of the gear, and pawls 3908 on opposing sides of the gear. In this example, toothed gear 3904 has twenty-four teeth, but a toothed gear having a greater or lesser number of teeth suitable for operation as described herein may be used. Awl-tap member 3406 extends through an inner bore of the toothed gear 3904 such that rotation of a handle 3401 of the handheld device 3400 rotates the cannulated awl-tap member 3406 as well as gear 3904. As described above, a collar of the ratchet assembly may be pulled toward the proximal end of the cannulated awl-tap member to disengage one or both pawls 3908 from minimum diameter 3912 to allow rotation in the opposite direction. Such rotation in the opposite direction withdraws the distal tip of the cannulated awl-tap member from the hole, and a screw or other fastener may subsequently be placed into the hole to secure a bone plate to the bone.

Figure 42:
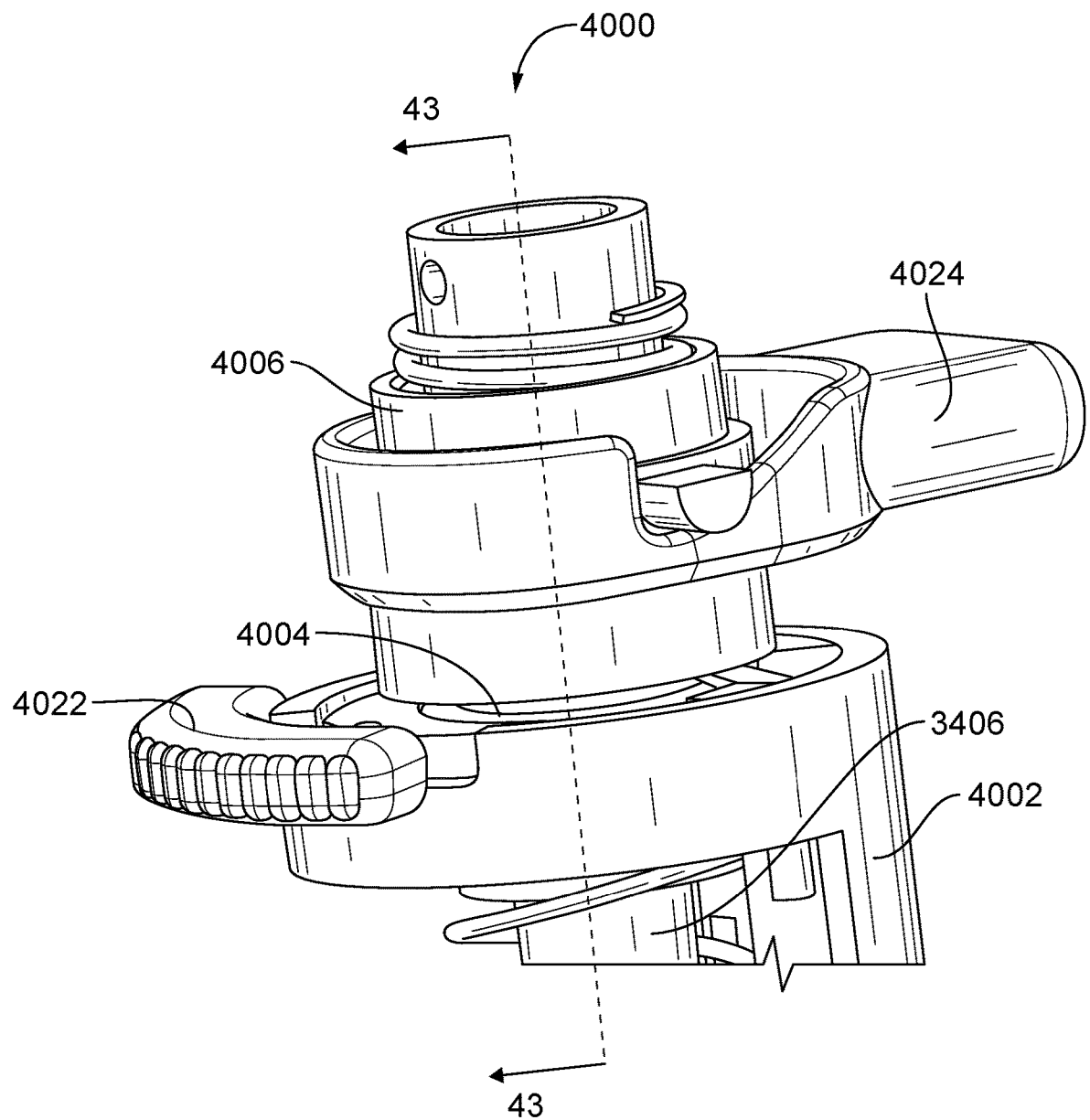
FIG. 42 is a perspective view of a ratchet assembly for use with the handheld device of the present disclosure.
Figure 43:
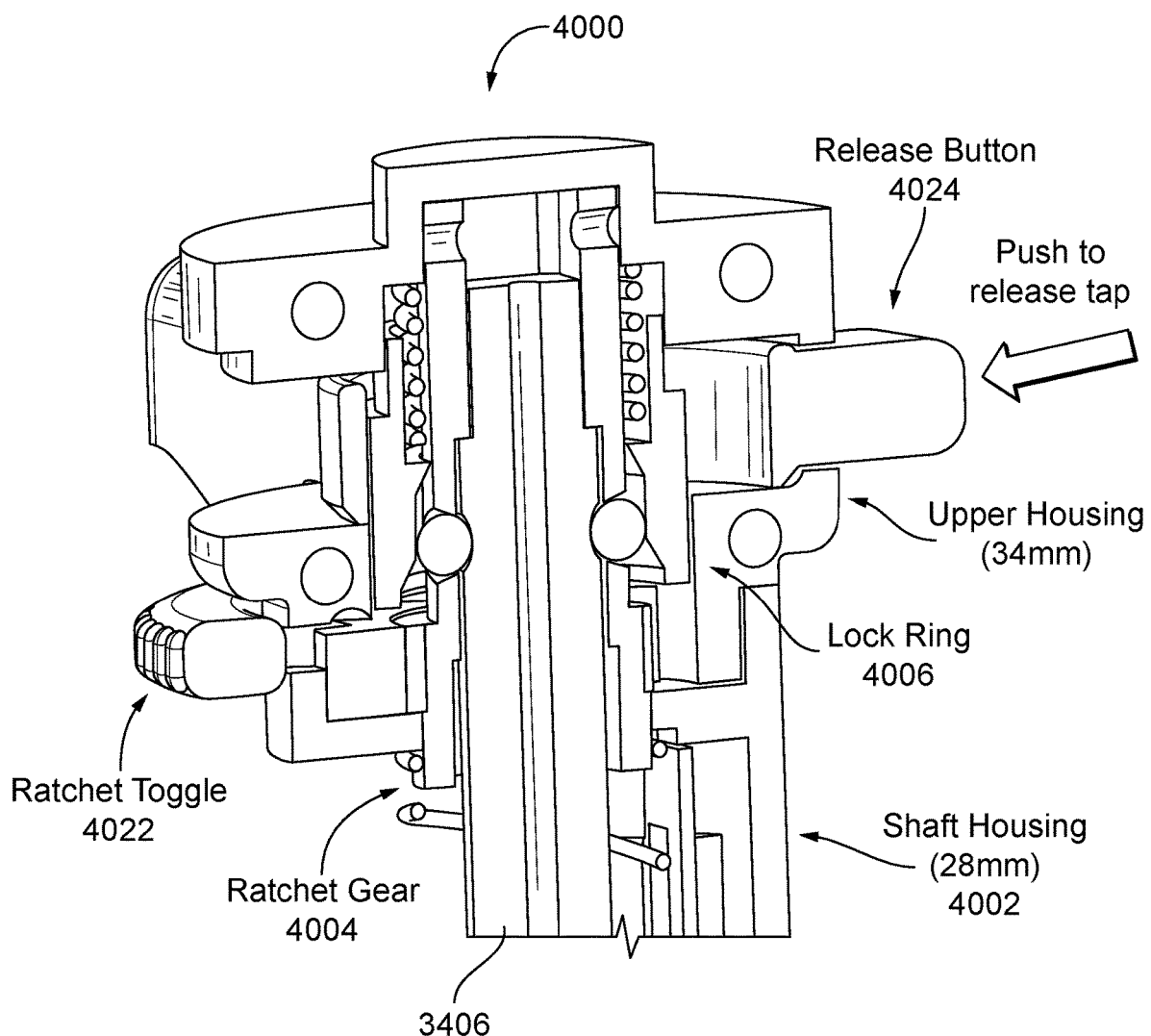
FIG. 43 is a cross-sectional view of the ratchet assembly taken along lines 43-43 of FIG. 42.
Figure 44:
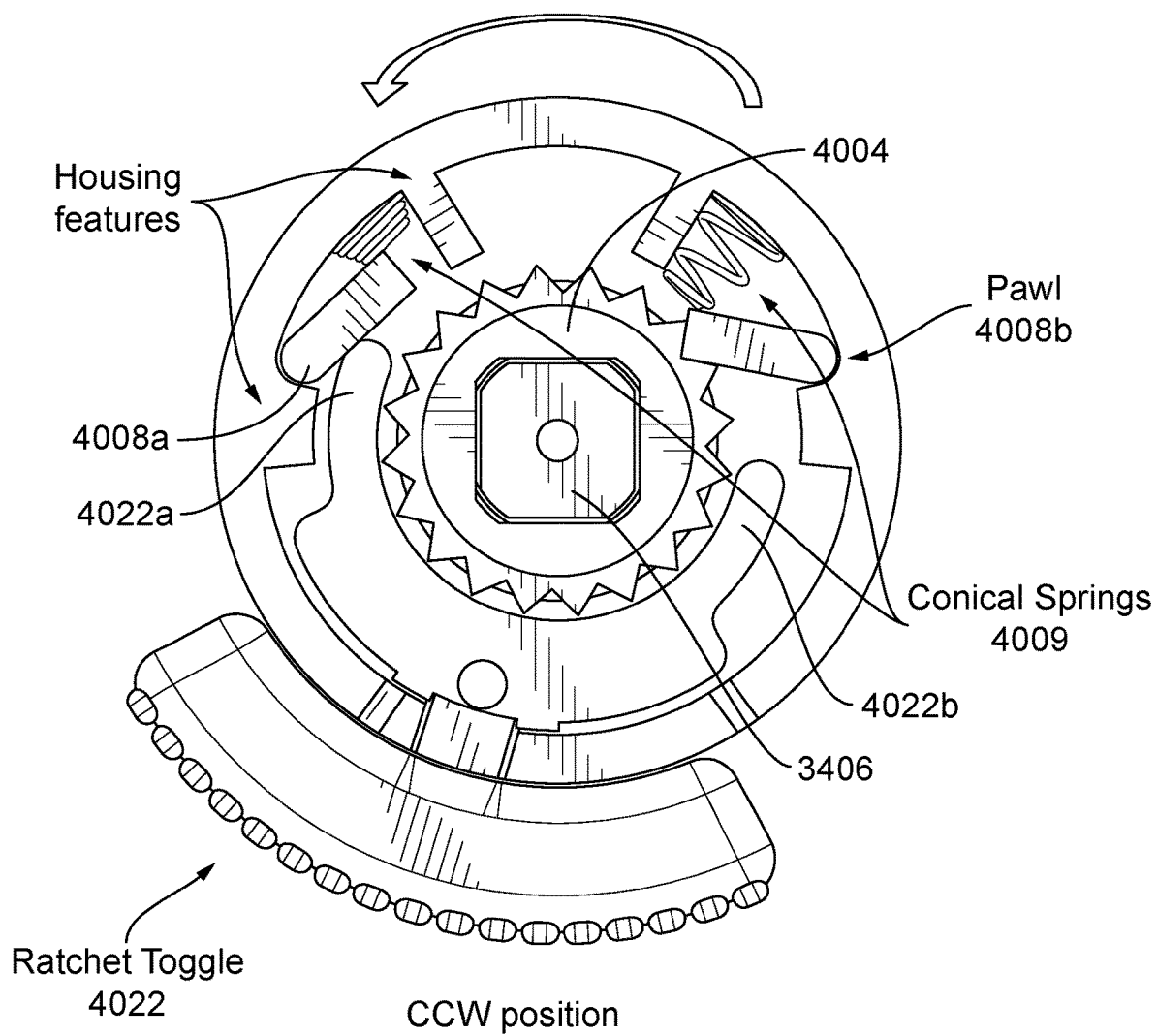
FIG. 44 is a plan view of a portion of the ratchet assembly, illustrating operation of the gear and pawls.

FIG. 42 is a perspective view of another embodiment of a ratchet assembly 4000 for use with the handheld device 3400 of the present disclosure. FIG. 43 is a cross-sectional view of the ratchet assembly 4000 taken along lines 43-43 of FIG. 42. As shown, ratchet assembly 4000 includes a toothed gear 4004 and two pawls (as shown in FIG. 44). The ratchet assembly 4000 is also operably connected to a lock ring 4006, and a release button 4024, such that pressing the button 4024 toward its distal end and in the direction of the lock ring 4006 results in the lock ring being pushed upward due to the inclined curvature of the connection between the lock ring 4006 and the button 4024. When the lock ring 4006 is pushed upward and toward a handle that is rotatably coupled to a proximal end of the ratchet assembly 4000, the handle is released and is able to freely rotate. As shown, ratchet assembly 4000 is also coupled to cannulated awl-tap member 3406, such that rotation of the handle also results in rotation of the awl-tap member 4020. The awl-tap member 4020 extends through an inner channel of the toothed gear 4004. In this example, toothed gear 4004 is coupled to awl-tap member 4020 within handle 4002.

In this example, ratchet assembly 4000 also includes a ratchet toggle 4022, which is slidably mounted about at least a portion of the perimeter of the toothed gear 4004. Ratchet toggle 4022 may be rotated or slid in a first or a second direction opposite to the first direction to disengage a pawl of the ratchet assembly 4000 and allow rotation of the toothed gear 4004 in the direction of the disengaged pawl.

FIG. 44 is a plan view of a portion of the ratchet assembly 4000, illustrating operation of the gear and pawls. As shown, ratchet assembly 4000 includes a toothed gear 4004 having an inner channel through which awl-tap member 3406 extends, pawls 4008a and 4008b, and a toggle 4022. Each of pawls 4008a and 4008b are biased by springs 4009, such that engagement between a distal end of pawls 4008a and 4008b and springs 4009 biases the distal end of each pawl toward toothed gear 4004, thereby engaging the teeth of toothed gear 4004 and preventing gear 4004 from rotation in the direction of the pawl. In this example, toothed gear 4004 has approximately twenty teeth spaced about the perimeter of the gear and has a minimum diameter between opposing teeth. The toothed gear 3904 may have any number of teeth and may have any minimum diameter between such teeth as long as the toothed gear is suitable for operation as described herein. Pawls 4008a and 4008b engage toothed gear 3904 at the minimum diameter of the gear.

Toggle 4022 is shown at a position that allows counterclockwise rotation of the handle of a handheld device and corresponding rotation of the awl-tap member 3406 according to rotation of the handle. In this position, toggle 4022 has been slid or rotated in a clockwise direction. The left arm 4022a of toggle 4022 is shown engaging pawl 4008a and pushing the distal end of pawl 4008a toward spring 4009, thereby disengaging pawl 4008a from toothed gear 4004 and allowing the toothed gear to rotate in a counterclockwise direction. Conversely, pawl 4008b is not engaged with the right arm 4022b of toggle 4022 and the distal end of pawl 4008b is shown engaged with toothed gear 4004, preventing toothed gear 4020 from rotation in a clockwise direction.

Figures 45, 46:
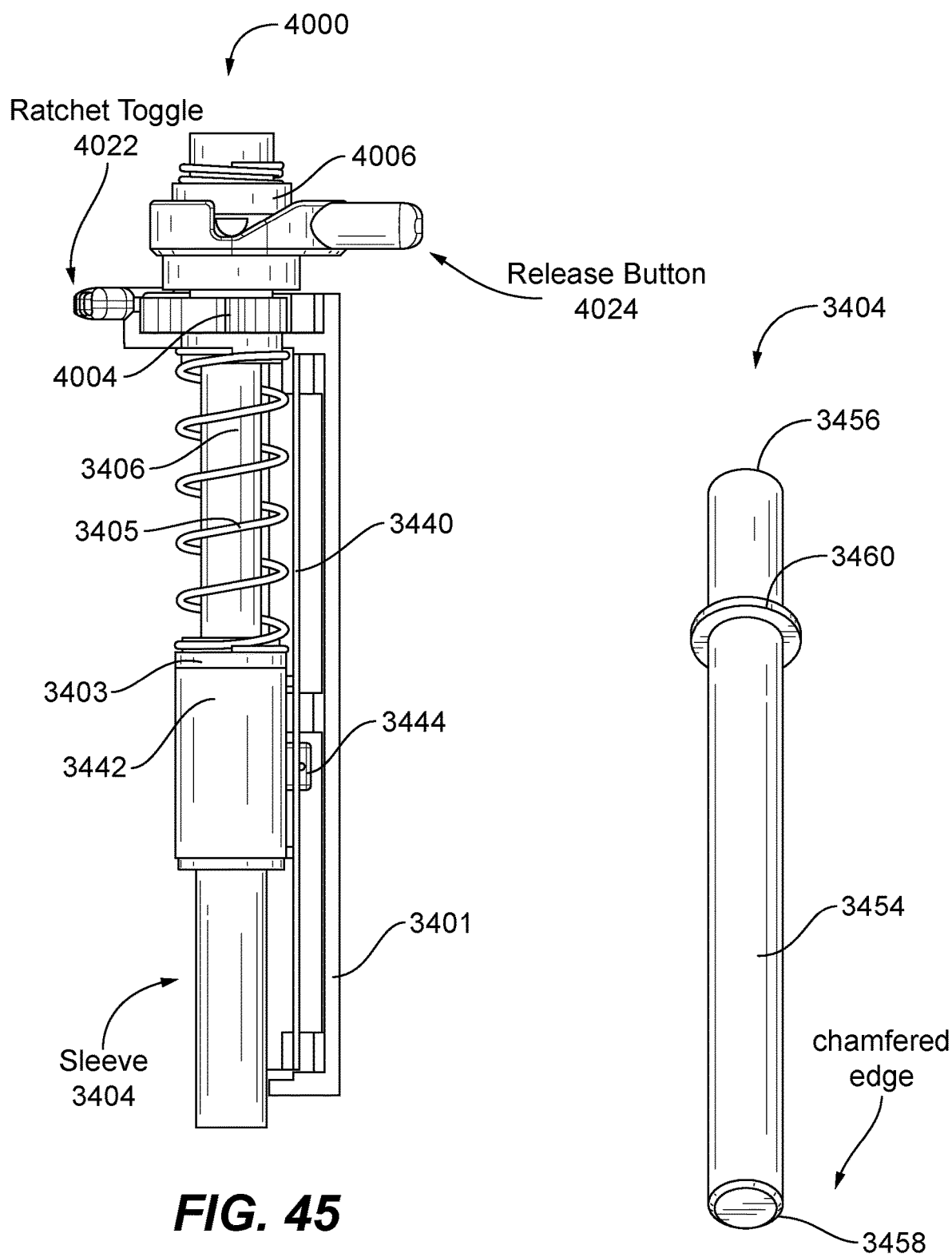
FIG. 45 is a perspective view of a ratchet assembly consistent with the present disclosure.
FIG. 46 is a perspective view of a depth sleeve member having a tubular body with a distal end including a chamfered edge.

FIG. 45 is a perspective view of the ratchet assembly 4000 in which at least a portion of the ratchet assembly 4000 is housed within the handle 3401 of the handheld device 3400. As shown, ratchet assembly 4000 is operably coupled to the tubular body of the awl-tap member 3406. Ratchet assembly 4000 includes a toggle 4022, a toothed gear 4004, and two pawls. The ratchet assembly 4000 is operably coupled to a lock ring 4006, which allows the surgeon to selectively lock and unlock rotational movement of the ratchet assembly relative to the handle 3401 via a release button 4024. A portion of the proximal end of the body of awl-tap member 3406 extends through an inner channel of the toothed gear 4004 such that rotation of the gear 4004 also rotates the awl-tap member 3406.

FIG. 45, as well as FIG. 46, provides further illustrative details regarding the depth sleeve member 3404 and other components of the handheld device 3400 which allow for depth measuring functions, as previously described herein. For example, as shown, depth sleeve collar 3442 is coupled to a proximal end of the depth sleeve member 3404 and a sleeve contact 3444 is coupled to an exterior surface of the sleeve collar 3442, wherein the sleeve contact 3444 is in contact with PCB 3440. The depth sleeve member 3404 is operably coupled to spring 3405, which applies a biasing force upon a spring bearing plate 3403 coupled to the sleeve collar 3442. As such, depth sleeve member 3404 is biased in a direction away from the handle 3401. As shown in FIG. 46, the depth sleeve member 3404 comprises a tubular body 3454 with a proximal end 3456, and a chamfered distal edge on a distal end 3458 of the tubular body 3454. The chamfered distal edge of sleeve member 3406 provides a beveled edge that tapers inward at a right or an acute angle. This tapered distal edge facilitates engagement with a periphery of a hole as the hole is being formed, and further facilitates depth measurement of the hole, as previously described herein. The sleeve member 3404 also includes a flange 3460 extending outward from the body 3454. When sleeve member 3404 is coupled to the sleeve collar 3442 and sleeve contact 3444, the sleeve collar 3442 may rest upon flange 3460, thereby maintaining the sleeve contact 3444 in connection therewith in a stationary position relative to the body 3454 of the sleeve member 3404.

Accordingly, the handheld device of the present disclosure allows a surgeon to form a hole for a bone fixation procedure, perform and control neurostimulation and neuromonitoring functions during hole formation to ensure accuracy and safety during hole formation, and further measure a depth of the hole, all in a sterile environment and through use of a single device. The surgeon may perform all such aspects of the bone fixation procedure while receiving real-time or near real-time digital feedback on a display of the handheld device.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A handheld device for a bone implant fixation procedure, the device comprising:
    a handle;
    an awl-tap member releasably coupled to the handle, the awl-tap member comprising an electrically conductive body including a distal tip at a distal end thereof for penetrating bone, wherein the awl-tap member is configured to deliver electrical current to the bone and the electrical current is used for the determination of the presence of a nerve adjacent or in proximity to one or more portions of the awl-tap member;
    a depth sleeve member operably associated with the handle and configured to move relative thereto, the depth sleeve member comprising an elongate body including a lumen extending therethrough, wherein at least a portion of the awl-tap member is received within the lumen when the awl-tap member is coupled to the handle and wherein the depth sleeve member and awl-tap member are configured to move independent of one another; and
    a sensor operably associated with the depth sleeve member and configured to detect movement of the depth sleeve member relative to the awl-tap member and to generate an electronic signal indicative of a depth of a hole created by the awl-tap member based on the detected movement.

2. The handheld device of claim 1, wherein the handle is configured to receive one of a plurality of interchangeable awl-tap members releasably couplable thereto.

3. The handheld device of claim 1, wherein a portion of the awl-tap member adjacent to the distal tip is externally threaded such that rotation of the awl-tap member in a first direction causes external threading to penetrate bone and draw the distal tip in a direction towards the bone to form a hole therein and rotation of the awl-tap member in a second direction opposite the first direction causes external threading to withdraw from within the hole and move the awl-tap member in a direction away from the bone.

4. The handheld device of claim 3, wherein the handle is rotatably coupled to the awl-tap member via a ratchet assembly.

5. The handheld device of claim 4, wherein the ratchet assembly comprises a switch for toggling between a first rotation setting and a second rotation setting, wherein:
    in the first rotation setting, rotation of the handle in a first direction results in the awl-tap member rotating in the same direction and rotation of the handle in an opposite second direction is independent of any rotation of the awl-tap member such that awl-tap member remains stationary; and
    in the second rotation setting, rotation of the handle in the first direction is independent of any rotation of the awl-tap member such that the awl-tap member remains stationary and rotation of the handle in the opposite second direction results in the awl-tap member rotating in the same direction.

6. The handheld device of claim 1, further comprising a display provided on the handle and configured to provide a digital readout of the depth of the hole based on the electronic signal.

7. The handheld device of claim 1, further comprising a display provided on the handle and configured to provide a visual indication of the presence of a nerve adjacent or in proximity to one or more portions of the awl-tap member.

8. The handheld device of claim 1, further comprising a display provided on the handle and configured to provide a visual indication of a level of electrical current delivered from the awl-tap member.

9. The handheld device of claim 8, wherein the handle comprises a control device operable to adjust the level of electrical current delivered from the awl-tap member.

10. The handheld device of claim 9, wherein the display is a liquid crystal display or an LED display.

11. A system for a bone implant fixation procedure, the system comprising:
a handheld device comprising:
an awl-tap member releasably coupled to the handle, the awl-tap member comprising an electrically conductive body including a distal tip at a distal end thereof for penetrating bone, wherein the awl-tap member is configured to deliver electrical current to the bone and the electrical current is used for the determination of the presence of a nerve adjacent or in proximity to one or more portions of the awl-tap member;
a depth sleeve member operably associated with the handle and configured to move relative thereto, the depth sleeve member comprising an elongate body including a lumen extending therethrough, wherein at least a portion of the awl-tap member is received within the lumen when the awl-tap member is coupled to the handle and wherein the depth sleeve member and awl-tap member are configured to move independent of one another; and
a sensor operably associated with the depth sleeve member and configured to detect movement of the depth sleeve member relative to the awl-tap member and to generate an electronic signal indicative of a depth of a hole created by the awl-tap member based on the detected movement; and
a neuromonitoring device configured to communicate with at least the awl-tap member, the neuromonitoring device configured to receive the electrical current delivered from the awl-tap member and through the bone and determine the presence of a nerve adjacent or in proximity to one or more portions of the awl-tap member.

12. The system of claim 11, wherein the neuromonitoring device comprises a junction box configured to transmit or receive electrical current to and from the awl-tap member for neurostimulation or neuromonitoring functions when placed in electrical connection with the awl-tap member.

13. The system of claim 12, wherein, the junction box comprises a processor configured to generate and transmit a control signal to the handheld device to adjust a level of electrical current delivered from the awl-tap member.

14. The system of claim 13, wherein the handheld device further comprises a control device operable to adjust the level of electrical current delivered from the awl-tap member by communicating with the processor of the junction box to generate and transmit the control signal.

15. The system of claim 11, wherein the handheld device further comprises a display configured to provide a digital readout of the depth of the hole based on the electronic signal.

16. The system of claim 11, wherein the handheld device further comprises a display configured to visually indicate presence of a nerve adjacent or in proximity to one or more portions of the awl-tap member.

17. The system of claim 11, wherein the handheld device further comprises display configured to provide a digital indication of the level of electrical current delivered from the awl-tap member.

18. The system of claim 11, wherein a portion of the awl-tap member adjacent to the distal tip is externally threaded such that rotation of the awl-tap member in a first direction causes external threading to penetrate bone and draw the distal tip in a direction towards the bone to form a hole therein and rotation of the awl-tap member in a second direction opposite the first direction causes external threading to withdraw from within the hole and move the awl-tap member in a direction away from the bone.

19. The system of claim 18, wherein the handle is rotatably coupled to the awl-tap member via a ratchet assembly.

20. The system of claim 19, wherein the ratchet assembly comprises a switch for toggling between a first rotation setting and a second rotation setting, wherein:
in the first rotation setting, rotation of the handle in a first direction results in the awl-tap member rotating in the same direction and rotation of the handle in an opposite second direction is independent of any rotation of the awl-tap member such that awl-tap member remains stationary; and
in the second rotation setting, rotation of the handle in the first direction is independent of any rotation of the awl-tap member such that the awl-tap member remains stationary and rotation of the handle in the opposite second direction results in the awl-tap member rotating in the same direction.

* * * * *